United States Patent
Presnell et al.

(10) Patent No.: US 8,124,077 B2
(45) Date of Patent: Feb. 28, 2012

(54) ANTI-IL-TIF ANTIBODIES AND METHODS OF MAKING

(75) Inventors: Scott R. Presnell, Tacoma, WA (US); Wayne Kindsvogel, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 12/499,636

(22) Filed: Jul. 8, 2009

(65) Prior Publication Data

US 2010/0080802 A1    Apr. 1, 2010

Related U.S. Application Data

(60) Division of application No. 10/806,294, filed on Mar. 22, 2004, now Pat. No. 7,563,568, which is a continuation of application No. 09/746,375, filed on Dec. 22, 2000, now abandoned.

(60) Provisional application No. 60/172,105, filed on Dec. 23, 1999, provisional application No. 60/250,841, filed on Dec. 1, 2000.

(51) Int. Cl.
*A61K 39/395* (2006.01)

(52) U.S. Cl. ............. 424/130.1; 424/141.1; 424/143.1

(58) Field of Classification Search ................... None
See application file for complete search history.

(56) References Cited

U.S. PATENT DOCUMENTS 4,443,549 A * 4/1984 Sadowski .................. 424/150.1
(Continued)

FOREIGN PATENT DOCUMENTS

EP    1191035 A2    3/2002
(Continued)

OTHER PUBLICATIONS

Klenk et al., Nature:390, 364-370, 1970.*
(Continued)

*Primary Examiner* — Gyan Chandra
(74) *Attorney, Agent, or Firm* — Nelson Mullins Riley & Scarborough LLP; Jane E. Remillard, Esq.; Jill Gorny Sloper, Esq.

(57) ABSTRACT

The present invention relates to ZCYTO18 polynucleotide and polypeptide molecules. The ZCYTO18 is a novel cytokine. The polypeptides may be used within methods for stimulating the proliferation and/or development of hematopoietic cells in vitro and in vivo. The present invention also includes methods for producing the protein, uses therefor and antibodies thereto.

9 Claims, 1 Drawing Sheet

U.S. PATENT DOCUMENTS

| | | | |
|---|---|---|---|
| 5,397,569 A * | 3/1995 | Whitfill et al. | 424/178.1 |
| 5,488,032 A | 1/1996 | Dower et al. | |
| 5,965,704 A | 10/1999 | Lok et al. | |
| 6,013,503 A | 1/2000 | Lok et al. | |
| 6,274,710 B1 | 8/2001 | Dumoutier et al. | |
| 6,551,799 B2 | 4/2003 | Gurney et al. | |
| 2003/0022827 A1 | 1/2003 | Weiss et al. | |
| 2003/0170823 A1 | 9/2003 | Presnell et al. | |
| 2004/0152125 A1 | 8/2004 | Presnell et al. | |

FOREIGN PATENT DOCUMENTS

| | | |
|---|---|---|
| WO | 98/02542 A1 | 1/1998 |
| WO | 98/37193 A1 | 8/1998 |
| WO | 99/07848 A1 | 2/1999 |
| WO | 00/39161 A1 | 7/2000 |
| WO | 01/36467 A2 | 5/2001 |
| WO | 01/46422 A1 | 6/2001 |
| WO | 01/98342 A1 | 12/2001 |
| WO | 02/10393 A2 | 2/2002 |
| WO | 02/16611 A2 | 2/2002 |
| WO | 02/20569 A2 | 3/2002 |
| WO | 02/24912 A2 | 3/2002 |
| WO | 02/066647 A2 | 8/2002 |
| WO | 02/068476 A2 | 9/2002 |
| WO | 02/072607 A2 | 9/2002 |
| WO | 03/035096 A1 | 5/2003 |

OTHER PUBLICATIONS

EPO Communication; May 8, 2007; 11pp.

Ballow, Mark et al., "Immunopharmacology, Immunomodulation and Immunotherapy," JAMA, vol. 278 (22):2008-2017 (1997).

Bleicher, Lucas et al., "Crystal structure of the IL-22/IL-22R1 complex and its implications for the IL-22 signaling mechanism," FEBS Letters, vol. 582:2985-2992 (2008).

Blumberg, Hal et al., "Interleukin 20: Discovery, Receptor Identification, and Role in Epidermal Function," Cell, vol. 104:9-19 (2001).

Bork, Peer et al., "Go hunting in sequence databases but watch out for the traps," TIG, vol. 12(10):425-427 (1996).

Bork, Peer, "Powers and Pitfalls in Sequence Analysis: The 70% Hurdle," Genome Research, vol. 10:398-400 (2000).

Bork, Peer et al., "Predicting functions from protein sequences—where are the bottlenecks?" Nature Genetics, vol. 18(4):313-318 (1998).

Dillman, Robert O. et al., "Monoclonal Antibodies in the Treatment of Malignancy: Basic Concepts and Recent Developments," Cancer Investigation, vol. 19(8):833-841 (2001).

Dumoutier, Laure et al., "Cloning and Characterization of IL-22 Binding Protein, a Natural Antagonist of IL-10-Related T Cell-Derived Inducible Factor/IL-22," The Journal of Immunology, vol. 166:7090-7095 (2001).

Dumoutier, Laure et al., "Cutting Edge: STAT Activation by IL-19, IL-20 and mda-7 Through IL-20 Receptor Complexes of Two Types," The Journal of Immunology, vol. 167:3545-3549 (2001).

GenBank Accession No. AA132964 (2011).

GenBank Accession No. AC007458 (2003).

GenBank Accession No. AV714177 (2000).

GenBank Accession No. T70354 (1995).

GenBank Accession No. T70439 (1995).

Gruenberg, B.H. et al., "A novel, soluble homologue of the human IL-10 receptor with preferential expression in placenta," Genes and Immunity, vol. 2:329-334 (2001).

Incyte Pharmaceuticals, Inc. clone, SHLW01158999 (1999).

Kotenko, Sergei V. et al., "Identification, Cloning, and Characterization of a Novel Soluble Receptor That Binds IL-22 and Neutralizes Its Activity," The Journal of Immunology, vol. 166:7096-7103 (2001).

Kotenko, Sergei V. et al., "Identification of the Functional Interleukin-22 (IL-22) Receptor Complex," The Journal of Biological Chemistry, vol. 276(4):2725-2732 (2001).

Kotenko, Sergei V. et al., "Jak-Stat signal transduction pathway through the eyes of cytokine class II receptor complexes," Oncogene, vol. 19:2557-2565 (2000).

Liu, Ying et al., "Expression Cloning and Characterization of a Human IL-10 Receptor," Journal of Immunology, vol. 152(4):1821-1829 (1994).

Moore, Gordon P., "Genetically Engineered Antibodies," Clinical Chemistry, vol. 35(9):1849-1853 (1989).

Parrish-Novak, Julia et al., "Interleukins 19, 20, and 24 Signal through Two Distinct Receptor Complexes," The Journal of Biological Chemistry, vol. 277(49):47517-47523 (2002).

Sempowski, Gregory D. et al., "Subsets of Murine Lung Fibroblasts Express Membrane-Bound and Soluble IL-4 Receptors," Journal of Immunology, vol. 152(7):3606-3614 (1994).

Uhlar, Clarissa M. et al., "Serum amyloid A, the major vertebrate acute-phase reactant," Eur. J. Biochem., vol. 265:501-523 (1999).

Wei, Chi-Chen et al., "Cloning and characterization of mouse IL-22 binding protein," Genes and Immunity, vol. 4:204-211 (2003).

Wells, James A., "Additivity of Mutational Effects in Proteins," Biochemistry, vol. 29(37):8509-8517 (1990).

Xu, Wenfeng et al., "A soluble class II cytokine receptor, IL-22RA2, is a naturally occurring IL-22 antagonist," PNAS, vol. 98(17):9511-9516 (2001).

Zhang, Jian-Guo et al., "Identification, Purification, and Characterization of a Soluble Interleukin (IL)-13-binding Protein," The Journal of Biological Chemistry, vol. 272(14):9474-9480 (1997).

* cited by examiner

```
hZCYTO18              MGTLATSCLLLLALLVQGGAAAPISSHCRLDKSNFQQPYITNRTFMLA
mZCYTO18    MAVLQKSMSFSLMGTLAASCLLLIALWAQEANALPVNTRCKLEVSNFQQPYIVNRTFMLA hZCYTO18    KEASLADNNTDVRLIGEKLFHGVSMSERCYLMKQVLNFTLEEVLFPQSDRFQPYMQEVVP
mZCYTO18    KEASLADNNTDVRLIGEKLFRGVNAKDQCYLMKQVLNFTLEDVLLPQSDRFQPYMQEVVP hZCYTO18    FLARLSNRLSTCHIEGDDLHIQRNVQKLKDTVKKLGESGEIKAIGELDLLEMSLRNACI
mZCYTO18    FLTKLSNQLSSCHISGDDQNIQKNVRRLKETVKKLGESGEIKAIGELDLLEMSLRNACV
```

ANTI-IL-TIF ANTIBODIES AND METHODS OF MAKING

REFERENCE TO RELATED APPLICATIONS

This application is a divisional of U.S. patent application Ser. No. 10/806,294, filed on Mar. 22, 2004, now U.S. Pat. No. 7,563,568, which is a continuation of U.S. patent application Ser. No. 09/746,375, filed on Dec. 22, 2000, now abandoned which claims benefit of U.S. Provisional Application Ser. No. 60/172,105, filed on Dec. 23, 1999, and U.S. Provisional Application Ser. No. 60/250,841, filed on Dec. 1, 2000, all of which are herein incorporated by reference. Under 35 U.S.C. §119(e)(1), this application claims benefit of said Provisional Applications.

BACKGROUND OF THE INVENTION

Hormones and polypeptide growth factors control proliferation and differentiation of cells of multicellular organisms. These diffusible molecules allow cells to communicate with each other and act in concert to form cells and organs, and to repair damaged tissue. Examples of hormones and growth factors include the steroid hormones (e.g. estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to receptors. Receptors may be integral membrane proteins that are linked to signaling pathways within the cell, such as second messenger systems. Other classes of receptors are soluble molecules, such as the nuclear receptors or transcription factors.

Cytokines generally stimulate proliferation or differentiation of cells of the hematopoietic lineage or participate in the immune and inflammatory response mechanisms of the body. Examples of cytokines that affect hematopoiesis are erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia, thrombocytopenia, and neutropenia or receiving chemotherapy for cancer.

The interleukins are a family of cytokines that mediate immunological responses, including inflammation. The interleukins mediate a variety of inflammatory pathologies. Central to an immune response is the T cell, which produce many cytokines and adaptive immunity to antigens. Cytokines produced by the T cell have been classified as type 1 and type 2 (Kelso, A. *Immun. Cell Biol.* 76:300-317, 1998). Type 1 cytokines include IL-2, IFN-γ, LT-α, and are involved in inflammatory responses, viral immunity, intracellular parasite immunity and allograft rejection. Type 2 cytokines include IL-4, IL-5, IL-6, IL-10 and IL-13, and are involved in humoral responses, helminth immunity and allergic response. Shared cytokines between Type 1 and 2 include IL-3, GM-CSF and TNF-α. There is some evidence to suggest that Type 1 and Type 2 producing T cell populations preferentially migrate into different types of inflamed tissue.

Mature T cells may be activated, i.e., by an antigen or other stimulus, to produce, for example, cytokines, biochemical signaling molecules, or receptors that further influence the fate of the T cell population.

B cells can be activated via receptors on their cell surface including B cell receptor and other accessory molecules to perform accessory cell functions, such as production of cytokines.

Natural killer (NK) cells have a common progenitor cell with T cells and B cells, and play a role in immune surveillance. NK cells, which comprise up 15% of blood lymphocytes, do not express antigen receptors, and therefore do not use MHC recognition as requirement for binding to a target cell. NK cells are involved in the recognition and killing of certain tumor cells and virally infected cells. In vivo, NK cells are believed to require activation, however, in vitro, NK cells have been shown to kill some types of tumor cells without activation.

The demonstrated in vivo activities of the cytokine family illustrates the enormous clinical potential of, and need for, other cytokines, cytokine agonists, and cytokine antagonists. The present invention addresses these needs by providing a new cytokine that stimulates multiple cell types including hematopoietic cells, and participates in the inflammatory response and tumor cell growth, as well as related compositions and methods.

BRIEF DESCRIPTION OF THE DRAWING

FIG. 1 is a multiple alignment of the human ZCYTO18 polypeptide (hZCYTO18) (SEQ ID NO:3), and the mouse ZCYTO18 polypeptide (mZCYTO18) (SEQ ID NO:38) of the present invention. The ":" in the FIGURE indicates amino acids that are identical between the mouse and human sequences, and the "." in the FIGURE indicates amino acids that are conserved substitutions. There is a 78.4% identity between the human and mouse sequences over the entire sequence (167 amino acid overlap).

DESCRIPTION OF THE INVENTION

The present invention provides such polypeptides for these and other uses that should be apparent to those skilled in the art from the teachings herein.

Within one aspect, the present invention provides an isolated polynucleotide that encodes a cytokine polypeptide comprising a sequence of amino acid residues that is at least 90% identical to an amino acid sequence selected from the group consisting of: (a) the amino acid sequence as shown in SEQ ID NO:3 from amino acid number 23 (Pro), to amino acid number 167 (Ile); (b) the amino acid sequence as shown in SEQ ID NO:3 from amino acid number 1 (Met), to amino acid number 167 (Ile); and (c) the amino acid sequence as shown in SEQ ID NO:2 from amino acid number 1 (Met), to amino acid number 179 (Ile); and wherein the polypeptide produced by the cell induces proliferation of cells expressing a receptor for the polypeptide comprising zcytor11 (SEQ ID NO:19) or induces cytotoxicity in K562 cells. In one embodiment, the isolated polynucleotide disclosed above is selected from the group consisting of: (a) a polynucleotide sequence as shown in SEQ ID NO:1 from nucleotide 123 to nucleotide 557; (b) a polynucleotide sequence as shown in SEQ ID NO:1 from nucleotide 57 to nucleotide 557; and (c) a polynucleotide sequence as shown in SEQ ID NO:1 from nucleotide 21 to nucleotide 557; and (d) a polynucleotide sequence complementary to (a), (b) or (c). In another embodiment, the isolated polynucleotide disclosed above comprises nucleotide 1 to nucleotide 501 of SEQ ID NO:4. In another embodiment, the isolated polynucleotide disclosed above encodes a cytokine polypeptide that comprises a sequence of amino acid residues selected from the group consisting of: (a) the amino acid sequence as shown in SEQ ID NO:3 from amino acid number 23 (Pro), to amino acid number 167 (Ile); (b) the amino acid sequence as shown in SEQ ID NO:3 from amino acid number 1 (Met), to amino acid number 167 (Ile); and (c) the amino acid sequence as shown in SEQ ID NO:2 from amino acid number 1 (Met), to amino acid number 179 (Ile).

Within a second aspect, the present invention provides an expression vector comprising the following operably linked elements: a transcription promoter; a DNA segment encoding a cytokine polypeptide as shown in SEQ ID NO:3 from amino acid number 23 (Pro), to amino acid number 167 (Ile); and a transcription terminator, wherein the promoter is operably linked to the DNA segment, and the DNA segment is operably linked to the transcription terminator. In one embodiment, the expression vector disclosed above further comprises a secretory signal sequence operably linked to the DNA segment.

Within a third aspect, the present invention provides a cultured cell comprising an expression vector according as disclosed above, wherein the cell expresses a polypeptide encoded by the DNA segment.

Within a fourth aspect, the present invention provides a DNA construct encoding a fusion protein, the DNA construct comprising: a first DNA segment encoding a polypeptide comprising a sequence of amino acid residues selected from the group consisting of: (a) the amino acid sequence as shown in SEQ ID NO:3 from amino acid number 1 (Met), to amino acid number 21 (Ala); (b) the amino acid sequence as shown in SEQ ID NO:3 from amino acid number 41 (Thr), to amino acid number 53 (Leu); (c) the amino acid sequence as shown in SEQ ID NO:3 from amino acid number 80 (Met), to amino acid number 91 (Val); (d) the amino acid sequence as shown in SEQ ID NO:3 from amino acid number 103 (Gln), to amino acid number 116 (Arg); (e) the amino acid sequence as shown in SEQ ID NO:3 from amino acid number 149 (Ile), to amino acid number 162 (Leu); and (f) the amino acid sequence as shown in SEQ ID NO:3 from amino acid number 23 (Pro), to amino acid number 167 (Ile); and at least one other DNA segment encoding an additional polypeptide, wherein the first and other DNA segments are connected in-frame; and wherein the first and other DNA segments encode the fusion protein.

Within another aspect, the present invention provides an expression vector comprising the following operably linked elements: a transcription promoter; a DNA construct encoding a fusion protein as disclosed above; and a transcription terminator, wherein the promoter is operably linked to the DNA construct, and the DNA construct is operably linked to the transcription terminator.

Within another aspect, the present invention provides a cultured cell comprising an expression vector as disclosed above, wherein the cell expresses a polypeptide encoded by the DNA construct.

Within another aspect, the present invention provides a method of producing a fusion protein comprising: culturing a cell according as disclosed above; and isolating the polypeptide produced by the cell.

Within another aspect, the present invention provides an isolated cytokine polypeptide comprising a sequence of amino acid residues that is at least 90% identical to an amino acid sequence selected from the group consisting of: (a) the amino acid sequence as shown in SEQ ID NO:3 from amino acid number 23 (Pro), to amino acid number 167 (Ile); (b) the amino acid sequence as shown in SEQ ID NO:3 from amino acid number 1 (Met), to amino acid number 167 (Ile); and (c) the amino acid sequence as shown in SEQ ID NO:2 from amino acid number 1 (Met), to amino acid number 179 (Ile); and wherein the polypeptide produced by the cell induces proliferation of cells expressing a receptor for the polypeptide comprising zcytor11 (SEQ ID NO:19) or induces cytotoxicity in K562 cells. In one embodiment, the isolated polypeptide disclosed above comprises a sequence of amino acid residues selected from the group consisting of: (a) the amino acid sequence as shown in SEQ ID NO:3 from amino acid number 23 (Pro), to amino acid number 167 (Ile); (b) the amino acid sequence as shown in SEQ ID NO:3 from amino acid number 1 (Met), to amino acid number 167 (Ile); and (c) the amino acid sequence as shown in SEQ ID NO:2 from amino acid number 1 (Met), to amino acid number 179 (Ile).

Within another aspect, the present invention provides a method of producing a cytokine polypeptide comprising: culturing a cell as disclosed above; and isolating the cytokine polypeptide produced by the cell.

Within another aspect, the present invention provides a method of producing an antibody to a polypeptide comprising: inoculating an animal with a polypeptide selected from the group consisting of: (a) a polypeptide consisting of 30 to 144 amino acids, wherein the polypeptide is identical to a contiguous sequence of amino acids in SEQ ID NO:3 from amino acid number 23 (Gly) to amino acid number 779 (Thr); (b) a polypeptide as disclosed above; (c) a polypeptide consisting of the amino acid sequence of SEQ ID NO:3 from amino acid number 29 (Arg) to amino acid number 34 (Asn); (d) a polypeptide consisting of the amino acid sequence of SEQ ID NO:3 from amino acid number 121 (His) to amino acid number 126 (Asp); (e) a polypeptide consisting of the amino acid sequence of SEQ ID NO:3 from amino acid number 134 (Gln) to amino acid number 139 (Thr); (f) a polypeptide consisting of the amino acid sequence of SEQ ID NO:3 from amino acid number 137 (Lys) to amino acid number 142 (Lys); (g) a polypeptide consisting of the amino acid sequence of SEQ ID NO:3 from amino acid number 145 (Glu) to amino acid number 150 (Lys); (h) a polypeptide consisting of the amino acid sequence of SEQ ID NO:3 from amino acid number 41 (Thr), to amino acid number 53 (Leu); (i) a polypeptide consisting of the amino acid sequence of SEQ ID NO:3 from amino acid number 80 (Met) to amino acid number 91 (Val); (j) a polypeptide consisting of the amino acid sequence of SEQ ID NO:3 from amino acid number 103 (Met) to amino acid number 116 (Arg); (k) a polypeptide consisting of the amino acid sequence of SEQ ID NO:3 from amino acid number 149 (Ile) to amino acid number 162 (Leu); and wherein the polypeptide elicits an immune response in the animal to produce the antibody; and isolating the antibody from the animal.

Within another aspect, the present invention provides an antibody produced by the method as disclosed above, which binds to a polypeptide of SEQ ID NO:2 or SEQ ID NO:3. In one embodiment, the antibody disclosed above is a monoclonal antibody. Within another aspect, the present invention provides an antibody which specifically binds to a polypeptide as disclosed above.

Within another aspect, the present invention provides a method of detecting, in a test sample, the presence of an antagonist of ZCYTO18 protein activity, comprising: culturing a cell that is responsive to a ZCYTO18-stimulated cellular pathway; and producing a polypeptide by the method as disclosed above; and exposing the polypeptide to the cell, in the presence and absence of a test sample; and comparing levels of response to the polypeptide, in the presence and absence of the test sample, by a biological or biochemical assay; and determining from the comparison, the presence of the antagonist of ZCYTO18 activity in the test sample.

Within another aspect, the present invention provides a method of detecting, in a test sample, the presence of an agonist of ZCYTO18 protein activity, comprising: culturing a cell that is responsive to a ZCYTO18-stimulated cellular pathway; and adding a test sample; and comparing levels of response in the presence and absence of the test sample, by a biological or biochemical assay; and determining from the comparison, the presence of the agonist of ZCYTO18 activity in the test sample.

Within another aspect, the present invention provides a method for detecting a genetic abnormality in a patient, comprising: obtaining a genetic sample from a patient; producing a first reaction product by incubating the genetic sample with a polynucleotide comprising at least 14 contiguous nucleotides of SEQ ID NO:1 or the complement of SEQ ID NO:1, under conditions wherein said polynucleotide will hybridize to complementary polynucleotide sequence; visualizing the first reaction product; and comparing said first reaction product to a control reaction product from a wild type patient, wherein a difference between said first reaction product and said control reaction product is indicative of a genetic abnormality in the patient.

Within another aspect, the present invention provides a method for detecting a cancer in a patient, comprising: obtaining a tissue or biological sample from a patient; incubating the tissue or biological sample with an antibody as disclosed above under conditions wherein the antibody binds to its complementary polypeptide in the tissue or biological sample; visualizing the antibody bound in the tissue or biological sample; and comparing levels of antibody bound in the tissue or biological sample from the patient to a normal control tissue or biological sample, wherein an increase or decrease in the level of antibody bound to the patient tissue or biological sample relative to the normal control tissue or biological sample is indicative of a cancer in the patient.

Within another aspect, the present invention provides a method for detecting a cancer in a patient, comprising: obtaining a tissue or biological sample from a patient; labeling a polynucleotide comprising at least 14 contiguous nucleotides of SEQ ID NO:1 or the complement of SEQ ID NO:1; incubating the tissue or biological sample with under conditions wherein the polynucleotide will hybridize to complementary polynucleotide sequence; visualizing the labeled polynucleotide in the tissue or biological sample; and comparing the level of labeled polynucleotide hybridization in the tissue or biological sample from the patient to a normal control tissue or biological sample, wherein an increase or decrease in the labeled polynucleotide hybridization to the patient tissue or biological sample relative to the normal control tissue or biological sample is indicative of a cancer in the patient.

Within another aspect, the present invention provides a method of killing cancer cells comprising, obtaining ex vivo a tissue or biological sample containing cancer cells from a patient, or identifying cancer cells in vivo; producing a polypeptide by the method as disclosed above; formulating the polypeptide in a pharmaceutically acceptable vehicle; and administering to the patient or exposing the cancer cells to the polypeptide; wherein the polypeptide kills the cells. In one embodiment, the method of killing cancer cells is as disclosed above, wherein the polypeptide is further conjugated to a toxin.

Within another aspect, the present invention provides a method of increasing platelets in a patient or injured tissue, producing a polypeptide by the method as disclosed above; administering the polypeptide to the patient or injured tissue in a pharmaceutically acceptable vehicle, wherein the polypeptide increases the level pf platelets in the patient or injured tissue.

Within another aspect, the present invention provides a method for detecting inflammation in a patient, comprising: obtaining a tissue or biological sample from a patient; incubating the tissue or biological sample with an antibody as disclosed above under conditions wherein the antibody binds to its complementary polypeptide in the tissue or biological sample; visualizing the antibody bound in the tissue or biological sample; and comparing levels of antibody bound in the tissue or biological sample from the patient to a normal control tissue or biological sample, wherein an increase in the level of antibody bound to the patient tissue or biological sample relative to the normal control tissue or biological sample is indicative of inflammation in the patient.

Within another aspect, the present invention provides a method for detecting inflammation in a patient, comprising: obtaining a tissue or biological sample from a patient; labeling a polynucleotide comprising at least 14 contiguous nucleotides of SEQ ID NO:1 or the complement of SEQ ID NO:1; incubating the tissue or biological sample with under conditions wherein the polynucleotide will hybridize to complementary polynucleotide sequence; visualizing the labeled polynucleotide in the tissue or biological sample; and comparing the level of labeled polynucleotide hybridization in the tissue or biological sample from the patient to a normal control tissue or biological sample, wherein an increase in the labeled polynucleotide hybridization to the patient tissue or biological sample relative to the normal control tissue or biological sample is indicative of inflammation in the patient.

These and other aspects of the invention will become evident upon reference to the following detailed description of the invention.

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9 M^{-1}$.

The term "complements of a polynucleotide molecule" denotes a polynucleotide molecule having a complementary base sequence and reverse orientation as compared to a reference sequence. For example, the sequence 5' ATG-CACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, $\alpha$-globin, $\beta$-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

"Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14-17 nucleotides) can be used. PCR primers are at least 5 nucleotides in length, preferably 15 or more nt, more preferably 20-30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a protein having the structure of a four-helical-bundle cytokine. Through processes of cloning, and expression studies described herein, a polynucleotide sequence encoding a novel ligand polypeptide has been identified. This polypeptide ligand, designated ZCYTO18, was isolated from T-cell cDNA library and mixed lymphocyte reaction (MLR) cDNA and is expressed in activated human peripheral blood cells (hPBCs), which were selected for CD3. CD3 is a cell surface marker unique to cells of lymphoid origin, particularly T cells. Based on Northern and RT-PCR analysis, ZCYTO18 polynucleotides are expressed in T-cells, activated T- and B-cells, and lymphoid tissue. The human ZCYTO18 nucleotide sequence is represented in SEQ ID NO:1.

Analysis of SEQ ID NO:1 reveals that there are two possible initiation Methionine residues for a ZCYTO18 cytokine polypeptide translated therefrom. The two deduced ZCYTO18 polypeptide amino acid sequences are shown in SEQ ID NO:2 (a 179 amino acid polypeptide having the initiating Met at nucleotide 21 in SEQ ID NO:1) and SEQ ID NO:3 (a 167 amino acid polypeptide having the initiating Met at nucleotide 57 in SEQ ID NO:1). Although both of these sequences encode a ZCYTO18 polypeptide, based on similarity of the ZCYTO18 sequence to IL-10 and other cytokines, and the presence of a strong signal sequence, SEQ ID NO:3 encodes a fully functional secreted cytokine polypeptide.

Sequence analysis of the deduced amino acid sequence as represented in SEQ ID NO:3 indicates a 167 amino acid polypeptide containing a 22 amino acid residue secretory signal sequence (amino acid residues 1 (Met) to 21 (Ala) of SEQ ID NO:3), and a mature polypeptide of 146 amino acids (amino acid residues 22 (Ala) to 167 (Ile) of SEQ ID NO:3). N-terminal sequence shows that the mature start at residue 22 (Ala) of SEQ ID NO:3 or 34 (Ala) of SEQ ID NO:2.

In general, cytokines are predicted to have a four-alpha helix structure, with the $1^{st}$ and $4^{th}$ helices being most important in ligand-receptor interactions. The $1^{st}$ and $4^{th}$ helices are more highly conserved among members of the family. Referring to the human ZCYTO18 amino acid sequence shown in SEQ ID NO:3, alignment of human ZCYTO18, human IL-10, human zcyto10 (WO US98/25228), and human Human MDA7 (Genbank Accession No. Q13007) amino acid sequences suggests that ZCYTO18 helix A is defined by amino acid residues 41 (Thr) to 53 (leu) of SEQ ID NO:3; helix B by amino acid residues 80 (Met) to 91 (Val) of SEQ ID NO:3; helix C by amino acid residues 103 (Met) to 116 (Arg) of SEQ ID NO:3; and helix D by amino acid residues 149 (Ile) to 162 Leu) of SEQ ID NO:3. Structural analysis suggests that the A/B loop is long, the B/C loop is short and the C/D loop is long. This loop structure results in an up-up-down-down helical organization. Four cysteine residues are conserved between IL-10 and ZCYTO18 corresponding to amino acid residues 8, 28, 77 and 120 of SEQ ID NO:3. Consistent cysteine placement is further confirmation of the four-helical-bundle structure.

The corresponding polynucleotides encoding the ZCYTO18 polypeptide regions, domains, motifs, residues and sequences described herein are as shown in SEQ ID NO:1. Moreover, the corresponding ZCYTO18 polypeptide regions, domains, motifs, residues and sequences described herein are also as shown in SEQ ID NO:2.

Four-helical bundle cytokines are also grouped by the length of their component helices. "Long-helix" form cytokines generally consist of between 24-30 residue helices and include IL-6, ciliary neutrotrophic factor (CNTF), leukemia inhibitory factor (LIF) and human growth hormone (hGH). "Short-helix" form cytokines generally consist of between 18-21 residue helices and include IL-2, IL-4 and GM-CSF. Zcyto18 is believed to be a new member of the short-helix form cytokine group. Studies using CNTF and IL-6 demonstrated that a CNTF helix can be exchanged for the equivalent helix in IL-6, conferring CTNF-binding properties to the chimera. Thus, it appears that functional domains of four-helical cytokines determined on the basis of structural homology, irrespective of sequence identity, and can maintain functional integrity in a chimera (Kallen et al., *J. Biol. Chem.* 274:11859-11867, 1999). Using similar methods, putative regions conferring receptor binding specificity in ZCYTO18 comprise the regions of amino acid residues of SEQ ID NO:3 that include: residues 53-60, residues 85-91, and residues 121-140. These regions will be useful for preparing chimeric molecules, particularly with other short-helix form cytokines to determine and modulate receptor binding specificity.

Subsequent to filing, ZCYTO18 was annotated in the literature as IL-TIF. Moreover, receptors for ZCYTO18 were identified comprising zcytor16 (SEQ ID NO:32, and SEQ ID NO:33) ((commonly owned PCT International Application No. PCT/US00/32703, filed on Dec. 1, 2000)), zcytor11 (SEQ ID NO:18, and SEQ ID NO:19) (Commonly owned U.S. Pat. No. 5,965,704), and CRF2-4 (Genbank Accession No. Z17227). Moreover several ZCYTO18 responsive cell lines have been identified (Dumontier et al., J. Immunol. 164:1814-1819, 2000; Dumoutier, L. et al., Proc. Nat'l. Acad. Sci. 97:10144-10149, 2000; Xie MH et al., J. Biol. Chem. 275: 31335-31339, 2000; Kotenko SV et al., JBC in press), as well as those that express the ZCYTO18 receptor subunit zcytor11. Moreover, commonly owned zcytor16 receptor was shown to bind ZCYTO18 and antagonize its activity (SEQ ID NO:3) (commonly owned PCT International Application No. PCT/US00/32703, filed on Dec. 1, 2000); the mouse IL-TIF (ZCYTO18) sequence is shown in Dumontier et al., J. Immunol. 164:1814-1819, 2000), and was independently cloned, designated, mouse ZCYTO18 herein, and is shown in SEQ ID NO:37 and corresponding plypeptide sequence shown in SEQ ID NO:38. Moreover, commonly owned zcytor11 (U.S. Pat. No. 5,965,704) and CRF2-4 receptor also bind ZCYTO18 (See, WIPO publication WO 00/24758; Dumontier et al., J. Immunol. 164:1814-1819, 2000; Spencer, SD et al., J. Exp. Med. 187:571-578, 1998; Gibbs, VC and Pennica Gene 186:97-101, 1997 (CRF2-4 cDNA); Xie, MH et al., J. Biol. Chem. 275: 31335-31339, 2000; and Kotenko, SV et al., J. Biol. Chem. manuscript in press M007837200). Moreover, IL-10β receptor may be involved as a receptor for ZCYTO18, and it is believed to be synonymous with CRF2-4 (Dumoutier, L. et al., Proc. Nat'l. Acad. Sci. 97:10144-10149, 2000; Liu Y et al, J Immunol. 152; 1821-1829, 1994 (IL-10R cDNA). These receptors are discussed herein in relation to the uses of ZCYTO18.

The present invention provides polynucleotide molecules, including DNA and RNA molecules, that encode the ZCYTO18 polypeptides disclosed herein. Those skilled in the art will readily recognize that, in view of the degeneracy of the genetic code, considerable sequence variation is possible among these polynucleotide molecules. SEQ ID NO:4 is a degenerate DNA sequence that encompasses all DNAs that encode the ZCYTO18 polypeptide of SEQ ID NO:3. Those skilled in the art will recognize that the degenerate sequence of SEQ ID NO:4 also provides all RNA sequences encoding SEQ ID NO:3 by substituting U for T. Thus, ZCYTO18 polypeptide-encoding polynucleotides comprising nucleotide 1 or 66 to nucleotide 501 of SEQ ID NO:4 and their RNA equivalents are contemplated by the present invention. Table 1 sets forth the one-letter codes used within SEQ ID NO:4 to denote degenerate nucleotide positions. "Resolutions" are the nucleotides denoted by a code letter. "Complement" indicates the code for the complementary nucleotide(s). For example, the code Y denotes either C or T, and its complement R denotes A or G, with A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:4, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:3. Variant sequences can be readily tested for functionality as described herein.

One of ordinary skill in the art will also appreciate that different species can exhibit "preferential codon usage." In general, see, Grantham, et al., *Nuc. Acids Res.* 8:1893-912, 1980; Haas, et al. *Curr. Biol.* 6:315-24, 1996; Wain-Hobson, et al., *Gene* 13:355-64, 1981; Grosjean and Fiers, *Gene*

18:199-209, 1982; Holm, *Nuc. Acids Res.* 14:3075-87, 1986; Ikemura, *J. Mol. Biol.* 158:573-97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:4 serves as a template for optimizing expression of polynucleotides in various cell types and species commonly used in the art and disclosed herein. Sequences containing preferential codons can be tested and optimized for expression in various species, and tested for functionality as disclosed herein.

As previously noted, the isolated polynucleotides of the present invention include DNA and RNA. Methods for preparing DNA and RNA are well known in the art. In general, RNA is isolated from a tissue or cell that produces large amounts of ZCYTO18 RNA. Such tissues and cells are identified by Northern blotting (Thomas, *Proc. Natl. Acad. Sci. USA* 77:5201, 1980), reverse transcriptase PCR(RT-PCR) or by screening conditioned medium from various cell types for activity on target cells or tissue. Once the activity or RNA producing cell or tissue is identified, total RNA can be prepared using guanidinium isothiocyanate extraction followed by isolation by centrifugation in a CsCl gradient (Chirgwin et al., *Biochemistry* 18:52-94, 1979). Poly (A)$^+$RNA is prepared from total RNA using the method of Aviv and Leder (*Proc. Natl. Acad. Sci. USA* 69:1408-12, 1972). Complementary DNA (cDNA) is prepared from poly(A)$^+$RNA using known methods. In the alternative, genomic DNA can be isolated. Polynucleotides encoding ZCYTO18 polypeptides are then identified and isolated by, for example, hybridization or PCR.

A full-length clone encoding ZCYTO18 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to ZCYTO18 fragments, or other specific binding partners.

Zcyto18 polynucleotide sequences disclosed herein can also be used as probes or primers to clone 5' non-coding regions of a ZCYTO18 gene. In view of the tissue-specific expression observed for ZCYTO18 by Northern blotting and RT PCR (See, Examples 2 and 3), this gene region is expected to provide for hematopoietic- and lymphoid-specific expression. Promoter elements from a ZCYTO18 gene could thus be used to direct the tissue-specific expression of heterologous genes in, for example, transgenic animals or patients treated with gene therapy. Cloning of 5' flanking sequences also facilitates production of ZCYTO18 proteins by "gene activation" as disclosed in U.S. Pat. No. 5,641,670. Briefly, expression of an endogenous ZCYTO18 gene in a cell is altered by introducing into the ZCYTO18 locus a DNA construct comprising at least a targeting sequence, a regulatory sequence, an exon, and an unpaired splice donor site. The targeting sequence is a ZCYTO18 5' non-coding sequence that permits homologous recombination of the construct with the endogenous ZCYTO18 locus, whereby the sequences within the construct become operably linked with the endogenous ZCYTO18 coding sequence. In this way, an endogenous ZCYTO18 promoter can be replaced or supplemented with other regulatory sequences to provide enhanced, tissue-specific, or otherwise regulated expression.

The present invention further provides counterpart polypeptides and polynucleotides from other species (orthologs). These species include, but are not limited to mammalian, avian, amphibian, reptile, fish, insect and other vertebrate and invertebrate species. Of particular interest are ZCYTO18 polypeptides from other mammalian species, including murine, porcine, ovine, bovine, canine, feline, equine, and other primate polypeptides. Orthologs of human ZCYTO18 can be cloned using information and compositions provided by the present invention in combination with conventional cloning techniques. For example, a cDNA can be cloned using mRNA obtained from a tissue or cell type that expresses ZCYTO18 as disclosed herein. Suitable sources of mRNA can be identified by probing Northern blots with probes designed from the sequences disclosed herein. A library is then prepared from mRNA of a positive tissue or cell line. A ZCYTO18-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human ZCYTO18 sequence disclosed herein. Within an additional method, the cDNA library can be used to transform or transfect host cells, and expression of the cDNA of interest can be detected with an antibody to ZCYTO18 polypeptide, binding studies or activity assays. Similar techniques can also be applied to the isolation of genomic clones. Example 5 shows that a ZCYTO18 ortholog is present in mouse genomic DNA.

A polynucleotide sequence for the mouse ortholog of human ZCYTO18 has been identified and is shown in SEQ ID NO:37 and the corresponding amino acid sequence shown in SEQ ID NO:38. Analysis of the mouse ZCYTO18 polypeptide encoded by the DNA sequence of SEQ ID NO:37 revealed an open reading frame encoding 179 amino acids (SEQ ID NO:38) comprising a predicted secretory signal peptide of 33 amino acid residues (residue 1 (Met) to residue 33 (Ala) of SEQ ID NO:38), and a mature polypeptide of 146 amino acids (residue 34 (Leu) to residue 179 (Val) of SEQ ID NO:38). ZCYTO18 helix A is defined by amino acid residues 53 to 65 of SEQ ID NO:38; helix B by amino acid residues 92 to 103 of SEQ ID NO:38; helix C by amino acid residues 115 to 124 of SEQ ID NO:38; and helix D by amino acid residues 161 to 174 of SEQ ID NO:38. Four conserved cysteine residues in mouse ZCYTO18 are conserved with the human sequence corresponding to amino acid residues 20, 40, 89; and 132 of SEQ ID NO:38. Moreover, in the mouse sequence alternative starting Methionine residues exist at positions 8 and 13 as shown in SEQ ID NO:38, but the signal peptide cleavage after residue 33 (Ala) would still result in the 146 amino acid mature sequence as described above. The mature sequence for the mouse ZCYTO18 begins at Leu$_{34}$ (as shown in SEQ ID NO:38), which corresponds to Ala$_{22}$ (as shown in SEQ ID NO:3) in the human sequence. There is about 78% identity between the mouse and human sequences over the entire amino acid sequence corresponding to SEQ ID NO:3 and SEQ ID NO:38. The above percent identities were determined using a FASTA program with ktup=1, gap opening penalty=12, gap extension penalty=2, and substitution matrix=BLOSUM62, with other FASTA parameters set as default. The corresponding polynucleotides encoding the mouse ZCYTO18 polypeptide regions, domains, motifs, residues and sequences described above are as shown in SEQ ID NO:37.

Those skilled in the art will recognize that the sequence disclosed in SEQ ID NO:1 represents a single allele of human ZCYTO18 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:3. cDNAs generated from alternatively spliced mRNAs, which retain the properties of the ZCYTO18 polypeptide, are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Moreover, the genomic structure of ZCYTO18 is readily determined by one of skill in the art by comparing the cDNA sequence of SEQ ID NO:1 and the translated amino acid of SEQ ID NO:3 or SEQ ID NO:2 with the genomic DNA in which the gene is contained (e.g, Genbank Accession No. AC007458). For example, such analysis can be readily done using FASTA as described herein. As such, the intron and exon junctions in this region of genomic DNA can be determined for the ZCYTO18 gene. Thus, the present invention includes the ZCYTO18 gene as located in human genomic DNA. Based on annotation of a fragment of human genomic DNA containing a part of ZCYTO18 genomic DNA (Genbank Accession No. AC007458), ZCYTO18 is located at the 12q15 region of chromosome 12.

Within preferred embodiments of the invention, isolated ZCYTO18-encoding nucleic acid molecules can hybridize under stringent conditions to nucleic acid molecules having the nucleotide sequence of SEQ ID NO:1, to nucleic acid molecules having the nucleotide sequence of nucleotides 87 to 587 of SEQ ID NO:1, or to nucleic acid molecules having a nucleotide sequence complementary to SEQ ID NO:1. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1-1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5-25° C. below the $T_m$ of the hybrid and a hybridization buffer having up to 1 M Na$^+$. Higher degrees of stringency at lower temperatures can be achieved with the addition of formamide which reduces the $T_m$ of the hybrid about 1° C. for each 1% formamide in the buffer solution. Generally, such stringent conditions include temperatures of 20-70° C. and a hybridization buffer containing up to 6×SSC and 0-50% formamide. A higher degree of stringency can be achieved at temperatures of from 40-70° C. with a hybridization buffer having up to 4×SSC and from 0-50% formamide. Highly stringent conditions typically encompass temperatures of 42-70° C. with a hybridization buffer having up to 1×SSC and 0-50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide, and it is well within the abilities of one skilled in the art to adapt these conditions for use with a particular polynucleotide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20-25° C. below the calculated $T_m$. For smaller probes, <50 base pairs, hybridization is typically carried out at the $T_m$ or 5-10° C. below the calculated $T_m$. This allows for the maximum rate of hybridization for DNA-DNA and DNA-RNA hybrids.

The length of the polynucleotide sequence influences the rate and stability of hybrid formation. Smaller probe sequences, <50 base pairs, reach equilibrium with complementary sequences rapidly, but may form less stable hybrids. Incubation times of anywhere from minutes to hours can be used to achieve hybrid formation. Longer probe sequences come to equilibrium more slowly, but form more stable complexes, even at lower temperatures. In such cases, incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of a polynucleotide sequence will affect the thermal stability of its hybrid complex, thereby influencing the choice of hybridization temperature and the ionic strength of the hybridization buffer. A-T pairs are less stable than G-C pairs in aqueous solutions containing sodium chloride. Therefore, the higher the G-C content, the more stable the hybrid. Even distribution of G and C residues within the sequence also contributes positively to hybrid stability. In addition, the base pair composition can be manipulated to alter the $T_m$ of a given sequence. For example, 5-methyldeoxycytidine can be substituted for deoxycytidine and 5-bromodeoxuridine can be substituted for thymidine to increase the $T_m$, whereas 7-deazzo-2'-deoxyguanosine can be substituted for guanosine to reduce dependence on $T_m$.

The ionic concentration of the hybridization buffer also affects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a $Na^+$ source, such as SSC (1×SSC: 0.15 M sodium chloride, 15 mM sodium citrate) or SSPE (1×SSPE: 1.8 M NaCl, 10 mM $NaH_2PO_4$, 1 mM EDTA, pH 7.7). By decreasing the ionic concentration of the buffer, the stability of the hybrid is increased. Typically, hybridization buffers contain from between 10 mM-1 M $Na^+$. The addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As an illustration, a nucleic acid molecule encoding a variant ZCYTO18 polypeptide can be hybridized with a nucleic acid molecule having the nucleotide sequence of SEQ ID NO:1 (or its complement) at 42° C. overnight in a solution comprising 50% formamide, 5×SSC (1×SSC: 0.15 M sodium chloride and 15 mM sodium citrate), 50 mM sodium phosphate (pH 7.6), 5×Denhardt's solution (100×Denhardt's solution: 2% (w/v) Ficoll 400, 2% (w/v) polyvinylpyrrolidone, and 2% (w/v) bovine serum albumin), 10% dextran sulfate, and 20 µg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×-2×SSC with 0.1% sodium dodecyl sulfate (SDS) at 55-65° C. That is, nucleic acid molecules encoding a variant ZCYTO18 polypeptide hybridize with a nucleic acid molecule having the nucleotide sequence of SEQ ID NO:1 (or its complement) under stringent washing conditions, in which the wash stringency is equivalent to 0.5×-2× SSC with 0.1% SDS at 55-65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×-0.2×SSC with 0.1% sodium dodecyl sulfate (SDS) at 50-65° C. In other words, nucleic acid molecules encoding a variant ZCYTO18 polypeptide hybridize with a nucleic acid molecule having the nucleotide sequence of SEQ ID NO:1 (or its complement) under highly stringent washing conditions, in which the wash stringency is equivalent to 0.1×-0.2×SSC with 0.1% SDS at 50-65° C., including 0.1×SSC with 0.1% SDS at 50° C., or 0.2×SSC with 0.1% SDS at 65° C.

The present invention also provides isolated ZCYTO18 polypeptides that have a substantially similar sequence identity to the polypeptides of SEQ ID NO:3, or their orthologs. The term "substantially similar sequence identity" is used herein to denote polypeptides comprising at least 70%, at least 80%, at least 90%, at least 95%, or greater than 95% sequence identity to the sequences shown in SEQ ID NO:3, or their orthologs. The present invention also includes polypeptides that comprise an amino acid sequence having at least 70%, at least 80%, at least 90%, at least 95% or greater than 95% sequence identity to the sequence of amino acid residues 1 to 167, or 23 to 167 of SEQ ID NO:3; or amino acid residues 1 to 179, or 35 to 179 of SEQ ID NO:2. The present invention further includes nucleic acid molecules that encode such polypeptides. Methods for determining percent identity are described below.

The present invention also contemplates variant ZCYTO18 nucleic acid molecules that can be identified using two criteria: a determination of the similarity between the encoded polypeptide with the amino acid sequence of SEQ ID NO:3, and/or a hybridization assay, as described above. Such ZCYTO18 variants include nucleic acid molecules: (1) that hybridize with a nucleic acid molecule having the nucleotide sequence of SEQ ID NO:1 (or its complement) under stringent washing conditions, in which the wash stringency is equivalent to 0.5×-2×SSC with 0.1% SDS at 55-65° C.; or (2) that encode a polypeptide having at least 70%, at least 80%, at least 90%, at least 95% or greater than 95% sequence identity to the amino acid sequence of SEQ ID NO:3. Alternatively, ZCYTO18 variants can be characterized as nucleic acid molecules: (1) that hybridize with a nucleic acid molecule having the nucleotide sequence of SEQ ID NO:1 (or its complement) under highly stringent washing conditions, in which the wash stringency is equivalent to 0.1×-0.2×SSC with 0.1% SDS at 50-65° C.; and (2) that encode a polypeptide having at least 70%, at least 80%, at least 90%, at least 95% or greater than 95% sequence identity to the amino acid sequence of SEQ ID NO:3.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes).

$$\frac{\text{Total number of identical matches}}{\begin{bmatrix} \text{length of the longer sequence plus the} \\ \text{number of gaps introduced into the longer} \\ \text{sequence in order to align two sequences} \end{bmatrix}} \times 100$$

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant ZCYTO18. The FASTA algorithm is described by Pearson and Lipman, *Proc. Nat'l Acad. Sci. USA* 85:2444 (1988), and by Pearson, *Meth. Enzmmol.* 183:63 (1990).

Briefly, FASTA first characterizes sequence similarity by identifying regions shared by the query sequence (e.g., SEQ ID NO:3) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzmmol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other FASTA program parameters set as default.

Variant ZCYTO18 polypeptides or polypeptides with substantially similar sequence identity are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20-25 residues, or an affinity tag. The present invention thus includes polypeptides of from about 110 to 180 amino acid residues that comprise a sequence that is at least 70%, preferably at least 90%, and more preferably 95% or more identical to the corresponding region of SEQ ID NO:3. Polypeptides comprising affinity tags can further comprise a proteolytic cleavage site between the ZCYTO18 polypeptide and the affinity tag. Preferred such sites include thrombin cleavage sites and factor Xa cleavage sites.

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Determination of amino acid residues that comprise regions or domains that are critical to maintaining structural integrity can be determined. Within these regions one can determine specific residues that will be more or less tolerant of change and maintain the overall tertiary structure of the molecule. Methods for analyzing sequence structure include, but are not limited to alignment of multiple sequences with high amino acid or nucleotide identity, secondary structure propensities, binary patterns, complementary packing and buried polar interactions (Barton, *Current Opin. Struct. Biol.* 5:372-376, 1995 and Cordes et al., *Current Opin. Struct. Biol.* 6:3-10, 1996). In general, when designing modifications to molecules or identifying specific fragments determination of structure will be accompanied by evaluating activity of modified molecules.

Amino acid sequence changes are made in ZCYTO18 polypeptides so as to minimize disruption of higher order structure essential to biological activity. For example, when the ZCYTO18 polypeptide comprises one or more helices, changes in amino acid residues will be made so as not to disrupt the helix geometry and other components of the molecule where changes in conformation abate some critical function, for example, an active site, or binding of the molecule to its binding partners. The effects of amino acid sequence changes can be predicted by, for example, computer modeling as disclosed above or determined by analysis of crystal structure (see, e.g., Lapthorn et al., *Nat. Struct. Biol.* 2:266-268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216-226, 1992; Gray, *Protein Sci.* 2:1732-1748, 1993; and Patterson et al., *Anal. Chem.* 66:3727-3732, 1994). It is generally believed that if a modified molecule does not have the same cysteine pattern as the standard molecule folding would be affected. Another well known and accepted method for measuring folding is circular dichrosism (CD). Measuring and comparing the CD spectra generated by a modified molecule and standard molecule is routine (Johnson, *Proteins* 7:205-214, 1990). Crystallography is another well known method for analyzing folding and structure. Nuclear magnetic resonance (NMR), digestive peptide mapping and epitope mapping are also known methods for analyzing folding and structurally similarities between proteins and polypeptides (Schaanan et al., *Science* 257:961-964, 1992).

A Hopp/Woods hydrophilicity profile of the ZCYTO18 protein sequence as shown in SEQ ID NO:3 can be generated (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. For example, in ZCYTO18, hydrophilic regions include: (1) amino acid number 29 (Arg) to amino acid number 34 (Asn) of SEQ ID NO:3; (2) amino acid number 121 (His) to amino acid number 126 (Asp) of SEQ ID NO:3; (3) amino acid number 134 (Gln) to amino acid number 139 (Thr) of SEQ ID NO:3; (4) amino acid number 137 (Lys) to amino acid number 142 (Lys) of SEQ ID NO:3; and (5) amino acid number 145 (Glu) to amino acid number 150 (Lys) of SEQ ID NO:2.

Those skilled in the art will recognize that hydrophilicity or hydrophobicity will be taken into account when designing modifications in the amino acid sequence of a ZCYTO18 polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp. For example, residues tolerant of substitution could include such residues as shown in SEQ ID NO:3. Cysteine residues at positions 8, 27, 77 and 120 of SEQ ID NO:3, will be relatively intolerant of substitution.

The identities of essential amino acids can also be inferred from analysis of sequence similarity between IL-10, zcyto10, and MDA7 with ZCYTO18. Using methods such as "FASTA" analysis described previously, regions of high similarity are identified within a family of proteins and used to analyze amino acid sequence for conserved regions. An alternative approach to identifying a variant ZCYTO18 polynucleotide on the basis of structure is to determine whether a nucleic acid molecule encoding a potential variant ZCYTO18 gene can hybridize to a nucleic acid molecule having the nucleotide sequence of SEQ ID NO:1, as discussed above.

Other methods of identifying essential amino acids in the polypeptides of the present invention are procedures known in the art, such as site-directed mutagenesis or alanine-scanning mutagenesis (Cunningham and Wells, *Science* 244:1081 (1989), Bass et al., *Proc. Natl. Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699 (1996).

The present invention also includes functional fragments of ZCYTO18 polypeptides and nucleic acid molecules encoding such functional fragments. A "functional" ZCYTO18 or fragment thereof as defined herein is characterized by its proliferative or differentiating activity, by its ability to induce or inhibit specialized cell functions, or by its ability to bind specifically to an anti-ZCYTO18 antibody, cell, or ZCYTO18 receptor (either soluble or immobilized). As previously described herein, ZCYTO18 is characterized by a four-helical-bundle structure comprising helix A (amino acid residues 41-53), helix B (amino acid residues 80-91), helix C (amino acid residues 103-116) and helix D (amino acid residues 149-162), as shown in SEQ ID NO:3. Thus, the present invention further provides fusion proteins encompassing: (a) polypeptide molecules comprising one or more of the helices described above; and (b) functional fragments comprising one or more of these helices. The other polypeptide portion of the fusion protein may be contributed by another four-helical-bundle cytokine, such as IL-10, zcyto10, MDA7, IL-15, IL-2, IL-4 and GM-CSF, or by a non-native and/or an unrelated secretory signal peptide that facilitates secretion of the fusion protein.

Routine deletion analyses of nucleic acid molecules can be performed to obtain functional fragments of a nucleic acid molecule that encodes a ZCYTO18 polypeptide. As an illustration, DNA molecules having the nucleotide sequence of SEQ ID NO:1 or fragments thereof, can be digested with Bal31 nuclease to obtain a series of nested deletions. These DNA fragments are then inserted into expression vectors in proper reading frame, and the expressed polypeptides are isolated and tested for ZCYTO18 activity, or for the ability to bind anti-ZCYTO18 antibodies or ZCYTO18 receptor. One alternative to exonuclease digestion is to use oligonucleotide-directed mutagenesis to introduce deletions or stop codons to specify production of a desired ZCYTO18 fragment. Alternatively, particular fragments of a ZCYTO18 gene can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993); Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987); Herschman, "The EGF Receptor," in *Control of Animal Cell Proliferation* 1 Boynton et al., (eds.) pages 169-199 (Academic Press 1985); Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995); and Meisel et al., *Plant Molec. Biol.* 30:1 (1996).

Multiple amino acid substitutions can be made and tested using known methods of mutagenesis and screening, such as those disclosed by Reidhaar-Olson and Sauer (*Science* 241: 53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204), and region-directed mutagenesis (Derbyshire et al., *Gene* 46:145 (1986), and Ner et al., DNA 7:127, (1988)).

Variants of the disclosed ZCYTO18 nucleotide and polypeptide sequences can also be generated through DNA shuffling as disclosed by Stemmer, *Nature* 370:389 (1994), Stemmer, *Proc. Natl. Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-ZCYTO18 antibodies or soluble ZCYTO18 receptor, can be recovered from the host cells and rapidly sequenced using modern equipment. These methods allow the rapid determination of the importance of individual amino acid residues in a polypeptide of interest, and can be applied to polypeptides of unknown structure.

In addition, the proteins of the present invention (or polypeptide fragments thereof) can be joined to other bioactive molecules, particularly other cytokines, to provide multifunctional molecules. For example, one or more helices from ZCYTO18 can be joined to other cytokines to enhance their biological properties or efficiency of production.

The present invention thus provides a series of novel, hybrid molecules in which a segment comprising one or more of the helices of ZCYTO18 is fused to another polypeptide. Fusion is preferably done by splicing at the DNA level to allow expression of chimeric molecules in recombinant production systems. The resultant molecules are then assayed for such properties as improved solubility, improved stability, prolonged clearance half-life, improved expression and secretion levels, and pharmacodynamics. Such hybrid molecules may further comprise additional amino acid residues (e.g. a polypeptide linker) between the component proteins or polypeptides.

Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tent-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202: 301 (1991), Chung et al., *Science* 259:806 (1993), and Chung et al., *Proc. Nat'l Acad. Sci. USA* 90:10145 (1993).

In a second method, translation is carried out in *Xenopus* oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for ZCYTO18 amino acid residues.

The present invention also provides polypeptide fragments or peptides comprising an epitope-bearing portion of a ZCYTO18 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein. Hopp/Woods hydrophilicity profiles can be used to determine regions that have the most antigenic potential (Hopp et al., 1981, *ibid.* and Hopp, 1986, *ibid.*). In ZCYTO18 these regions include: (1) amino acid number 29 (Arg) to amino acid number 34 (Asn) of SEQ ID NO:3; (2) amino acid number 121 (His) to amino acid number 126 (Asp) of SEQ ID NO:3; (3) amino acid number 134 (Gln) to amino acid number 139 (Thr) of SEQ ID NO:3; (4) amino acid number 137 (Lys) to amino acid number 142 (Lys) of SEQ ID NO:3; and (5) amino acid number 145 (Glu) to amino acid number 150 (Lys) of SEQ ID NO:2. Moreover, ZCYTO18 antigenic epitopes as predicted by a Jameson-Wolf plot, e.g., using DNASTAR Protean program (DNASTAR, Inc., Madison, Wis.) serve as preferred antigens, and are readily determined by one of skill in the art.

Antigenic epitope-bearing peptides and polypeptides preferably contain at least four to ten amino acids, at least ten to fifteen amino acids, or about 15 to about 30 amino acids of SEQ ID NO:3. Such epitope-bearing peptides and polypeptides can be produced by fragmenting a ZCYTO18 polypeptide, or by chemical peptide synthesis, as described herein. Moreover, epitopes can be selected by phage display of random peptide libraries (see, for example, Lane and Stephen, *Curr. Opin. Immunol* 5:268 (1993); and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105-116 (The Humana Press, Inc. 1992); Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.), *Current Protocols in Immunology*, pages 9.3.1-9.3.5 and pages 9.4.1-9.4.11 (John Wiley & Sons 1997).

Regardless of the particular nucleotide sequence of a variant ZCYTO18 polynucleotide, the polynucleotide encodes a polypeptide that is characterized by its proliferative or differentiating activity, its ability to induce or inhibit specialized cell functions, or by the ability to bind specifically to an anti-ZCYTO18 antibody or ZCYTO18 receptor. More specifically, variant ZCYTO18 polynucleotides will encode polypeptides which exhibit at least 50% and preferably, greater than 70%, 80% or 90%, of the activity of the polypeptide as shown in SEQ ID NO:3.

For any ZCYTO18 polypeptide, including variants and fusion proteins, one of ordinary skill in the art can readily generate a fully degenerate polynucleotide sequence encoding that variant using the information set forth in Tables 1 and 2 above.

The present invention further provides a variety of other polypeptide fusions (and related multimeric proteins comprising one or more polypeptide fusions). For example, a ZCYTO18 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-ZCYTO18 polypeptide fusions can be expressed in genetically engineered cells (to produce a variety of multimeric ZCYTO18 analogs). Auxiliary domains can be fused to ZCYTO18 polypeptides to target them to specific cells, tissues, or macromolecules. For example, a ZCYTO18 polypeptide or protein could be targeted to a predetermined cell type by fusing a ZCYTO18 polypeptide to a ligand that specifically binds to a receptor on the surface of that target cell. In this way, polypeptides and proteins can be targeted for therapeutic or diagnostic purposes. A ZCYTO18 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996.

Using the methods discussed herein, one of ordinary skill in the art can identify and/or prepare a variety of polypeptides that have substantially similar sequence identity to amino acid residues 1-167 or 23-167 of SEQ ID NO:3, or functional fragments and fusions thereof, wherein such polypeptides or fragments or fusions retain the properties of the wild-type protein such as the ability to stimulate proliferation, differentiation, induce specialized cell function or bind the ZCYTO18 receptor or ZCYTO18 antibodies.

The ZCYTO18 polypeptides of the present invention, including full-length polypeptides, functional fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a ZCYTO18 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a ZCYTO18 polypeptide into the secretory pathway of a host cell, a secretory signal sequence (also known as a leader sequence, prepro sequence or pre sequence) is provided in the expression vector. The secretory signal sequence may be that of ZCYTO18, or may be derived from another secreted protein (e.g., t-PA) or synthesized de novo. The secretory signal sequence is operably linked to the ZCYTO18 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence comprising amino acid residue 1 (Met) to 21 (Ala)

of SEQ ID NO:3 is be operably linked to a DNA sequence encoding another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-5, 1982), DEAE-dextran mediated transfection (Ausubel et al., *ibid.*), and liposome-mediated transfection (Hawley-Nelson et al., *Focus* 15:73, 1993; Ciccarone et al., *Focus* 15:80, 1993, and viral vectors (Miller and Rosman, *BioTechniques* 7:980-90, 1989; Wang and Finer, *Nature Med.* 2:714-6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N. J., Humana Press, 1995. The second method of making recombinant baculovirus utilizes a transposon-based system described by Luckow (Luckow, V. A, et al., *J Virol* 67:4566-79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the ZCYTO18 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case ZCYTO18. However, pFastBac 1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J. Gen. Virol.* 71:971-6, 1990; Bonning, B. C. et al., *J. Gen. Virol.* 75:1551-6, 1994; and, Chazenbalk, G. D., and Rapoport, B., *J. Biol. Chem.* 270:1543-9, 1995. In such transfer vector constructs, a short or long version of the basic protein promoter can be used. Moreover, transfer vectors can be constructed which replace the native ZCYTO18 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native ZCYTO18 secretory signal sequence. In addition, transfer vectors can include an in-frame fusion with DNA encoding an epitope tag at the C- or N-terminus of the expressed ZCYTO18 polypeptide, for example, a Glu-Glu epitope tag (Grussenmeyer, T. et al., *Proc. Natl. Acad. Sci.* 82:7952-4, 1985). Using techniques known in the art, a transfer vector containing ZCYTO18 is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses ZCYTO18 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3. Procedures used are generally described in available laboratory manuals (King, L. A. and Possee, R. D., ibid.; O'Reilly, D. R. et al., *ibid.*; Richardson, C. D., *ibid.*). Subsequent purification of the ZCYTO18 polypeptide from the supernatant can be achieved using methods described herein.

Fungal cells, including yeast cells, can also be used within the present invention. Yeast species of particular interest in this regard include *Saccharomyces cerevisiae, Pichia pastoris,* and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago* maydis, *Pichia pastoris, Pichia methanolica, Pichia guillermondii* and *Candida maltosa* are known in the art. See, for example, Gleeson et al., *J. Gen. Microbiol.* 132:3459-65, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., *ibid.*). When expressing a ZCYTO18 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

It is preferred to purify the polypeptides of the present invention to $\geq 80\%$ purity, more preferably to $\geq 90\%$ purity, even more preferably $\geq 95\%$ purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant ZCYTO18 polypeptides (or chimeric ZCYTO18 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their physical properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1-7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp. 529-39) and use of the soluble ZCYTO18 receptor. Within additional embodiments of the invention, a fusion of the polypeptide of interest and an affinity tag (e.g., maltose-binding protein, an immunoglobulin domain) may be constructed to facilitate purification.

Moreover, using methods described in the art, polypeptide fusions, or hybrid ZCYTO18 proteins, are constructed using regions or domains of the inventive ZCYTO18 in combination with those of other human cytokine family proteins (e.g. interleukins or GM-CSF), or heterologous proteins (Sambrook et al., *ibid*., Altschul et al., ibid., Picard, *Cur. Opin. Biology,* 5:511-5, 1994, and references therein). These methods allow the determination of the biological importance of larger domains or regions in a polypeptide of interest. Such hybrids may alter reaction kinetics, binding, alter cell proliferative activity, constrict or expand the substrate specificity, or alter tissue and cellular localization of a polypeptide, and can be applied to polypeptides of unknown structure.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a helix conferring a biological function may be swapped between ZCYTO18 of the present invention with the functionally equivalent helices from another family member, such as IL-10, zcyto10, MDA7, IL-15, IL-2, IL-4 and GM-CSF. Such components include, but are not limited to, the secretory signal sequence, helices A, B, C, D and four-helical-bundle cytokines. Such fusion proteins would be expected to have a biological functional profile that is the same or similar to polypeptides of the present invention or other known four-helical-bundle cytokine family proteins, depending on the fusion constructed. Moreover, such fusion proteins may exhibit other properties as disclosed herein.

Standard molecular biological and cloning techniques can be used to swap the equivalent domains between the ZCYTO18 polypeptide and those polypeptides to which they are fused. Generally, a DNA segment that encodes a domain of interest, e.g., ZCYTO18 helices A through D, or other domain described herein, is operably linked in frame to at least one other DNA segment encoding an additional polypeptide (for instance a domain or region from another cytokine, such as IL-10, or zcyto10, MDA7 or the like), and inserted into an appropriate expression vector, as described herein. Generally DNA constructs are made such that the several DNA segments that encode the corresponding regions of a polypeptide are operably linked in frame to make a single construct that encodes the entire fusion protein, or a functional portion thereof. For example, a DNA construct would encode from N-terminus to C-terminus a fusion protein comprising a signal polypeptide followed by a mature four helical bundle cytokine fusion protein containing helix A, followed by helix B, followed by helix C, followed by helix D. or for example, any of the above as interchanged with equivalent regions from another four helical bundle cytokine family protein. Such fusion proteins can be expressed, isolated, and assayed for activity as described herein. Moreover, such fusion proteins can be used to express and secrete fragments of the ZCYTO18 polypeptide, to be used, for example to inoculate an animal to generate anti-ZCYTO18 antibodies as described herein. For example a secretory signal sequence can be operably linked to helix A, B, C or D, or a combination thereof (e.g., operably linked polypeptides comprising helices A-B, B-C, C-D, A-C, A-D, B-D, or ZCYTO18 polypeptide fragments described herein), to secrete a fragment of ZCYTO18 polypeptide that can be purified as described herein and serve as an antigen to be inoculated into an animal to produce anti-ZCYTO18 antibodies, as described herein.

Zcyto18 polypeptides or fragments thereof may also be prepared through chemical synthesis. ZCYTO18 polypeptides may be monomers or multimers; glycosylated or non-glycosylated; pegylated or non-pegylated; and may or may not include an initial methionine amino acid residue. For example, the polypeptides can be prepared by solid phase peptide synthesis, for example as described by Merrifield, *J. Am. Chem. Soc.* 85:2149, 1963.

The activity of molecules of the present invention can be measured using a variety of assays that measure proliferation of and/or binding to cells expressing the ZCYTO18 receptor. Of particular interest are changes in ZCYTO18-dependent cells. Suitable cell lines to be engineered to be ZCYTO18-dependent include the IL-3-dependent BaF3 cell line (Palacios and Steinmetz, *Cell* 41: 727-734, 1985; Mathey-Prevot et al., *Mol. Cell. Biol.* 6: 4133-4135, 1986), FDC-P1 (Hapel et al., Blood 64: 786-790, 1984), and MO7e (Kiss et al., *Leuke-* mia 7: 235-240, 1993). Growth factor-dependent cell lines can be established according to published methods (e.g. Greenberger et al., *Leukemia Res.* 8: 363-375, 1984; Dexter et al., in Baum et al. Eds., *Experimental Hematology Today,* 8th Ann. Mtg. Int. Soc. Exp. Hematol. 1979, 145-156, 1980). For example, Baf3 cells expressing the ZCYTO18 heterodimeric receptor zcytor11/CRF2-4, as described herein, can be used to assay the activity of ZCYTO18, ZCYTO18 receptor-binding fragments, and ZCYTO18 variants of the present invention. The BaF3 stable cell line that co-expressing zcytor11 and CRF2-4 (ZCYTO18 receptor) exhibits dose-dependent proliferative response to ZCYTO18 protein in the media without IL-3.

Proteins of the present invention are useful for stimulating proliferation, activation, differentiation and/or induction or inhibition of specialized cell function of cells of the involved homeostasis of the hematopoiesis and immune function. In particular, ZCYTO18 polypeptides are useful for stimulating proliferation, activation, differentiation, induction or inhibition of specialized cell functions of cells of the hematopoetic lineages, including, but not limited to, T cells, B cells, NK cells, dendritic cells, monocytes, and macrophages. Proliferation and/or differentiation of hematopoietic cells can be measured in vitro using cultured cells or in vivo by administering molecules of the present invention to the appropriate animal model. Assays measuring cell proliferation or differentiation are well known in the art. For example, assays measuring proliferation include such assays as chemosensitivity to neutral red dye (Cavanaugh et al., *Investigational New Drugs* 8:347-354, 1990, incorporated herein by reference), incorporation of radiolabelled nucleotides (Cook et al., *Analytical Biochem.* 179:1-7, 1989, incorporated herein by reference), incorporation of 5-bromo-2'-deoxyuridine (BrdU) in the DNA of proliferating cells (Porstmann et al., *J. Immunol. Methods* 82:169-179, 1985, incorporated herein by reference), and use of tetrazolium salts (Mosmann, *J. Immunol. Methods* 65:55-63, 1983; Alley et al., *Cancer Res.* 48:589-601, 1988; Marshall et al., *Growth Reg.* 5:69-84, 1995; and Scudiero et al., *Cancer Res.* 48:4827-4833, 1988; all incorporated herein by reference). Assays measuring differentiation include, for example, measuring cell-surface markers associated with stage-specific expression of a tissue, enzymatic activity, functional activity or morphological changes (Watt, *FASEB,* 5:281-284, 1991; Francis, *Differentiation* 57:63-75, 1994; Raes, *Adv. Anim. Cell Biol. Technol. Bioprocesses,* 161-171, 1989; all incorporated herein by reference).

IL-10 is a cytokine that inhibits production of other cytokines, induces proliferation and differentiation of activated B lymphocytes, inhibits HIV-1 replication and exhibits antagonistic effects on gamma interferon. IL-10 appears to exist as a dimer formed from two alpha-helical polypeptide regions related by a 180° rotation. See, for example, Zdanov et al., *Structure:* 3(6): 591-601 (1996). IL-10 has been reported to be a product of activated Th2 T-cells, B-cells, keratinocytes and monocytes/macrophages that is capable of modulating a Th1 T-cell response. Such modulation may be accomplished by inhibiting cytokine synthesis by Th1 T-cells. See, for example, Hus et al., *Int. Immunol.* 4: 563 (1992) and D'Andrea et al., *J. Exp. Med.* 178: 1042 (1992). IL-10 has also been reported to inhibit cytokine synthesis by natural killer cells and monocytes/macrophages. See, for example, Hus et al. cited above and Fiorentino et al., *J. Immunol.* 146: 3444 (1991). In addition, IL-10 has been found to have a protective effect with respect to insulin dependent diabetes mellitus. Similarly, as a cytokine sharing polypeptide structure and some sequence similarity to IL-10, ZCYTO18 can have these above disclosed activities, and the assays used to assess IL-10 activity can be applied to assay ZCYTO18 activity.

The molecules of the present invention can be assayed in vivo using viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acid (for review, see T. C. Becker et al., *Meth. Cell Biol.* 43:161-89, 1994; and J. T. Douglas and D. T. Curiel, *Science & Medicine* 4:44-53, 1997). The adenovirus system offers several advantages: (i) adenovirus can accommodate relatively large DNA inserts; (ii) can be grown to high-titer; (iii) infect a broad range of mammalian cell types; and (iv) can be used with many different promoters including ubiquitous, tissue specific, and regulatable promoters. Also, because adenoviruses are stable in the bloodstream, they can be administered by intravenous injection.

Using adenovirus vectors where portions of the adenovirus genome are deleted, inserts are incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol.* 72:2022-2032, 1998; Raper, S. E. et al., *Human Gene Therapy* 9:671-679, 1998). In addition, deletion of E2b is reported to reduce immune responses (Amalfitano, A. et al., *J. Virol.* 72:926-933, 1998). Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J.* 11:615-623, 1997.

The adenovirus system can also be used for protein production in vitro. By culturing adenovirus-infected cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293 cells can be grown as adherent cells or in suspension culture at relatively high cell density to produce significant amounts of protein (See Garnier et al., *Cytotechnol.* 15:145-55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins may also be effectively obtained.

In view of the tissue distribution observed for ZCYTO18 receptor agonists (including the natural ligand/substrate/cofactor/etc.) and/or antagonists have enormous potential in both in vitro and in vivo applications. Compounds identified as ZCYTO18 agonists are useful for expansion, proliferation, activation, differentiation, and/or induction or inhibition of specialized cell functions of cells involved in homeostasis of hematopoiesis and immune function. For example, ZCYTO18 and agonist compounds are useful as components of defined cell culture media, and may be used alone or in combination with other cytokines and hormones to replace serum that is commonly used in cell culture. Agonists are thus useful in specifically promoting the growth and/or development of T-cells, B-cells, and other cells of the lymphoid and myeloid lineages in culture.

Antagonists are also useful as research reagents for characterizing sites of ligand-receptor interaction. Antagonists are useful to inhibit expansion, proliferation, activation, and/or differentiation of cells involved in regulating hematopoiesis. Inhibitors of ZCYTO18 activity (ZCYTO18 antagonists) include anti-ZCYTO18 antibodies and soluble ZCYTO18 receptors, as well as other peptidic and non-peptidic agents (including ribozymes).

ZCYTO18 can also be used to identify inhibitors (antagonists) of its activity. Test compounds are added to the assays disclosed herein to identify compounds that inhibit the activity of ZCYTO18. In addition to those assays disclosed herein, samples can be tested for inhibition of ZCYTO18 activity within a variety of assays designed to measure receptor binding, the stimulation/inhibition of ZCYTO18-dependent cellular responses or proliferation of ZCYTO18 receptor-expressing cells.

A ZCYTO18 polypeptide can be expressed as a fusion with an immunoglobulin heavy chain constant region, typically an $F_C$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the Fc portions are disulfide bonded to each other and two non-Ig polypeptides are arrayed in closed proximity to each other. Fusions of this type can be used to (e.g., for dimerization, increasing stability and in vivo half-life, affinity purify ligand, in vitro assay tool, antagonist). For use in assays, the chimeras are bound to a support via the $F_C$ region and used in an ELISA format. Fc fusions may represent preferred therapeutic proteins with different pharmacokinetics and altered action.

Polypeptides containing the receptor-binding region of the ligand can be used for purification of receptor. The ligand polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting media will generally be configured in the form of a column, and fluids containing receptors are passed through the column one or more times to allow receptor to bind to the ligand polypeptide. The receptor is then eluted using changes in salt concentration, chaotropic agents ($MnCl_2$), or pH to disrupt ligand-receptor binding.

ZCYTO18 polypeptides or ZCYTO18 fusion proteins are used, for example, to identify the ZCYTO18 receptor. Using labeled ZCYTO18 polypeptides, cells expressing the receptor are identified by fluorescence immunocytometry or immunohistochemistry. ZCYTO18 polypeptides are useful in determining the distribution of the receptor on tissues or specific cell lineages, and to provide insight into receptor/ligand biology. An exemplary method to identify a ZCYTO18 receptor in vivo or in vitro, e.g., in cell lines, is to us a ZCYTO18 polypeptide fused to the catalytic domain of Alkaline phosphatase (AP), as described in Feiner, L. et al., *Neuron* 19:539-545, 1997. Such AP fusions, as well as radiolabeled ZCYTO18, ZCYTO18 fusions with fluorescent lables, and others described herein, combined with standard cloning techniques enable one of skill in the art to visualize, identify and clone the ZCYTO18 receptor.

Conversely, a ZCYTO18-binding polypeptide can be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229-40, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding. Alternatively, ligand/receptor binding can be analyzed using SELDI™ technology (Ciphergen, Inc., Palo Alto, Calif.).

Ligand-binding receptor polypeptides can also be used within other assay systems known in the art. Such systems include Scatchard analysis for determination of binding affinity (see Scatchard, *Ann. NY Acad. Sci.* 51: 660-72, 1949) and calorimetric assays (Cunningham et al., *Science* 253:545-48, 1991; Cunningham et al., *Science* 245:821-25, 1991).

Zcyto18 polypeptides can also be used to prepare antibodies that bind to ZCYTO18 epitopes, peptides or polypeptides. The ZCYTO18 polypeptide or a fragment thereof serves as an antigen (immunogen) to inoculate an animal and elicit an immune response. One of skill in the art would recognize that antigenic, epitope-bearing polypeptides contain a sequence of at least 6, preferably at least 9, and more preferably at least 15 to about 30 contiguous amino acid residues of a ZCYTO18 polypeptide (e.g., SEQ ID NO:3). Polypeptides comprising a larger portion of a ZCYTO18 polypeptide, i.e., from 30 to 100 residues up to the entire length of the amino acid sequence are included. Antigens or immunogenic epitopes can also include attached tags, adjuvants and carriers, as described herein. Suitable antigens include the ZCYTO18 polypeptide encoded by SEQ ID NO:3 from amino acid number 23 to amino acid number 167, or a contiguous 9 to 144, or 30 to 144 amino acid fragment thereof. Other suitable antigens include helices of the four-helical-bundle structure, as described herein. Preferred peptides to use as antigens are hydrophilic peptides such as those predicted by one of skill in the art from a hydrophobicity plot, as described herein. For example suitable hydrophilic peptides include: (1) amino acid number 29 (Arg) to amino acid number 34 (Asn) of SEQ ID NO:3; (2) amino acid number 121 (His) to amino acid number 126 (Asp) of SEQ ID NO:3; (3) amino acid number 134 (Gln) to amino acid number 139 (Thr) of SEQ ID NO:3; (4) amino acid number 137 (Lys) to amino acid number 142 (Lys) of SEQ ID NO:3; and (5) amino acid number 145 (Glu) to amino acid number 150 (Lys) of SEQ ID NO:2. Moreover, ZCYTO18 antigenic epitopes as predicted by a Jameson-Wolf plot, e.g., using DNASTAR Protean program (DNASTAR, Inc., Madison, Wis.) serve as preferred antigens, and are readily determined by one of skill in the art.

Antibodies from an immune response generated by inoculation of an animal with these antigens (or immunogens) can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a ZCYTO18 polypeptide or a fragment thereof. The immunogenicity of a ZCYTO18 polypeptide may be increased through the use of an adjuvant, such as alum (aluminum hydroxide) or Freund's complete or incomplete adjuvant. Polypeptides useful for immunization also include fusion polypeptides, such as fusions of ZCYTO18 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

Antibodies are considered to be specifically binding if: 1) they exhibit a threshold level of binding activity, and 2) they do not significantly cross-react with related polypeptide molecules. A threshold level of binding is determined if anti-ZCYTO18 antibodies herein bind to a ZCYTO18 polypeptide, peptide or epitope with an affinity at least 10-fold greater than the binding affinity to control (non-ZCYTO18) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660-672, 1949).

Whether anti-ZCYTO18 antibodies do not significantly cross-react with related polypeptide molecules is shown, for example, by the antibody detecting ZCYTO18 polypeptide but not known related polypeptides using a standard Western blot analysis (Ausubel et al., ibid.). Examples of known related polypeptides are those disclosed in the prior art, such as known orthologs, and paralogs, and similar known members of a protein family. Screening can also be done using non-human ZCYTO18, and ZCYTO18 mutant polypeptides. Moreover, antibodies can be "screened against" known related polypeptides, to isolate a population that specifically binds to the ZCYTO18 polypeptides. For example, antibodies raised to ZCYTO18 are adsorbed to related polypeptides adhered to insoluble matrix; antibodies specific to ZCYTO18 will flow through the matrix under the proper buffer conditions. Screening allows isolation of polyclonal and monoclonal antibodies non-crossreactive to known closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1-98, 1988; *Monoclonal Antibodies: Principles and Practice*, Goding, J. W. (eds.), Academic Press Ltd., 1996; Benjamin et al., *Ann. Rev. Immunol* 2: 67-101, 1984. Specifically binding anti-ZCYTO18 antibodies can be detected by a number of methods in the art, and disclosed below.

A variety of assays known to those skilled in the art can be utilized to detect antibodies which bind to ZCYTO18 proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant ZCYTO18 protein or polypeptide.

Alternative techniques for generating or selecting antibodies useful herein include in vitro exposure of lymphocytes to ZCYTO18 protein or peptide, and selection of antibody display libraries in phage or similar vectors (for instance, through use of immobilized or labeled ZCYTO18 protein or peptide). Genes encoding polypeptides having potential ZCYTO18 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the ZCYTO18 sequences disclosed herein to identify proteins which bind to ZCYTO18. These "binding polypeptides" which interact with ZCYTO18 polypeptides can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and neutralizing activity, e.g., for blocking interaction between ligand and receptor, or viral binding to a receptor. The binding polypeptides can also be used for diagnostic assays for determining circulating levels of ZCYTO18 polypeptides; for detecting or quantitating soluble ZCYTO18 polypeptides as marker of underlying pathology or disease. These binding polypeptides can also act as ZCYTO18 "antagonists" to block ZCYTO18 binding and signal transduction in vitro and in vivo. These anti-ZCYTO18 binding polypeptides would be useful for inhibiting ZCYTO18 activity or protein-binding.

Antibodies to ZCYTO18 may be used for tagging cells that express ZCYTO18; for isolating ZCYTO18 by affinity purification; for diagnostic assays for determining circulating levels of ZCYTO18 polypeptides; for detecting or quantitating soluble ZCYTO18 as a marker of underlying pathology or disease; in analytical methods employing FACS; for screening expression libraries; for generating anti-idiotypic antibodies; and as neutralizing antibodies or as antagonists to block ZCYTO18 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to ZCYTO18 or fragments thereof may be used in vitro to detect denatured ZCYTO18 or fragments thereof in assays, for example, Western Blots or other assays known in the art.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, ZCYTO18 polypeptides or anti-ZCYTO18 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a receptor binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates. Such cytokine toxin fusion proteins can be used for in vivo killing of target tissues.

In another embodiment, ZCYTO18 cytokine fusion proteins or antibody-cytokine fusion proteins can be used for in vivo killing of target tissues (for example, leukemia, lymphoma, lung cancer, colon cancer, melanoma, pancreatic cancer, ovanian cancer, blood and bone marrow cancers, or other cancers wherein ZCYTO18 receptors ar expressed) (See, generally, Hornick et al., Blood 89:4437-47, 1997). The described fusion proteins enable targeting of a cytokine to a desired site of action, thereby providing an elevated local concentration of cytokine. Suitable ZCYTO18 polypeptides or anti-ZCYTO18 antibodies target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

In yet another embodiment, if the ZCYTO18 polypeptide or anti-ZCYTO18 antibody targets vascular cells or tissues, such polypeptide or antibody may be conjugated with a radionuclide, and particularly with a beta-emitting radionuclide, to reduce restenosis. Such therapeutic approaches pose less danger to clinicians who administer the radioactive therapy. For instance, iridium-192 impregnated ribbons placed into stented vessels of patients until the required radiation dose was delivered showed decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide or antibody conjugates described herein can be delivered intravenously, intraarterially or intraductally, or may be introduced locally at the intended site of action.

Zcyto18 was isolated from tissue known to have important immunological function and which contain cells which play a role in the immune system. ZCYTO18 ligand is expressed in CD3+ selected, activated peripheral blood cells. This suggests that ZCYTO18 expression may be regulated and increase after T cell activation. Moreover, polypeptides of the present invention may have an effect on the growth/expansion and/or differentiated state of T- or B-Cells, T- or B-cell progenitors, NK cells or NK progenitors. Moreover, ZCYTO18 can effect proliferation and/or differentiation of T cells and B cells in vivo. Factor that both stimulate proliferation of hematopoietic progenitors and activate mature cells are generally known. NK cells are responsive to IL-2 alone, but proliferation and activation generally require additional growth factors. For example, it has been shown that IL-7 and Steel Factor (c-kit ligand) were required for colony formation of NK progenitors. IL-15+IL-2 in combination with IL-7 and Steel Factor was more effective (Mrózek et al., Blood 87:2632-2640, 1996). However, unidentified cytokines may be necessary for proliferation of specific subsets of NK cells and/or NK progenitors (Robertson et. al., Blood 76:2451-2438, 1990). A composition comprising ZCYTO18 and IL-15 may stimulate NK progenitors and NK cells, as a composition that is more potent than previously described factors and combinations of factors. Similarly, such combinations of factors that include ZCYTO18 may also affect other hematopoietic and lymphoid cell types, such as T-cells, B-cells, macrophages, dendritic cells, and the like.

Most four-helix bundle cytokines as well as other proteins produced by activated lymphocytes play an important biological role in cell differentiation, activation, recruitment and homeostasis of cells throughout the body. Therapeutic utility includes treatment of diseases which require immune regulation including autoimmune diseases, such as, rheumatoid arthritis, multiple sclerosis, myasthenia gravis, systemic lupus erythomatosis (SLE) and diabetes. Zcyto18 may be important in the regulation of inflammation, and therefore would be useful in treating rheumatoid arthritis, asthma, ulcerative colitis, inflammatory bowel disease, Crohn's disease, pancreatitis, and sepsis. There may be a role of ZCYTO18 in mediating tumor cell killing and therefore would be useful in the treatment of cancer such as ovarian cancer, lung cancer, melanoma, and colon cancer. Zcyto18 may be a potential therapeutic in suppressing the immune system which would be important for reducing graft rejection. Zcyto18 may have usefulness in prevention of graft-vs-host disease.

The proteins of the present invention can also be used ex vivo, such as in autologous marrow culture. Briefly, bone marrow is removed from a patient prior to chemotherapy or organ transplant and treated with ZCYTO18, optionally in combination with one or more other cytokines. The treated marrow is then returned to the patient after chemotherapy to speed the recovery of the marrow or after transplant to suppress graft vs. Host disease. In addition, the proteins of the present invention can also be used for the ex vivo expansion of marrow or peripheral blood progenitor (PBPC) cells. Prior to treatment, marrow can be stimulated with stem cell factor (SCF) to release early progenitor cells into peripheral circulation. These progenitors can be collected and concentrated from peripheral blood and then treated in culture with ZCYTO18, optionally in combination with one or more other cytokines, including but not limited to IL-10, zcyto10, MDA7, SCF, IL-2, IL-4, IL-7 or IL-15, to differentiate and proliferate into high-density lymphoid cultures, which can then be returned to the patient following chemotherapy or transplantation.

Alternatively, ZCYTO18 may activate the immune system which would be important in boosting immunity to infectious diseases, treating immunocompromised patients, such as HIV+patients, or in improving vaccines. In particular, ZCYTO18 stimulation or expansion of T-cells, B-cells, NK cells, and the like, or their progenitors, would provide therapeutic value in treatment of viral infection, and as an antineoplastic factor. NK cells are thought to play a major role in elimination of metastatic tumor cells and patients with both metastases and solid tumors have decreased levels of NK cell activity (Whiteside et. al., *Curr. Top. Microbiol. Immunol* 230:221-244, 1998).

Further analysis of mice injected with ZCYTO18 adenovirus reveals that albumin levels are reduced relative to control adenovirus injected animals, and glucose levels are depressed significantly. However liver enzymes (ALT and AST) are at similar levels to those seen for mice injected with control adenovirus. ZCYTO18 may specifically inhibit or alter liver cell functions. Alternatively excess ZCYTO18 may synergize with viral infection leading to adverse effects on the liver. Thus antagonists (antibodies, muteins, soluble receptors) may be useful to treat viral disease. Especially viral diseases that target the liver such as: Hepatitis B, Hepatitis C and Adenovirus. Viral disease in other tissues may be treated with antagonists to ZCYTO18, for example viral meningitis, and HIV-related disease.

Mice injected with ZCYTO18 adenovirus display weight-loss, loss of mobility and a failure to groom, and a reduction in circulating lymphocytes. These changes are typical of those seen during septic shock and other inflammatory conditions. These effects may be caused directly by ZCYTO18 or indirectly by induction of elevated levels of proinflammatory cytokines such as IL-1, TNFα, and IL-6. Antagonists to ZCYTO18 may be useful to treat septic shock, adult respiratory distress syndrome, endotoxemia, and meningitis. Other diseases that may benefit from ZCYTO18 antagonists include: Hemorrhagic shock, disseminated intravascular coagulopathy, myocardial ischemia, stroke, rejection of transplanted organs, pulmonary fibrosis, inflammatory hyperalgesia and cachexia.

Mice injected with ZCYTO18 adenovirus display reduced numbers of peripheral blood lymphocytes. This is likely to be a direct inhibitory effect of ZCYTO18 on peripheral blood lymphocytes. Antagonizing ZCYTO18 may promote lymphocyte maintenance and growth especially when they are needed to eradicate bacterial, viral or parasitic pathogens. Thus antagonizing ZCYTO18 may benefit patients with: Tuberculosis, cryptogenic fibrosing alveolitis, pneumonia, meningococcal disease, AIDS, HIV-related lung disease, hepatitis, viral meningitis, malaria, and dysentery (*Shigella dysenteriae*).

The lymphocyte inhibitory effects of ZCYTO18 may be used to reduce autoimmunity and to inhibit the growth of lymphoma tumors, especially non-Hodgkin's lymphoma and lymphoid leukemias. ZCYTO18 may also be used to inhibit lymphocytes and promote graft acceptance for organ transplant patients. Kidney and bone marrow grafts would be suitable indications.

Mice injected with ZCYTO18 adenovirus display significantly increased numbers of platelets. Mild bleeding disorders (MBDs) associated with platelet dysfunctions are relatively common (Bachmann, *Seminars in Hematology* 17: 292-305, 1980), as are a number of congenital disorders of platelet function, including Bernard-Soulier syndrome (deficiency in platelet GPIb), Glanzmann's thrombasthenia (deficiency of GPIIb and GPIIIa), congenital afibrinogenemia (diminished or absent levels of fibrinogen in plasma and platelets), and gray platelet syndrome (absence of a-granules). In addition there are a number of disorders associated with platelet secretion, storage pool deficiency, abnormalities in platelet arachidonic acid pathway, deficiencies of platelet cyclooxygenase and thromboxane synthetase and defects in platelet activation (reviewed by Rao and Holmsen, *Seminars in Hematology* 23: 102-118, 1986).

The proteins of the present invention were shown to increase platelet and neutrophils in vivo in animals, and can be used therapeutically wherever it is desirable to increase the level of platelets and neutrophils, such as in the treatment of cytopenia, such as that induced by aplastic anemia, myelodisplastic syndromes, chemotherapy or congenital cytopenias. The proteins are also useful for increasing platelet production, such as in the treatment of thrombocytopenia. Thrombocytopenia is associated with a diverse group of diseases and clinical situations that may act alone or in concert to produce the condition. Lowered platelet counts can result from, for example, defects in platelet production, abnormal platelet distribution, dilutional losses due to massive transfusions, or abnormal destruction of platelets. For example, chemotherapeutic drugs used in cancer therapy may suppress development of platelet progenitor cells in the bone marrow, and the resulting thrombocytopenia limits the chemotherapy and may necessitate transfusions. In addition, certain malignancies can impair platelet production and platelet distribution. Radiation therapy used to kill malignant cells also kills platelet progenitor cells. Thrombocytopenia may also arise from various platelet autoimmune disorders induced by drugs, neonatal alloimmunity or platelet transfusion alloimmunity. The proteins of the present invention can reduce or eliminate the need for transfusions, thereby reducing the incidence of platelet alloimmunity. Abnormal destruction of platelets can result from: (1) increased platelet consumption in vascular grafts or traumatized tissue; or (2) immune mechanisms associated with, for example, drug-induced thrombocytopenia, idiopathic thrombocytopenic purpura (ITP), autoimmune diseases, hematologic disorders such as leukemia and lymphoma or metastatic cancers involving bone marrow. Other indications for the proteins of the present invention include aplastic anemia and drug-induced marrow suppression resulting from, for example, chemotherapy or treatment of HIV infection with AZT.

Thrombocytopenia is manifested as increased bleeding, such as mucosal bleedings from the nasal-oral area or the gastrointestinal tract, as well as oozing from wounds, ulcers or injection sites.

For pharmaceutical use, the proteins of the present invention are formulated for parenteral, particularly intravenous or subcutaneous, delivery according to conventional methods. Intravenous administration will be by bolus injection, controlled release, e.g., using mini-pumps or other appropriate technology, or by infusion over a typical period of one to several hours. In general, pharmaceutical formulations will include a hematopoietic protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. In addition, the hematopoietic proteins of the present invention may be combined with other cytokines, particularly early-acting cytokines such as stem cell factor, IL-3, IL-6, IL-11 or GM-CSF. When utilizing such a combination therapy, the cytokines may be combined in a single formulation or may be administered in separate formulations. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses will generally be in the range of 0.1 to 100 mg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins will commonly be administered over a period of up to 28 days following chemotherapy or bone-marrow transplant or until a platelet count of >20,000/mm$^3$, preferably >50,000/mm$^3$, is achieved. More commonly, the proteins will be administered over one week or less, often over a period of one to three days. In general, a therapeutically effective amount of ZCYTO18 is an amount sufficient to produce a clinically significant increase in the proliferation and/or differentiation of lymphoid or myeloid progenitor cells, which will be manifested as an increase in circulating levels of mature cells (e.g. platelets or neutrophils). Treatment of platelet disorders will thus be continued until a platelet count of at least 20,000/mm$^3$, preferably 50,000/mm$^3$, is reached. The proteins of the present invention can also be administered in combination with other cytokines such as IL-3, -6 and -11; stem cell factor; erythropoietin; G-CSF and GM-CSF. Within regimens of combination therapy, daily doses of other cytokines will in general be: EPO, 150 U/kg; GM-CSF, 5-15 lg/kg; IL-3, 1-5 lg/kg; and G-CSF, 1-25 lg/kg. Combination therapy with EPO, for example, is indicated in anemic patients with low EPO levels.

The proteins of the present invention can also be used ex vivo, such as in autologous marrow culture or liver cultures. For example, briefly, bone marrow is removed from a patient prior to chemotherapy and treated with ZCYTO18, optionally in combination with one or more other cytokines. The treated marrow is then returned to the patient after chemotherapy to speed the recovery of the marrow. In addition, the proteins of the present invention can also be used for the ex vivo expansion of marrow or peripheral blood progenitor (PBPC) cells. Prior to chemotherapy treatment, marrow can be stimulated with stem cell factor (SCF) or G-CSF to release early progenitor cells into peripheral circulation. These progenitors can be collected and concentrated from peripheral blood and then treated in culture with ZCYTO18, optionally in combination with one or more other cytokines, including but not limited to SCF, G-CSF, IL-3, GM-CSF, IL-6 or IL-11, to differentiate and proliferate into high-density megakaryocyte cultures, which can then be returned to the patient following high-dose chemotherapy. Such ex vivo uses are especially desirable in the instance that systemic administration is not tolerated by a patient. Thus the present invention to provide methods for stimulating the production of platelets and neutrophils in mammals including humans. The invention provides methods for stimulating platelet and neutrophil production in a mammal, ex vivo tissue sample, or cell cultures. The methods comprise administering to a mammal, ex vivo tissue sample, or cell culture a therapeutically effective amount of a hematopoietic protein selected from the group consisting of (a) proteins comprising the sequence of amino acids of SEQ ID NO:3 from amino acid residue 22 to amino acid residue 167; (b) allelic variants of (a); and (d) species homologs of (a) or (b), wherein the protein stimulates proliferation or differentiation of myeloid or lymphoid precursors, or the production of platelets, in combination with a pharmaceutically acceptable vehicle.

Moreover, the increase of platelets and neutrophils is desirable at a wound site not only in patients with blood diseases or undergoing chemotherapy as described above, but under normal conditions. A polypeptide such as ZCYTO18, that increases platelet levels in vivo, can be used in topological formulations including gels, meshes, poultices, liquids, and the like to aid in the healing of common cuts, burns, lacerations, abrasions, and the like. Moreover, such applications can be applied in any instance where the healing of skin, muscle, or the like is desired, even internally, such as after surgery.

The proteins of the present invention are also valuable tools for the in vitro study of the differentiation and development of hematopoietic cells, such as for elucidating the mechanisms of cell differentiation and for determining the lineages of mature cells, and may also find utility as proliferative agents in cell culture.

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products, and receptors. The stage of a cell population's differentiation is monitored by identification of markers present in the cell population. Myocytes, osteoblasts, adipocytes, chrondrocytes, fibroblasts and reticular cells are believed to originate from a common mesenchymal stem cell (Owen et al., *Ciba Fdn. Symp.* 136:42-46, 1988). Markers for mesenchymal stem cells have not been well identified (Owen et al., *J. of Cell Sci.* 87:731-738, 1987), so identification is usually made at the progenitor and mature cell stages. The novel polypeptides of the present invention may be useful for studies to isolate mesenchymal stem cells and myocyte or other progenitor cells, both in vivo and ex vivo.

There is evidence to suggest that factors that stimulate specific cell types down a pathway towards terminal differentiation or dedifferentiation affect the entire cell population originating from a common precursor or stem cell. Thus, the present invention includes stimulating or inhibiting the proliferation of myocytes, smooth muscle cells, osteoblasts, adipocytes, chrondrocytes, neuronal and endothelial cells. Molecules of the present invention for example, may while stimulating proliferation or differentiation of cardiac myocytes, inhibit proliferation or differentiation of adipocytes, by virtue of the affect on their common precursor/stem cells. Thus molecules of the present invention may have use in inhibiting chondrosarcomas, atherosclerosis, restenosis and obesity.

Assays measuring differentiation include, for example, measuring cell markers associated with stage-specific expression of a tissue, enzymatic activity, functional activity or morphological changes (Watt, *FASEB*, 5:281-284, 1991; Francis, *Differentiation* 57:63-75, 1994; Raes, *Adv. Anim. Cell Biol. Technol. Bioprocesses,* 161-171, 1989; all incorporated herein by reference). Alternatively, ZCYTO18 polypeptide itself can serve as an additional cell-surface or secreted marker associated with stage-specific expression of a tissue. As such, direct measurement of ZCYTO18 polypeptide, or its loss of expression in a tissue as it differentiates, can serve as a marker for differentiation of tissues.

Similarly, direct measurement of ZCYTO18 polypeptide, or its loss of expression in a tissue can be determined in a tissue or cells as they undergo tumor progression. Increases in invasiveness and motility of cells, or the gain or loss of expression of ZCYTO18 in a pre-cancerous or cancerous condition, in comparison to normal tissue, can serve as a diagnostic for transformation, invasion and metastasis in tumor progression. As such, knowledge of a tumor's stage of progression or metastasis will aid the physician in choosing the most proper therapy, or aggressiveness of treatment, for a given individual cancer patient. Methods of measuring gain and loss of expression (of either mRNA or protein) are well known in the art and described herein and can be applied to ZCYTO18 expression. For example, appearance or disappearance of polypeptides that regulate cell motility can be used to aid diagnosis and prognosis of prostate cancer (Banyard, J. and Zetter, B. R., *Cancer and Metast. Rev.* 17:449-458, 1999). As an effector of cell motility, ZCYTO18 gain or loss of expression may serve as a diagnostic for prostate and other cancers.

Moreover, the activity and effect of ZCYTO18 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly M S, et al. *Cell* 79: 315-328, 1994). C57BL6/J mice are treated with an experimental agent either through daily injection of recombinant protein, agonist or antagonist or a one time injection of recombinant adenovirus. Three days following this treatment, $10^5$ to $10^6$ cells are implanted under the dorsal skin. Alternatively, the cells themselves may be infected with recombinant adenovirus, such as one expressing ZCYTO18, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500-1800 mm$^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., ZCYTO18, on the ability of the tumor to recruit vasculature and undergo metastasis can thus be assessed. In addition, aside from using adenovirus, the implanted cells can be transiently transfected with ZCYTO18. Use of stable ZCYTO18 transfectants as well as use of induceable promoters to activate ZCYTO18 expression in vivo are known in the art and can be used in this system to assess ZCYTO18 induction of metastasis. Moreover, purified ZCYTO18 or ZCYTO18 conditioned media can be directly injected in to this mouse model, and hence be used in this system. For general reference see, O'Reilly M S, et al. *Cell* 79:315-328, 1994; and Rusciano D, et al. Murine Models of Liver Metastasis. *Invasion Metastasis* 14:349-361, 1995.

Polynucleotides encoding ZCYTO18 polypeptides are useful within gene therapy applications where it is desired to increase or inhibit ZCYTO18 activity. If a mammal has a mutated or absent ZCYTO18 gene, the ZCYTO18 gene can be introduced into the cells of the mammal. In one embodiment, a gene encoding a ZCYTO18 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320-30, 1991); an attenuated adenovirus vector, such as the vector described by Stratford-Perricaudet et al., *J. Clin. Invest.* 90:626-30, 1992; and a defective adeno-associated virus vector (Samulski et al., *J. Virol.* 61:3096-101, 1987; Samulski et al., *J. Virol.* 63:3822-8, 1989).

In another embodiment, a ZCYTO18 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Feigner et al., *Proc. Natl. Acad. Sci. USA* 84:7413-7, 1987; Mackey et al., *Proc. Natl. Acad. Sci. USA* 85:8027-31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963-7, 1992; Wu et al., *J. Biol. Chem.* 263:14621-4, 1988.

Antisense methodology can be used to inhibit ZCYTO18 gene transcription, such as to inhibit cell proliferation in vivo. Polynucleotides that are complementary to a segment of a ZCYTO18-encoding polynucleotide (e.g., a polynucleotide as set froth in SEQ ID NO:1) are designed to bind to ZCYTO18-encoding mRNA and to inhibit translation of such mRNA. Such antisense polynucleotides are used to inhibit expression of ZCYTO18 polypeptide-encoding genes in cell culture or in a subject.

The present invention also provides reagents which will find use in diagnostic applications. For example, the ZCYTO18 gene, a probe comprising ZCYTO18 DNA or RNA or a subsequence thereof can be used to determine if the ZCYTO18 gene is present on a human chromosome, such as chromosome 12, or if a mutation has occurred. Based on annotation of a fragment of human genomic DNA containing a part of ZCYTO18 genomic DNA (Genbank Accession No. AC007458), ZCYTO18 is located at the 12q15 region of chromosome 12. Detectable chromosomal aberrations at the ZCYTO18 gene locus include, but are not limited to, aneuploidy, gene copy number changes, loss of heterogeneity (LOH), translocations, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., *ibid.*; Marian, Chest 108:255-65, 1995).

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

ZCYTO18 is located at the 12q15 region of chromosome 12. Another T-cell expressed cytokine, interferon-gamma (IFN-γ) maps near this locus (12q14), suggesting that the 12q14-15 locus is an important region for T-cell expressed cytokines. Moreover, mutations in IFN-γ are associated with immunodeficiency (See, e.g., Tzoneva, M. et al., *Clin. Genet.* 33:454-456, 1988). Mutations in ZCYTO18, are likely to cause human disease as well, such as immunodeficiency, autoimmune disease, lymphoid cell cancers, or other immune dysfunction. Moreover, there are several genes that map to the ZCYTO18 locus that are associated with human disease states, such as cancer. 12q13-q15 region is involved in a variety of malignant and benign solid tumors (including salivary adenomas and uterine leiomyomas), with 12q15 as a common break point. Moreover, the high mobility group protein isoform I-C(HMGIC) maps to 12q15 and is involved in benign lipomas and other tumors. As ZCYTO18 maps to 12q15 as well, there can be an association between loss of ZCYTO18 function and tumor formation or progression. Moreover, translocations in 12q13-15 are prevalent in soft tissue tumors, multiple lipomatosis and malignant mixoid liposarcoma. ZCYTO18 polynucleotide probes can be used to detect abnormalities or genotypes associated with these cancer susceptibility markers. Because there is abundant evidence for cancer resulting from mutations in the 12q15 region, and ZCYTO18 also maps to this chromosomal locus, mutations in ZCYTO18 may also be directly involved in or associated with cancers, such as lymphoid cell cancers or other tumors.

A diagnostic could assist physicians in determining the type of disease and appropriate associated therapy, or assistance in genetic counseling. As such, the inventive anti-ZCYTO18 antibodies, polynucleotides, and polypeptides can be used for the detection of ZCYTO18 polypeptide, mRNA or anti-ZCYTO18 antibodies, thus serving as markers and be directly used for detecting or genetic diseases or cancers, as described herein, using methods known in the art and described herein. Further, ZCYTO18 polynucleotide probes can be used to detect abnormalities or genotypes associated with chromosome 12q15 deletions and translocations associated with human diseases, such as multiple lipomatosis and malignant mixoid liposarcoma (above), or other translocations involved with malignant progression of tumors or other 12q15 mutations, which are expected to be involved in chromosome rearrangements in malignancy; or in other cancers. Similarly, ZCYTO18 polynucleotide probes can be used to detect abnormalities or genotypes associated with chromosome 12q15 trisomy and chromosome loss associated with human diseases or spontaneous abortion. Moreover, amongst other genetic loci, those for Scapuloperoneal spinal muscular atrophy (12q13.3-q15), mucopolysaccaridosis (12q14), pseudo-vitamin D deficiency Rickets as a result of mutation in Cytochrome CYP27B1 (12q14) and others, all manifest themselves in human disease states as well as map to this region of the human genome. All of these serve as possible candidate genes for an inheritable disease which show linkage to the same chromosomal region as the ZCYTO18 gene. Thus, ZCYTO18 polynucleotide probes can be used to detect abnormalities or genotypes associated with these defects.

As discussed above, defects in the ZCYTO18 gene itself may result in a heritable human disease state. Molecules of the present invention, such as the polypeptides, antagonists, agonists, polynucleotides and antibodies of the present invention would aid in the detection, diagnosis prevention, and treatment associated with a ZCYTO18 genetic defect. In addition, ZCYTO18 polynucleotide probes can be used to detect allelic differences between diseased or non-diseased individuals at the ZCYTO18 chromosomal locus. As such, the ZCYTO18 sequences can be used as diagnostics in forensic DNA profiling.

In general, the diagnostic methods used in genetic linkage analysis, to detect a genetic abnormality or aberration in a patient, are known in the art. Analytical probes will be generally at least 20 nt in length, although somewhat shorter probes can be used (e.g., 14-17 nt). PCR primers are at least 5 nt in length, preferably 15 or more, more preferably 20-30 nt. For gross analysis of genes, or chromosomal DNA, a ZCYTO18 polynucleotide probe may comprise an entire exon or more. Exons are readily determined by one of skill in the art by comparing ZCYTO18 sequences (SEQ ID NO:1) with the human genomic DNA for ZCYTO18 (Genbank Accession No. AC007458). In general, the diagnostic methods used in genetic linkage analysis, to detect a genetic abnormality or aberration in a patient, are known in the art. Most diagnostic methods comprise the steps of (a) obtaining a genetic sample from a potentially diseased patient, diseased patient or potential non-diseased carrier of a recessive disease allele; (b) producing a first reaction product by incubating the genetic sample with a ZCYTO18 polynucleotide probe wherein the polynucleotide will hybridize to complementary polynucleotide sequence, such as in RFLP analysis or by incubating the genetic sample with sense and antisense primers in a PCR reaction under appropriate PCR reaction conditions; (iii) Visualizing the first reaction product by gel electrophoresis and/or other known method such as visualizing the first reaction product with a ZCYTO18 polynucleotide probe wherein the polynucleotide will hybridize to the complementary polynucleotide sequence of the first reaction; and (iv) comparing the visualized first reaction product to a second control reaction product of a genetic sample from wild type patient. A difference between the first reaction product and the control reaction product is indicative of a genetic abnormality in the diseased or potentially diseased patient, or the presence of a heterozygous recessive carrier phenotype for a non-diseased patient, or the presence of a genetic defect in a tumor from a diseased patient, or the presence of a genetic abnormality in a fetus or pre-implantation embryo. For example, a difference in restriction fragment pattern, length of PCR products, length of repetitive sequences at the ZCYTO18 genetic locus, and the like, are indicative of a genetic abnormality, genetic aberration, or allelic difference in comparison to the normal wild type control. Controls can be from unaffected family members, or unrelated individuals, depending on the test and availability of samples. Genetic samples for use within the present invention include genomic DNA, mRNA, and cDNA isolated form any tissue or other biological sample from a patient, such as but not limited to, blood, saliva, semen, embryonic cells, amniotic fluid, and the like. The polynucleotide probe or primer can be RNA or DNA, and will comprise a portion of SEQ ID NO:1, the complement of SEQ ID NO:1, or an RNA equivalent thereof. Such methods of showing genetic linkage analysis to human disease phenotypes are well known in the art. For reference to PCR based methods in diagnostics see see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

Aberrations associated with the ZCYTO18 locus can be detected using nucleic acid molecules of the present invention by employing standard methods for direct mutation analysis, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83-88 (Humana Press, Inc. 1998)). Direct analysis of an ZCYTO18 gene for a mutation can be performed using a subject's genomic DNA. Methods for amplifying genomic DNA, obtained for example from peripheral blood lymphocytes, are well-known to those of skill in the art (see, for example, Dracopoli et al. (eds.), *Current Protocols in Human Genetics*, at pages 7.1.6 to 7.1.7 (John Wiley & Sons 1998)).

Mice engineered to express the ZCYTO18 gene, referred to as "transgenic mice," and mice that exhibit a complete absence of ZCYTO18 gene function, referred to as "knockout mice," may also be generated (Snouwaert et al., *Science* 257: 1083, 1992; Lowell et al., *Nature* 366:740-42, 1993; Capecchi, M. R., Science 244: 1288-1292, 1989; Palmiter, R. D. et al. *Annu Rev Genet.* 20: 465-499, 1986). For example, transgenic mice that over-express ZCYTO18, either ubiquitously or under a tissue-specific or tissue-restricted promoter can be used to ask whether over-expression causes a phenotype. For example, over-expression of a wild-type ZCYTO18 polypeptide, polypeptide fragment or a mutant thereof may alter normal cellular processes, resulting in a phenotype that identifies a tissue in which ZCYTO18 expression is functionally relevant and may indicate a therapeutic target for the ZCYTO18, its agonists or antagonists. For example, a preferred transgenic mouse to engineer is one that over-expresses the mature ZCYTO18 polypeptide (amino acid residues 23 (Pro) to 167 (Ile) of SEQ ID NO:3). Moreover, such over-expression may result in a phenotype that shows similarity with human diseases. Similarly, knockout ZCYTO18 mice can be used to determine where ZCYTO18 is absolutely required in vivo. The phenotype of knockout mice is predictive of the in vivo effects of that a ZCYTO18 antagonist, such as those described herein, may have. The human or mouse ZCYTO18 cDNA can be used to generate knockout mice. These mice may be employed to study the ZCYTO18 gene and the protein encoded thereby in an in vivo system, and can be used as in vivo models for corresponding human diseases. Moreover, transgenic mice expression of ZCYTO18 antisense polynucleotides or ribozymes directed against ZCYTO18, described herein, can be used analogously to transgenic mice described above. Studies may be carried out by administration of purified ZCYTO18 protein, as well.

For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a ZCYTO18 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 µg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of ZCYTO18 is an amount sufficient to produce a clinically significant change in hematopoietic or immune function.

The invention is further illustrated by the following non-limiting examples.

EXAMPLES

Example 1

Using an EST Sequence to Identify and Clone ZCYTO18

Novel ZCYTO18 encoding polynucleotides and polypeptides of the present invention were initially identified by querying an EST database for sequences homologous to conserved motifs within the cytokine family. A primary expressed sequence tag (EST) from a human T-lymphocyte cDNA library was identified.

An initial partial sequence was obtained from the sequencing of the EST (INC4345486). Additional 5' sequence was obtained from sequencing the cDNA fragment obtained by PCR from the Northern Analysis (Example 2, below) and by further PCR using oligonucleotides ZC25,840 (SEQ ID NO:5) and ZC25,841 (SEQ ID NO:6) in a PCR using human mixed lymphocyte reaction (MLR) cDNA. Thermocycler conditions were as described in Example 2 below. The resulting 1082 by full length sequence is disclosed in SEQ ID NO:1 and the corresponding amino acid sequence is shown in SEQ ID NO:2 and SEQ ID NO:3. The full length novel cytokine was designated ZCYTO18.

Example 2

Zcyto18 Tissue Distribution

Northerns were performed using Human Multiple Tissue Blots (MTN1, MTN2 and MTN3) from Clontech (Palo Alto, Calif.) to determine the tissue distribution of human ZCYTO18. A 237 by cDNA probe was obtained using the PCR. Oligonucleotides ZC25,838 (SEQ ID NO:7) and ZC25, 839 (SEQ ID NO:8) were used as primers. Marathon cDNA, synthesized in-house using Marathon cDNA Kit (Clontech) and protocol, was used as a template. The following human tissue specific cDNAs were also used: lymph node, bone marrow, CD4+, CD8+, spleen, and MLR, along with human genomic DNA (Clontech). Thermocycler conditions were as follows: one cycle at 94° C. for 2 min.; 35 cycles of 94° C. for 15 sec., 62° C. for 20 sec., and 72° C. for 30 sec.; one cycle at 72° C. for 7 min.; followed by a 4° C. hold. The correct predicted band size (237 bp) was observed on a 4% agarose gel in CD4+ and MLR reactions, along with the genomic DNA reaction. A band was excised and purified using a Gel Extraction Kit (Qiagen, Chatsworth, Calif.) according to manufacturer's instructions. The cDNA was radioactively labeled using a Rediprime II DNA labeling kit (Amersham, Arlington Heights, Ill.) according to the manufacturer's specifications. The probe was purified using a NUCTRAP push column (Stratagene Cloning Systems, La Jolla, Calif.). EXPRESSHYB (Clontech, Palo Alto, Calif.) solution was used for prehybridization and as a hybridizing solution. Hybridization took place overnight at 55° C., using $2\times10^6$ cpm/ml labeled probe. The blots were then washed in 2×SSC and 0.1% SDS at room temperature, then with 2×SSC and 0.1% SDS at 65° C., followed by a wash in 0.1×SSC and 0.1% SDS at 65° C. The blots were exposed 5 days to Biomax MS film (Kodak, Rochester, N.Y.). No transcript signals were observed on the MTN blots after development.

A RNA Master Dot Blot (Clontech) that contained RNAs from various tissues that were normalized to 8 housekeeping genes was also probed and hybridized as described above. A signal was observed in genomic DNA. While a faint signal in lymph node and very faint signals in fetal liver, skeletal muscle, and placenta were observed it was inconclusive whether these signals were significantly above background.

Example 3

Identification of Cells Expressing ZCYTO18 Using RT-PCR

Specific human cell types were isolated and screened for ZCYTO18 expression by RT-PCR. B-cells were isolated from fresh human tonsils by mechanical disruption through 100 µm nylon cell strainers (Becton Dickinson Biosciences, Franklin Lakes, N.J.). The B-cell suspensions were enriched for CD19+ B-cells by positive selection with VarioMACS VS+ magnetic column and CD19 microbeads (Miltenyi Biotec, Auburn, Calif.) as per manufacturer's instructions. T-cells were isolated from human apheresed blood samples. CD3+ T-cells were purified by CD3 microbead VarioMACS positive selection and monocytes were purified by VarioMACS negative selection columns (Miltenyi) as per manufacturer's instructions. Samples from each population were stained and analyzed by fluorescent antibody cell sorting (FACS) (Bectin Dickinson, San Jose, Calif.) analysis to determine the percent enrichment and resulting yields. CD19+ B-cells were approximately 96% purified, CD3+ T-cells were approximately 95% purified, and monocytes were approximately 96% purified.

RNA was prepared, using a standard method in the art, from all three cell types that were either resting or activated. RNA was isolated from resting cells directly from the column preparations above. The CD19+ and CD3+ cells were activated by culturing at 500,000 cells/ml in RPMI+10% FBS containing PMA 5 ng/ml (Calbiochem, La Jolla, Calif.) and Ionomycin 0.5 ug/ml (Calbiochem) for 4 and 24 hours. The monocytes were activated by culturing in RPMI+10% FBS containing LPS 10 ng/ml (Sigma St. Louis Mo.) and rhIFN-g 10 ng/ml (R&D, Minneapolis, Minn.) for 24 hours. Cells were harvested and washed in PBS. RNA was prepared from the cell pellets using RNeasy Midiprep™ Kit (Qiagen, Valencia, Calif.) as per manufacturer's instructions and first strand cDNA synthesis was generated with Superscript II™ Kit (GIBCO BRL, Grand Island, N.Y.) as per manufacturers protocol.

Oligos ZC25,838 (SEQ ID NO:7) and ZC25,840 (SEQ ID NO:5) were used in a PCR reaction to screen the above described samples for a 473 by fragment corresponding to ZCYTO18 message. PCR amplification was performed with Taq Polymerase (BRL Grand Island N.Y.), and reaction conditions as follows: 35 cycles of 94° C. for 15 sec., 62° C. for 20 sec., 72° C. for 30 sec.; 1 cycle at 72° C. for 7 min.; and 4° C. soak. 5 ul of each 50 µl reaction volume was run on a 0.9% agarose 0.5XTBE gel to identify resultant products. Table 5 below describes the results. PCR products were scored as (−) for no product, (+) for expected PCR product visible, (++) increased presence of PCR product and (+++) being the strongest signal.

TABLE 5

Cells expressing ZCYTO18 using RT-PCR

| cDNA Source | Activation | PCR Product |
|---|---|---|
| CD3+ cells | 0 hr resting | + |
| | 4-hr activated | +++ |
| CD19+ cells | 4 hr activated | ++ |
| | 24 hr activated | + |
| Monocytes | 24 hr activated | − |

These results indicated that ZCYTO18 message is present in resting CD3+ T-cells and increases with mitogenic activation. It also appears to be expressed by 4-hr activated human CD19+ B-cells and reduced in expression in 24 hr activated B-cells. There was no apparent message in activated monocytes.

Example 4

Identification of hZCYTO18 Message in an Activated T-Cell Library

A. The Vector for CD3+Selected Library Construction

The vector for CD3+ selected library construction was pZP7NX. The pZP7NX vector was previously constructed as follows: The coding region for the DHFR selective marker in vector pZP7 was removed by DNA digestion with NcoI and PstI restriction enzymes (Boehringer Mannheim). The digested DNA was run on 1% agarose gel, cut out and gel purified using the Qiagen Gel Extraction Kit (Qiagen) as per manufacturer's instructions. A DNA fragment representing the coding region of Zeocin selective marker was amplified by PCR method with primers ZC13,946 (SEQ ID NO:9) and ZC13,945 (SEQ ID NO:10), and pZeoSV2(+) as a template. There are additional PstI and BclI restriction sites in primer ZC13,946 (SEQ ID NO:9), and additional NcoI and SfuI sites in primer ZC13,945 (SEQ ID NO:10). The PCR fragment was cut with PstI and NcoI restriction enzymes and cloned into pZP7 vector prepared by cleaving with the same two enzymes and subsequent gel purification. This vector was named pZP7Z. Then the Zeocin coding region was removed by DNA digestion of vector pZP7Z with BclI and SfuI restriction enzymes. The digested DNA was run on 1% agarose gel, cut out and gel purified, and then ligated with a DNA fragment of Neomycin coding region cut from pZem228 vector with the same restriction enzymes (BclI and SfuI).

This new vector was named pZP7N, in which the coding region for DHFR selective marker was replaced by the coding region for a Neomycin selective marker from vector pZem228. A stuffer fragment including an Xho1 site was added to pZP7N to create a vector suitable for high efficiency directional cloning of cDNA; this new vector was called pZP7NX. To prepare the vector for cDNA, 20 µg of pZP7NX was digested with 20 units of EcoR1 (Life Technologies Gaithersberg, Md.) and 20 units of Xho1 (Boehringer Mannheim Indianapolis, Ind.) for 5 hours at 37° C., then 68° C. for 15 minutes. The digest was then run on a 0.8% low melt agarose 1xTAE gel to separate the stuffer from the vector. The vector band was excised and digested with "beta-Agarase" (New England Biolabs, Beverly, Mass.) following the manufacturer's recommendations. After ethanol precipitation the digested vector was resuspended in water to 45 ng/ml in preparation for ligation of CD3+ selected cDNA library described below.

B. Preparation of Primary Human Activated CD3+Selected Cell cDNA Library

Approximately $1.5 \times 10^8$ primary human CD3+ selected cells stimulated in ionomycin/PMA were isolated by centrifugation after culturing at 37° C. for 13 hours. Total RNA was isolated from the cell pellet using the "RNeasy Midi" kit from Qiagen, Inc. (Valencia, Calif.). mRNA was isolated from 225 micrograms of total RNA using the "MPG mRNA purification kit" from CPG Inc. (Lincoln Park, N.J.). 3.4 micrograms of mRNA was isolated and converted to double stranded cDNA using the following procedure.

First strand cDNA from stimulated human CD3+ selected cells was synthesized as follows. Nine µl Oligo d(T)-selected poly(A) CD3+ RNA at a concentration of 0.34 mg/µl and 1.0 µl of 1 µg/µl first strand primer ZC18,698 (SEQ ID NO:11) containing an XhoI restriction site were mixed and heated at 65° C. for 4 minutes and cooled by chilling on ice. First strand cDNA synthesis was initiated by the addition of 9 µl of first strand buffer (5× SUPERSCRIPT® buffer; Life Technologies), 4 µl of 100 mM dithiothreitol and 2 µl of a deoxynucleotide triphosphate solution containing 10 mM each of dATP, dGTP, dTTP and 5-methyl-dCTP (Pharmacia Biotech Inc.) to the RNA-primer mixture. The reaction mixture was incubated at 45° C. for 4 minutes followed by the addition of 8 µl of 200 U/µl SuperscriptII®, RNase H— reverse transcriptase (Life Technologies). The reaction was incubated at 45° C. for 45 minutes followed by an incubation ramp of 1° C. every 2 minutes to 50° C. where the reaction was held for 10 minutes. To denature any secondary structure and allow for additional extension of the cDNA the reaction was then heated to 70° C. for 2 minutes then dropped to 55° C. for 4 minutes after which 2 µl of SuperscriptII® RT was added and incubated an additional 15 minutes followed by a ramp up to 70° C. at 1 minute/1° C. Unincorporated nucleotides were removed from the cDNA by twice precipitating in the presence of 2 µg of glycogen carrier, 2.0 M ammonium acetate and 2.5 volume ethanol, followed by a 100 µl wash with 70% ethanol. The cDNA was resuspended in 98 µl water for use in second strand synthesis.

Second strand synthesis was performed on the first strand cDNA under conditions that promoted first strand priming of second strand synthesis resulting in DNA hairpin formation. The second strand reaction contained 98 µl of the first strand cDNA, 30 µl of 5× polymerase I buffer (100 mM Tris: HCl, pH 7.5, 500 mM KCl, 25 mM MgCl2, 50 mM $(NH_4)_2SO_4$), 2 µl of 100 mM dithiothreitol, 6 µl of a solution containing 10 mM of each deoxynucleotide triphosphate, 5 µl of 5 mM b-NAD, 1 µl of 3 U/µl *E. coli* DNA ligase (New England Biolabs Inc.) and 4 µl of 10 U/µl *E. coli* DNA polymerase I (New England Biolabs Inc.). The reaction was assembled at room temperature and was incubated at room temperature for 2 minutes followed by the addition of 4 µl of 3.8 U/µl RNase H (Life Technologies). The reaction was incubated at 15° C. for two hours followed by a 15 minute incubation at room temperature. 10 µl of 1M TRIS pH7.4 was added to the reaction and extracted twice with phenol/chloroform and once with chloroform, the organic phases were then back extracted with 50 µl of TE (10 mM TRIS pH 7.4, 1 mM EDTA), pooled with the other aqueous and ethanol precipitated in the presence of 0.3 M sodium acetate. The pellet was washed with 100 µl 70% ethanol air dried and resuspended in 40 µl water.

The single-stranded DNA of the hairpin structure was cleaved using mung bean nuclease. The reaction mixture contained 40 µl of second strand cDNA, 5 µl of 10× mung bean nuclease buffer (Life technologies), 5 µl of mung bean nuclease (Pharmacia Biotech Corp.) diluted to 1 U/µl in 1× mung bean nuclease buffer. The reaction was incubated at 37° C. for 45 minutes. The reaction was terminated by the addition of 10 µl of 1 M Tris: HCl, pH 7.4 followed by sequential phenol/chloroform and chloroform extractions as described above. Following the extractions, the cDNA was ethanol precipitated in the presence of 0.3 M sodium acetate. The pellet was washed with 100 µl 70% ethanol air dried and resuspended in 38 µl water.

The resuspended cDNA was blunt-ended with T4 DNA polymerase. The cDNA, which was resuspended in 38 µl of water, was mixed with 12 µl 5× T4 DNA polymerase buffer (250 mM Tris:HCl, pH 8.0, 250 mM KCl, 25 mM MgC12), 2 µl 0.1 M dithiothreitol, 6 µl of a solution containing 10 mM of each deoxynucleotide triphosphate and 2 µl of 1 U/µl T4 DNA polymerase (Boehringer Mannheim Corp.). After an incubation of 45 minutes at 15° C., the reaction was terminated by the addition of 30 µl TE followed by sequential phenol/chloroform and chloroform extractions and back extracted with 20 µl TE as described above. The DNA was ethanol precipitated in the presence of 2 µl Pellet Paint™ (Novagen) carrier and 0.3 M sodium acetate and was resuspended 11 µl of water.

Eco RI adapters were ligated onto the 5' ends of the cDNA described above to enable cloning into an expression vector. 11 µl of cDNA and 4 µl of 65 pmole/µl of Eco RI hemiphophorylated adaptor (Pharmacia Biotech Corp) were mixed with 5 µl 5× ligase buffer (Life Technologies), 2 µl of 10 mM ATP and 3 µl of 1 U/µl T4 DNA ligase (Life Technologies), 1 µl 10× ligation buffer (Promega Corp), 9 µl water. The extra dilution with 1× buffer was to prevent the pellet paint from precipitating. The reaction was incubated 9 hours in a water bath temperature ramp from 10° C. to 22° C. over 9 hours, followed by 45 minutes at 25° C. The reaction was terminated by incubation at 68° C. for 15 minutes.

To facilitate the directional cloning of the cDNA into an expression vector, the cDNA was digested with XhoI, resulting in a cDNA having a 5' Eco RI cohesive end and a 3' XhoI cohesive end. The XhoI restriction site at the 3' end of the cDNA had been previously introduced using the ZC18698 primer. Restriction enzyme digestion was carried out in a reaction mixture containing 35 µl of the ligation mix described above, 6 µl of 10× H buffer (Boehringer Mannheim Corp.), 1 µl of 2 mg/ml BSA (Biolabs Corp.), 17 µl water and 1.0 µl of 40 U/µl XhoI (Boehringer Mannheim). Digestion was carried out at 37° C. for 1 hour. The reaction was terminated by incubation at 68° C. for 15 minutes followed by ethanol precipitation, washing drying as described above and resuspension in 30 µl water.

The resuspended cDNA was heated to 65° C. for 5 minutes and cooled on ice, 4 µl of 5× gel loading dye (Research Genetics Corp.) was added, the cDNA was loaded onto a 0.8% low melt agarose 1×TAE gel (SEA PLAQUE GTG™ low melt agarose; FMC Corp.) and electrophoresed. The contaminating adapters and cDNA below 0.6 Kb in length were excised from the gel. The electrodes were reversed, molten agarose was added to fill in the wells, the buffer was changed and the cDNA was electrophoresed until concentrated near the lane origin. The area of the gel containing the concentrated cDNA was excised and placed in a microfuge tube, and the agarose was melted by heating to 65° C. for 15 minutes. Following equilibration of the sample to 45° C., 2 µl of 1 U/µl Beta-agarase I (Biolabs, Inc.) was added, and the mixture was incubated for 90 min. at 45° C. to digest the agarose. After incubation, 1 tenth volume of 3 M Na acetate was added to the sample, and the mixture was incubated on ice for 15 minutes. The sample was centrifuged at 14,000×g for 15 minutes at room temperature to remove undigested agarose, the cDNA was ethanol precipitated, washed in 70% ethanol, air-dried and resuspended in 40 µl water.

To determine the optimum ratio of cDNA to vector several ligations were assembled and electroporated. Briefly, 2 µl of 5× T4 ligase buffer (Life Technologies), 1 µl of 10 mM ATP, 1 µl pZP7NX digested with EcoR1-Xho1, 1 µl T4 DNA ligase diluted to 0.25u/µl (Life Technologies) water to 10 µl and 0.5, 1, 2 or 3 µl of cDNA were mixed in 4 separate ligations, incubated at 22° C. for 4 hours, 68° C. for 20 minutes, sodium acetate-ethanol precipitated, washed, dried and resuspended in 10 ll. A single microliter of each ligation was electroporated into 40 µl DH10b ElectroMax™ electrocompetent bacteria (Life Technologies) using a 0.1 cm cuvette (Biorad) and a Genepulser, pulse controllerä (Biorad) set to 2.5 KV, 25 lF, 200 ohms. These cells were immediately resuspended in 1 ml. SOC broth (Manniatis, et al. supra.) followed by 500 ll of 50% glycerol-SOC as a preservative. These "glycerol stocks" were frozen in several aliquots at −70° C. An aliquot of each was thawed and plated serially on LB-agar plates supplemented with ampicillin at 100 µg/ml. Colony numbers indicated that the optimum ratio of CD3+ cDNA to pZP7NX vector was 1 µl to 45 ng; such a ligation yielded 4.5 million primary clones.

C. PCR Identification of Zcyto18 Message in Activated T-Cell Library

PCR was performed using oligos ZC25,838 (SEQ ID NO:7) and ZC25,840 (SEQ ID NO:5) to screen the above library for presence of a 473 by product corresponding to ZCYTO18 clones. PCR amplification was performed with Taxi Polymerase (BRL Grand Island N.Y.), and conditions as follows: 30 cycles of 94° C. for 15 sec., 62° C. 20 sec., 72° C. 30 sec.; 1 cycle at 72° C. for 7 min.; and a 4° C. soak. 5 µl of each 50 µl reaction volume was run on a 0.9% agarose 0.5× TBE gel to identify resultant products. Table 6 below describes the results. PCR products were scored as (−) for no product, (+) for expected PCR product visible, (++) increased presence of PCR product and (+++) being the strongest signal.

TABLE 6

Identification of ZCYTO18 message in activated T-Cell Library

| Template | PCR Product |
|---|---|
| 1 ng Activated Library | + |
| 10 ng Activated Library | ++ |
| 100 ng Activated Library | +++ |
| 100 ng Vector Control | − |
| No Template Control | − |

These results indicate the presence of a ZCYTO18 cDNA clone and therefore message in activated CD3+ T-cells.

Example 5

Southern Blot Analysis

Southern blots were performed using EVO Mammalian Group/EcoRI Southern Blots (Quantum Biotechnologies, Inc., Montreal, Canada) to determine the presence of orthologous ZCYTO18 sequences. A ZCYTO18 probe was generated by labeling 25 ng of ZCYTO18 fragment, as described in Example 2, using Prime-It II Random Primer labeling kit (Stratagene, La Jolla, Calif.). Hybridization was performed using Expresshyb (Clontech) with 5×10⁵ cpm/ml probe and conditions of 65° C. overnight. Stringency washes were performed with 0.2×SSC, 0.1% SDS at 45° C. The blot was exposed overnight at −80° C. to X-ray film and analyzed.

Results showed a strong approximately 1 kb band in the human genomic DNA sample with weaker bands present at approximately 7 and 20 kb for murine genomic DNA demonstrating the presence of a putative murine homolog for ZCYTO18.

The mouse cDNA sequence was cloned using standard methods and is shown in SEQ ID NO:37, and corresponding polypeptides sequence shown in SEQ ID NO:38.

Example 6

Chromosomal Assignment and Placement of Zcyto18

Zcyto18 was mapped to chromosome 12 using the commercially available version of the "Stanford G3 Radiation Hybrid Mapping Panel" (Research Genetics, Inc., Huntsville, AL). The "Stanford G3 RH Panel" contains DNA from each of 83 radiation hybrid clones of the whole human genome, plus two control DNAs (the RM donor and the A3 recipient).

For the mapping of Zcyto18 with the "Stanford G3 RH Panel", 20 µl reactions were set up in a 96-well microtiter plate compatible for PCR (Stratagene, La Jolla, Calif.) and used in a "RoboCycler Gradient 96" thermal cycler (Stratagene). Each of the 85 PCR reactions consisted of 2 µl 10× KlenTaq PCR reaction buffer (CLONTECH Laboratories, Inc., Palo Alto, Calif.), 1.6 µl dNTPs mix (2.5 mM each, PERKIN-ELMER, Foster City, Calif.), 1 µl sense primer, ZC 26,414 (SEQ ID NO:12), 1 antisense primer, ZC 26,415 (SEQ ID NO:13), 2 µl "RediLoad" (Research Genetics, Inc., Huntsville, Ala.), 0.4 µl 50× Advantage KlenTaq Polymerase Mix (Clontech Laboratories, Inc.), 25 ng of DNA from an individual hybrid clone or control and distilled water for a total volume of 20 µl. The reactions were overlaid with an equal amount of mineral oil and sealed. The PCR cycler conditions were as follows: an initial 1 cycle 5 minute denaturation at 94° C., 35 cycles of a 45 seconds denaturation at 94° C., 45 seconds annealing at 66° C. and 1 minute AND 15 seconds extension at 72° C., followed by a final 1 cycle extension of 7 minutes at 72° C. The reactions were separated by electrophoresis on a 2% agarose gel (EM Science, Gibbstown, N.J.) and visualized by staining with ethidium bromide.

The results showed linkage of Zcyto18 to the chromosome 12 marker SHGC-17533 with a LOD score of >12 and at a distance of 0 cR_10000 from the marker. The use of surrounding genes and markers positions Zcyto18 in the 12q14-q24.3 chromosomal region.

Example 7

Construct for Generating CEE-Tagged Zcyto18

Oligonucleotides were designed to generate a PCR fragment containing the Kozak sequence and the coding region for ZCYTO18, without its stop codon. These oligonucleotides were designed with a KpnI site at the 5' end and a BamHI site at the 3' end to facilitate cloning into pHZ200-CEE, our standard vector for mammalian expression of C-terminal Glu-Glu tagged (SEQ ID NO:14) proteins. The pHZ200 vector contains an MT-1 promoter.

PCR reactions were carried out using Turbo Pfu polymerase (Stratagene) to amplify a ZCYTO18 cDNA fragment. About 20 ng human ZCYTO18 polynucleotide template (SEQ ID NO:1), and oligonucleotides ZC28590 (SEQ ID NO:16) and ZC28580 (SEQ ID NO:17) were used in the PCR reaction. PCR reaction conditions were as follows: 95° C. for 5 minutes; 30 cycles of 95° C. for 60 seconds, 55° C. for 60 seconds, and 72° C. for 60 seconds; and 72° C. for 10 minutes; followed by a 4° C. hold. PCR products were separated by agarose gel electrophoresis and purified using a QiaQuick™ (Qiagen) gel extraction kit. The isolated, approximately 600 bp, DNA fragment was digested with KpnI and BamHI (Boerhinger-Mannheim), gel purified as above and ligated into pHZ200-CEE that was previously digested with KpnI and BamHI.

About one microliter of the ligation reaction was electroporated into DH10B ElectroMax™ competent cells (GIBCO BRL, Gaithersburg, Md.) according to manufacturer's direction and plated onto LB plates containing 100 µg/ml ampicillin, and incubated overnight. Colonies were picked and screened by PCR using oligonucleotides ZC28,590 (SEQ ID NO:16) and ZC28,580 (SEQ ID NO:17), with PCR conditions as described above. Clones containing inserts were then sequenced to confirm error-free ZCYTO18 inserts. Maxipreps of the correct pHZ200-ZCYTO18-CEE construct, as verified by sequence analysis, were performed.

Example 8

Transfection and Expression of Zcyto18-CEE Polypeptides

BHK 570 cells (ATCC No. CRL-10314), were plated at about 1×10$^6$ cells/100 mm culture dish in 6.4 ml of serum free (SF) DMEM media (DMEM, Gibco/BRL High Glucose) (Gibco BRL, Gaithersburg, Md.). The cells were transfected with an expression plasmid containing ZCYTO18-CEE described above (Example 7), using Lipofectin™ (Gibco BRL), in serum free (SF) DMEM according to manufacturer's instructions.

The cells were incubated at 37° C. for approximately five hours, then 10 ml of DMEM/10% fetal bovine serum (FBS) (Hyclone, Logan, Utah) was added. The plates were incubated at 37° C., 5% $CO_2$, overnight and the DMEM/10% FBS media was replaced with selection media (5% FBS/DMEM with 1 µM methotrexate (MTX)) the next day.

Approximately 7-10 days post-transfection, pools of cells or colonies were mechanically picked to 12-well plates in one ml of 5% FCS/DMEM with 5 µM MTX, then grown to confluence. Cells were then incubated in 5% FCS/DMEM with 10 µM MTX for at least 14 days. Conditioned media samples from positive expressing clonal colonies and pools were then tested for expression levels via SDS-PAGE and Western analysis. A high-expressing clonesor pools were picked and expanded for ample generation of conditioned media for purification of the ZCYTO18-CEE expressed by the cells (Example 9).

Example 9

Purification of ZCYTO18-CEE from BHK 570 Cells

Unless otherwise noted, all operations were carried out at 4° C. The following procedure was used for purifying ZCYTO18 polypeptide containing C-terminal GluGlu (EE) tags (SEQ ID NO:14). A Protease inhibitor solution was added to the concentrated conditioned media containing ZCYTO18-CEE (Example 8) to final concentrations of 2.5 mM ethylenediaminetetraacetic acid (EDTA, Sigma Chemical Co. St. Louis, Mo.), 0.003 mM leupeptin (Boehringer-Mannheim, Indianapolis, Ind.), 0.001 mM pepstatin (Boehringer-Mannheim) and 0.4 mM Pefabloc (Boehringer-Mannheim).

About 100 ml column of anti-EE G-Sepharose (prepared as described below) was poured in a Waters AP-5, 5 cm×10 cm glass column. The column was flow packed and equilibrated on a BioCad Sprint (PerSeptive BioSystems, Framingham, Mass.) with phosphate buffered saline (PBS) pH 7.4. The concentrated conditioned media was 0.2 micron sterile filtered, pH adjusted to 7.4, then loaded on the column overnight with about 1 ml/minute flow rate. The column was washed with 10 column volumes (CVs) of phosphate buffered saline (PBS, pH 7.4), then plug eluted with 200 ml of PBS (pH 6.0) containing 0.1 mg/ml EE peptide (Anaspec, San Jose, Calif.) at 5 ml/minute. The EE peptide used has the sequence EYMPME (SEQ ID NO:14). Five ml fractions were collected over the entire elution chromatography and absorbance at 280 and 215 nM were monitored; the pass through and wash pools were also saved and analyzed. The EE-polypeptide elution peak fractions were analyzed for the target protein via SDS-PAGE Silver staining and Western Blotting with the anti-EE HRP conjugated antibody. The polypeptide elution fractions of interest were pooled and concentrated from 60 ml to 5.0 ml using a 10,000 Dalton molecular weight cutoff membrane spin concentrator (Millipore, Bedford, Mass.) according to the manufacturer's instructions.

To separate ZCYTO18-CEE polypeptide from free EE peptide and any contaminating co-purifying proteins, the pooled concentrated fractions were subjected to size exclusion chromatography on a 1.5×90 cm Sephadex 5200 (Pharmacia, Piscataway, N.J.) column equilibrated and loaded in PBS at a flow rate of 1.0 ml/min using a BioCad Sprint. 1.5 ml fractions were collected across the entire chromatography and the absorbance at 280 and 215 nM were monitored. The peak fractions were characterized via SDS-PAGE Silver staining, and only the most pure fractions were pooled. This material represented purified ZCYTO18-CEE polypeptide.

This purified material was finally subjected to a 4 ml Acti-Clean Etox (Sterogene) column to remove any remaining endotoxins. The sample was passed over the PBS equilibrated gravity column four times then the column was washed with a single 3 ml volume of PBS, which was pooled with the "cleaned" sample. The material was then 0.2 micron sterile filtered and stored at −80° C. until it was aliquoted.

On Western blotted, Coomassie Blue and Silver stained SDS-PAGE gels, the ZCYTO18-CEE polypeptide was two major bands and two mionor bands. The protein concentration of the purified material was performed by BCA analysis (Pierce, Rockford, Ill.) and the protein was aliquoted, and stored at −80° C. according to standard procedures. In a Western blot analysis, all bands were immunoreactive with a rabbit anti-ZCYTO18-peptide antibody (Example 16). The 4 bands likely represent different glycosylated forms of the ZCYTO18 polypeptide.

To prepare anti-EE Sepharose, a 100 ml bed volume of protein G-Sepharose (Pharmacia, Piscataway, N.J.) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma, St. Louis, Mo.), and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2HCl (Pierce, Rockford, Ill.) dissolved in TEA, was added to a final concentration of 36 mg/ml of protein G-Sepharose gel. The gel was rocked at room temperature for 45 min and the liquid was removed using the filter unit as described above. Nonspecific sites on the gel were then blocked by incubating for 10 min at room temperature with 5 volumes of 20 mM ethanolamine in 200 mM TEA. The gel was then washed with 5 volumes of PBS containing 0.02% sodium azide and stored in this solution at 4° C.

Example 10

Generation of Non-tagged ZCYTO18 Recombinant Adenovirus

The protein coding region of human ZCYTO18 (SEQ ID NO:1; SEQ ID NO:2) was amplified by PCR using primers that added FseI and AscI restriction sties at the 5' and 3' termini respectively. PCR primers ZC26665 (SEQ ID NO:20) and ZC26666 (SEQ ID NO:21) were used with pINCY template plasmid containing the full-length ZCYTO18 cDNA in a PCR reaction as follows: one cycle at 95° C. for 5 minutes; followed by 18 cycles at 95° C. for 0.5 min., 58° C. for 0.5 min., and 72° C. for 0.5 min.; followed by 72° C. for 7 min.; followed by a 4° C. soak. The PCR reaction product was loaded onto a 1.2% (low melt) SeaPlaque GTG (FMC, Rockland, Me.) gel in TAE buffer. The ZCYTO18 PCR product was excised from the gel and the gel slice melted at 70µ° C., extracted twice with an equal volume of Tris buffered phenol, and EtOH precipitated.

The 540 by ZCYTO18 PCR product was digested with FseI and AscI enzymes. The cDNA was isolated on a 1% low melt SeaPlaque GTG™ (FMC, Rockland, Me.) gel and was then excised from the gel and the gel slice melted at 70° C., extracted twice with an equal volume of Tris buffered phenol, and EtOH precipitated. The DNA was resuspended in 10 µl $H_2O$.

The ZCYTO18 cDNA was cloned into the FseI-AscI sites of a modified pAdTrack CMV (He, T-C. et al., *PNAS* 95:2509-2514, 1998). This construct contains the GFP marker gene. The CMV promoter driving GFP expression was replaced with the SV40 promoter and the SV40 polyadenylation signal was replaced with the human growth hormone polyadenylation signal. In addition, the native polylinker was replaced with FseI, EcoRV, and AscI sites. This modified form of pAdTrack CMV was named pZyTrack. Ligation was performed using the Fast-Link™ DNA ligation and screening kit (Epicentre Technologies, Madison, Wis.). Clones containing the ZCYTO18 insert were identified by standard mini prep analysis. The cloned ZCYTO18 cDNA was sequenced to verify no errors were introduced during PCR. In order to linearize the plasmid, approximately 5 µg of the pZyTrack ZCYTO18 plasmid was digested with PmeI. Approximately 1 µg of the linearized plasmid was cotransformed with 200 ng of supercoiled pAdEasy (He et al., supra.) into BJ5183 cells. The co-transformation was done using a Bio-Rad Gene Pulser at 2.5 kV, 200 ohms and 25mFa. The entire co-transformation was plated on 4 LB plates containing 25 µg/ml kanamycin. The smallest colonies were picked and expanded in LB/kanamycin and recombinant adenovirus DNA identified by standard DNA miniprep procedures. Digestion of the recombinant adenovirus DNA with FseI-AscI confirmed the presence of ZCYTO18. The recombinant adenovirus miniprep DNA was transformed into DH10B competent cells and DNA prepared using a Qiagen maxi prep kit as per kit instructions.

Transfection of 293a Cells with Recombinant DNA

Approximately 5 µg of recombinant adenoviral DNA was digested with PacI enzyme (New England Biolabs) for 3 hours at 37° C. in a reaction volume of 100 µl containing 20-30 U of PacI. The digested DNA was extracted twice with an equal volume of phenol/chloroform and precipitated with ethanol. The DNA pellet was resuspended in 5 µl distilled water. A T25 flask of QBI-293A cells (Quantum Biotechnologies, Inc. Montreal, Qc. Canada), inoculated the day before and grown to 60-70% confluence, were transfected with the PacI digested DNA. The PacI-digested DNA was diluted up to a total volume of 50 µl with sterile HBS (150 mM NaCl, 20 mM HEPES). In a separate tube, 25 DOTAP (Boehringer Mannheim, 1 mg/ml) was diluted to a total volume of 100 µl with HBS. The DNA was added to the DOTAP, mixed gently by pipeting up and down, and left at room temperature for 15 minutes. The media was removed from the 293A cells and washed with 5 ml serum-free MEMalpha (Gibco BRL) containing 1 mM Sodium Pyruvate (GibcoBRL), 0.1 mM MEM non-essential amino acids (GibcoBRL) and 25 mM HEPES buffer (GibcoBRL). 5 ml of serum-free MEM was added to the 293A cells and held at 37° C. The DNA/lipid mixture was added drop-wise to the T25 flask of 293A cells, mixed gently and incubated at 37° C. for 4 hours. After 4 hours the media containing the DNA/lipid mixture was aspirated off and replaced with 5 ml complete MEM containing 5% fetal bovine serum. The transfected cells were monitored for Green Fluorescent Protein (GFP) expression and formation of foci, i.e., viral plaques.

Seven days after transfection of 293A cells with the recombinant adenoviral DNA, the cells expressed the GFP protein and started to form foci. These foci are viral "plaques" and the crude viral lysate was collected by using a cell scraper to collect all of the 293A cells. The lysate was transferred to a 50 ml conical tube. To release most of the virus particles from the cells, three freeze/thaw cycles were done in a dry ice/ethanol bath and a 37° C. waterbath.

Amplification of Recombinant Adenovirus (rAdV)

The crude lysate was amplified (Primary)(1° amplification) to obtain a working "stock" of zsig45 rAdV lysate. Ten 10 cm plates of nearly confluent (80-90%) 293A cells were set up 20 hours previously, 200 ml of crude rAdV lysate added to each 10 cm plate and monitored for 48 to 72 hours looking for CPE under the white light microscope and expression of GFP under the fluorescent microscope. When all of the 293A cells showed CPE (Cytopathic Effect) this 1° stock lysate was collected and freeze/thaw cycles performed as described under Crude rAdV Lysate.

Secondary)(2° Amplification of zsig46 rAdV was obtained as follows: Twenty 15 cm tissue culture dishes of 293A cells were prepared so that the cells were 80-90% confluent. All but 20 mls of 5% MEM media was removed and each dish was inoculated with 300-500 ml 1° amplified rAdv lysate. After 48 hours the 293A cells were lysed from virus production and this lysate was collected into 250 ml polypropylene centrifuge bottles and the rAdV purified.

rAdV/cDNA Purification

NP-40 detergent was added to a final concentration of 0.5% to the bottles of crude lysate in order to lyse all cells. Bottles were placed on a rotating platform for 10 min. agitating as fast as possible without the bottles falling over. The debris was pelleted by centrifugation at 20,000×G for 15 minutes. The supernatant was transferred to 250 ml polycarbonate centrifuge bottles and 0.5 volumes of 20% PEG8000/2.5M NaCl solution added. The bottles were shaken overnight on ice. The bottles were centrifuged at 20,000×G for 15 minutes and supernatant discarded into a bleach solution. The white precipitate in two vertical lines along the wall of the bottle on either side of the spin mark is the precipitated virus/PEG. Using a sterile cell scraper, the precipitate from 2 bottles was resuspended in 2.5 ml PBS. The virus solution was placed in 2 ml microcentrifuge tubes and centrifuged at 14,000×G in the microfuge for 10 minutes to remove any additional cell debris. The supernatant from the 2 ml microcentrifuge tubes was transferred into a 15 ml polypropylene snapcap tube and adjusted to a density of 1.34 g/ml with cesium chloride (CsCl). The volume of the virus solution was estimated and 0.55 g/ml of CsCl added. The CsCl was dissolved and 1 ml of this solution weighed 1.34 g. The solution was transferred polycarbonate thick-walled centrifuge tubes 3.2 ml (Beckman #362305) and spin at 80,000 rpm (348,000 X G) for 3-4 hours at 25° C. in a Beckman Optima TLX microultracentrifuge with the TLA-100.4 rotor. The virus formed a white band. Using wide-bore pipette tips, the virus band was collected.

The virus from the gradient has a large amount of CsCl which must be removed before it can be used on cells. Pharmacia PD-10 columns prepacked with Sephadex G-25M (Pharmacia) were used to desalt the virus preparation. The column was equilibrated with 20 ml of PBS. The virus was loaded and allow it to run into the column. 5 ml of PBS was added to the column and fractions of 8-10 drops collected. The optical densities of 1:50 dilutions of each fraction was determined at 260 nm on a spectrophotometer. A clear absorbance peak was present between fractions 7-12. These fractions were pooled and the optical density (OD) of a 1:25 dilution determined A formula is used to convert OD into virus concentration: (OD at 260 nm)(25)($1.1 \times 10^{12}$)=virions/ml. The OD of a 1:25 dilution of the ZCYTO18 rAdV was 0.134, giving a virus concentration of $3.7 \times 10^{12}$ virions/ml.

To store the virus, glycerol was added to the purified virus to a final concentration of 15%, mixed gently but effectively, and stored in aliquots at −80° C.

Tissue Culture Infectious Dose at 50% CPE (TCID 50) Viral Titration Assay

A protocol developed by Quantum Biotechnologies, Inc. (Montreal, Qc. Canada) was followed to measure recombinant virus infectivity. Briefly, two 96-well tissue culture plates were seeded with $1 \times 10^4$ 293A cells per well in MEM containing 2% fetal bovine serum for each recombinant virus to be assayed. After 24 hours 10-fold dilutions of each virus from $1 \times 10^{-2}$ to $1 \times 10^{14}$ were made in MEM containing 2% fetal bovine serum. 100 µl of each dilution was placed in each of 20 wells. After 5 days at 37° C., wells were read either positive or negative for Cytopathic Effect (CPE) and a value for "Plaque Forming Units/ml" (PFU) is calculated.

$TCID_{50}$ formulation used was as per Quantum Biotechnologies, Inc., above. The titer (T) is determined from a plate where virus used is diluted from $10^{-2}$ to $10^{-14}$, and read 8 days after the infection. At each dilution a ratio (R) of positive wells for CPE per the total number of wells is determined.

To Calculate titer of the undiluted virus sample: the factor, "F"=1+d(S−0.5); where "S" is the sum of the ratios (R); and "d" is Log 10 of the dilution series, for example, "d" is equal to 1 for a ten-fold dilution series. The titer of the undiluted sample is $T=10^{(1+F)}=TCID_{50}$/ml. To convert $TCID_{50}$/ml to pfu/ml, 0.7 is subtracted from the exponent in the calculation for titer (T). The ZCYTO18 adenovirus had a titer of $2.8 \times 10^{11}$ pfu/ml.

Example 11

In vivo Affects of ZCYTO18 Polypeptide

Mice (female, C57B1, 8 weeks old; Charles River Labs, Kingston, N.Y.) were divided into three groups. On day 0, parental or ZCYTO18 adenovirus (Example 10) was administered to the first (n=8) and second (n=8) groups, respectively, via the tail vein, with each mouse receiving a dose of ~$1 \times 10^{11}$ particles in ±0.1 ml volume. The third group (n=8) received no treatment. On days 12, mice were weighed and blood was drawn from the mice. Samples were analyzed for complete blood count (CBC) and serum chemistry. Statistically significant elevations in neutrophil and platelet counts were detected in the blood samples from the ZCYTO18 adenovirus administered group relative to the parental adenovirus treated group. Also, at day 12 lymphocyte counts were significantly reduced from the ZCYTO18 adenovirus administered group relative to the parental adenovirus treated group, and they rebounded to normal levels by day 21. In addition, the ZCYTO18 adenovirus treated mice decreased in body weight, while parental adenovirus treated mice gained weight. The elevated platelet and neutrophil count, and the loss of body weight are still significant as compared to the control group. The liver chemistry test indicated the increased level of globulin and decreased level of albumin concentration, which is consistent with the observation of inflammatory response induced by TNF-.

The results suggested that ZCYTO18 affects hematopoiesis, i.e., blood cell formation in vivo. As such, ZCYTO18 could have biological activities affecting different blood precursors, progenitors or stem cells, and a resulting increase or decrease of certain differentiated blood cells in a specific lineage. For instance, ZCYTO18 appears to reduce lymphocytes, which is likely due to inhibition of the committed progenitor cells that give rise to lymphoid cells. This finding agrees with the inhibitory effects of ZCYTO18 on the proliferation and/or growth of myeloid stem cells (Example 23), supporting the notion that ZCYTO18 could play a role in anemia, infection, inflammation, and/or immune diseases by influencing blood cells involved in these process. Antagonists against ZCYTO18, such as antibodies or a soluble receptor antagonist could be used as therapeutic reagents in these diseases. It is also possible that ZCYTO18 directly affects the release and survival of platelets in peripheral blood or other vascularized tissues such as liver. That is, besides working through a hematopoisis loop (differentiation, proliferation of stem cells), zcyto18 might directly affect the release, stablization or depletion of platelets and neutrophils in peripheral blood or some target tissue and organs. ZCYTO18 also affects the number of granulocytes in the peripheral blood. Extramedullary sites of hematopoiesis (e.g. liver) are also targets for ZCYTO18 action.

Moreover, these experiments using ZCYTO18 adenovirus in mice suggest that ZCYTO18 over-expression increases the level of neutrophils and platelets in vivo. Although increasing neutrophils and platelets is desirable in certain therapeutic applications discussed herein, chronic elevation or increased reactivity of these cells could play a role in cardiovascular disease. Antagonists against ZCYTO18, such as antibodies or its soluble receptor, could be used as therapeutic reagents in these diseases. Although this may appear contradictory to the finding seen in K562 cells (Example 12), it is not uncommon to observe diverse activities of a particular protein in vitro versus in vivo. It is conceivable that there are other factors (such as cytokines and modifier genes) involved in the responses to ZCYTO18 in the whole animal system. Nevertheless, these data strongly support the involvement of ZCYTO18 in hematopoiesis. Thus, ZCYTO18 and its receptors are suitable reagents/targets for the diagnosis and treatment in variety of disorders, such as inflammation, immune disorders, infection, anemia, hematopoietic and other cancers, and the like.

Example 12

The ZCYTO18 Polypeptide Inhibits the Growth of K-562 Cells in A Cytotoxicity Assay The K-562 cell line (CRL-243, ATCC) has attained widespread use as a highly sensitive in vitro target for cytotoxicity assays. K-562 blasts are multipotential, hematopoietic malignant cells that spontaneously differentiate into recognizable progenitors of the erythrocytic, granulocytic and monocytic series (Lozzio, B B et al., *Proc. Soc. Exp. Biol. Med.* 166: 546-550, 1981).

K562 cells were plated at 5,000 cells/well in 96-well tissue culture clusters (Costar) in DMEM phenol-free growth medium (Life Technologies) supplemented with pyruvate and 10% serum (HyClone). Next day, human recombinant ZCYTO18 (Example 19), BSA control or retinoic acid (known to be cytotoxic to K562 cells) were added. Seventy-two hours later, the vital stain MTT (Sigma, St Louis, Mo.), a widely used indicator of mitochondrial activity and cell growth, was added to the cells at a final concentration of 0.5 mg/ml. MTT is converted to a purple formazan derivative by mitochondrial dehydrogenases. Four hours later, converted MTT was solubilized by adding an equal volume of acidic isopropanol (0.04N HCl in absolute isopropanol) to the wells. Absorbance was measured at 570 nm, with background subtraction at 650 nm. In this experimental setting, absorbance reflects cell viability. Results shown in Table 7 are expressed as % cytotoxicity.

TABLE 7

| Agent | Concentration | % Cytotoxicity |
|---|---|---|
| BSA Control | 1 ug/ml | 1.3 |
| Retinoic acid | 100 uM | 62 |
| ZCYTO18 | 100 ng/ml | 16.2 |
| ZCYTO18 | 300 ng/ml | 32 |

The results indicate that ZCYTO18 may affect myeloid stem cells. Myeloid stem cells are daughter cells of the universal blood stem cells. They are progenitors of erythrocytes, monocytes (or migrated macrophages), neutrophil, basophil, and eosinophils. Since K-562 blasts differentiate into progenitors of the erythrocytic, granulocytic and monocytic series, they are considered a model for myeloid stem cells. Thus, the results demonstrate that ZCYTO18 has an inhibitory activity on the proliferation and/or growth of a promyelocytic tumor cell line. Thus ZCYTO18 could play a role in anemia, infection, inflammation, and/or immune diseases. In addition, an antagonist against ZCYTO18, such as antibodies or a soluble receptor antagonist, could be used to block ZCYTO18's activity on myeloid stem cells, or as therapeutic reagents in diseases such as anemia, infection, inflammation, and/or immune diseases. However, as ZCYTO18 exhibits cytotoxicity on tumor cells, it can be used directly or in combination with other cytokines as an anti-tumor agent as an anti-tumor agent.

Example 13

Human Zcytor16 Tissue Distribution in Tissue Panels Using Northern Blot and PCR A. Human Zcytor16 Tissue Distribution Using Northern Blot and Dot Blot Commonly owned, human zcytor16 (SEQ ID NO:32, and SEQ ID NO:33) (PCT International Application No. PCT/US00/32703, filed on Dec. 1, 2000) is a naturally-expressed soluble receptor antagonist of ZCYTO18. Northern blot analysis was performed using Human Multiple Tissue Northern Blots I, II, III (Clontech) and an in house generated U-937 northern blot. U-937 is a human promonocytic blast cell line. The cDNA probe was generated using oligos ZC25,963 (SEQ ID NO:24) and ZC28,354 (SEQ ID NO:25). The PCR conditions were as follows: 94° for 1 minute; 30 cycles of 94°, 15 seconds; 60°, 30 seconds; 72°, 30 seconds and a final extension for 5 minutes at 72°. The 364 bp product was gel purified by gel electrophoresis on a 1% TBE gel and the band was excised with a razor blade. The cDNA was extracted from the agarose using the QlAquick Gel Extraction Kit (Qiagen). 94 ng of this fragment was radioactively labeled with $^{32}$P-dCTP using Rediprime II (Amersham), a random prime labeling system, according to the manufacturer's specifications. Unincorporated radioactivity was removed using a Nuc-Trap column (Stratagene) according to manufacturer's instructions. Blots were prehybridized at 65° for 3 hours in ExpressHyb (Clontech) solution. Blots were hybridized overnight at 65° in Expresshyb solution containing $1.0 \times 10^6$ cpm/ml of labeled probe, 0.1 mg/ml of salmon sperm DNA and 0.5 μg/ml of human cot-1 DNA. Blots were washed in 2×SSC, 0.1% SDS at room temperature with several solution changes then washed in 0.1×SSC. 0.1% SDS at 55° for 30 minutes twice. Transcripts of approximately 1.6 kb and 3.0 kb size were detected in spleen and placenta, but not other tissues examined. The same sized transcripts plus an additional approximate 1.2 kb transcript was detected in U-937 cell line.

B. Tissue Distribution in Tissue cDNA Panels Using PCR

A panel of cDNAs from human tissues was screened for zcytor16 expression using PCR. The panel was made in-house and contained 94 marathon cDNA and cDNA samples from various normal and cancerous human tissues and cell lines are shown in Table 8, below. The cDNAs came from in-house libraries or marathon cDNAs from in-house RNA preps, Clontech RNA, or Invitrogen RNA. The marathon cDNAs were made using the marathon-Ready™ kit (Clontech, Palo Alto, Calif.) and QC tested with clathrin primers ZC21195 (SEQ ID NO:26) and ZC21196 (SEQ ID NO:27) and then diluted based on the intensity of the clathrin band. To assure quality of the panel samples, three tests for quality control (QC) were run: (1) To assess the RNA quality used for the libraries, the in-house cDNAs were tested for average insert size by PCR with vector oligos that were specific for the vector sequences for an individual cDNA library; (2) Standardization of the concentration of the cDNA in panel samples was achieved using standard PCR methods to amplify full length alpha tubulin or G3PDH cDNA using a 5' vector oligo ZC14,063 (SEQ ID NO:28) and 3' alpha tubulin specific oligo primer ZC17,574 (SEQ ID NO:29) or 3' G3PDH specific oligo primer ZC17,600 (SEQ ID NO:30); and (3) a sample was sent to sequencing to check for possible ribosomal or mitochondrial DNA contamination. The panel was set up in a 96-well format that included a human genomic DNA (Clontech, Palo Alto, Calif.) positive control sample. Each well contained approximately 0.2-100 pg/μl of cDNA. The PCR reactions were set up using oligos ZC25,963 (SEQ ID NO:24) and ZC27,659 (SEQ ID NO:25), Advantage 2 DNA Polymerase Mix (Clontech) and Rediload dye (Research Genetics, Inc., Huntsville, Ala.). The amplification was carried out as follow: 1 cycle at 94° C. for 2 minutes, 30 cycles of 94° C. for 20 seconds, 58° C. for 30 seconds and 72° C. for1 minute, followed by 1 cycle at 72° C. for 5 minutes. About 10 μl of the PCR reaction product was subjected to standard Agarose gel electrophoresis using a 2% agarose gel. The correct predicted DNA fragment size was not observed in any tissue or cell line. Subsequent experiments showing expression of zcytor16 indicated that the negative results from this panel were likely due to the primers used.

TABLE 8

| Tissue/Cell line | #samples | Tissue/Cell line | #samples |
|---|---|---|---|
| Adrenal gland | 1 | Bone marrow | 3 |
| Bladder | 1 | Fetal brain | 3 |
| Bone Marrow | 1 | Islet | 2 |
| Brain | 1 | Prostate | 3 |
| Cervix | 1 | RPMI #1788 (ATCC # CCL-156) | 2 |
| Colon | 1 | Testis | 4 |
| Fetal brain | 1 | Thyroid | 2 |
| Fetal heart | 1 | WI38 (ATCC # CCL-75 | 2 |
| Fetal kidney | 1 | ARIP (ATCC # CRL-1674 - rat) | 1 |
| Fetal liver | 1 | HaCat - human keratinocytes | 1 |
| Fetal lung | 1 | HPV (ATCC # CRL-2221) | 1 |
| Fetal muscle | 1 | Adrenal gland | 1 |
| Fetal skin | 1 | Prostate SM | 2 |
| Heart | 2 | CD3+ selected PBMC's Ionomycin + PMA stimulated | 1 |
| K562 (ATCC # CCL-243) | 1 | HPVS (ATCC # CRL-2221) - selected | 1 |
| Kidney | 1 | Heart | 1 |
| Liver | 1 | Pituitary | 1 |
| Lung | 1 | Placenta | 2 |
| Lymph node | 1 | Salivary gland | 1 |
| Melanoma | 1 | HL60 (ATCC # CCL-240) | 3 |
| Pancreas | 1 | Platelet | 1 |
| Pituitary | 1 | HBL-100 | 1 |
| Placenta | 1 | Renal mesangial | 1 |
| Prostate | 1 | T-cell | 1 |
| Rectum | 1 | Neutrophil | 1 |
| Salivary Gland | 1 | MPC | 1 |
| Skeletal muscle | 1 | Hut-102 (ATCC # TIB-162) | 1 |
| Small intestine | 1 | Endothelial | 1 |
| Spinal cord | 1 | HepG2 (ATCC # HB-8065) | 1 |
| Spleen | 1 | Fibroblast | 1 |
| Stomach | 1 | E. Histo | 1 |
| Testis | 2 | | |
| Thymus | 1 | | |
| Thyroid | 1 | | |
| Trachea | 1 | | |
| Uterus | 1 | | |
| Esophagus tumor | 1 | | |
| Gastric tumor | 1 | | |
| Kidney tumor | 1 | | |
| Liver tumor | 1 | | |
| Lung tumor | 1 | | |
| Ovarian tumor | 1 | | |
| Rectal tumor | 1 | | |
| Uterus tumor | 1 | | |

An additional panel of cDNAs from human tissues was screened for zcytor16 expression using PCR. This panel was made in-house and contained 77 marathon cDNA and cDNA samples from various normal and cancerous human tissues and cell lines are shown in Table 9, below. Aside from the PCR reaction, the assay was carried out as per above. The PCR reactions were set up using oligos ZC25,963 (SEQ ID NO:24) and ZC25,964 (SEQ ID NO:31), Advantage 2 DNA Polymerase Mix (Clontech) and Rediload dye (Research Genetics, Inc., Huntsville, Ala.). The amplification was carried out as follow: 1 cycle at 94° C. for 1 minute, 38 cycles of 94° C. for 10 seconds, 60° C. for 30 seconds and 72° C. for 30 seconds, followed by 1 cycle at 72° C. for 5 minutes. The correct predicted DNA fragment size was observed in bone marrow, fetal heart, fetal kidney, fetal muscle, fetal skin, heart, mammary gland, placenta, salivary gland, skeletal muscle, small intestine, spinal cord, spleen, kidney, fetal brain, esophageal tumor, uterine tumor, stomach tumor, ovarian tumor, rectal tumor, lung tumor and RPMI-1788 (a B-lymphocyte cell line). Zcytor16 expression was not observed in the other tissues and cell lines tested in this panel. The expression pattern of zcytor16 shows expression in certain tissue-specific tumors especially, e.g., ovarian cancer, stomach cancer, uterine cancer, rectal cancer, lung cancer and esophageal cancer, where zcytor16 is not expressed in normal tissue, but is expressed in the tumor tissue. One of skill in the art would recognize that the natural ligand, CYTO18, and receptor binding fragments of ZCYTO18 of the present invention can be used as a diagnostic to detect cancer, or cancer tissue in a biopsy, tissue, or histologic sample, particularly e.g., ovarian cancer, stomach cancer, uterine cancer, rectal cancer, lung cancer and esophageal cancer tissue. Such diagnostic uses for the molecules of the present invention are known in the art and described herein.

In addition, because the expression pattern of zcytor16, one of ZCYTO18's receptors, shows expression in certain specific tissues as well as tissue-specific tumors, binding partners including the natural ligand, ZCYTO18, can also be used as a diagnostic to detect specific tissues (normal or abnormal), cancer, or cancer tissue in a biopsy, tissue, or histologic sample, where ZCYTO18 receptors are expressed, and particularly e.g., ovarian cancer, stomach cancer, uterine cancer, rectal cancer, lung cancer and esophageal cancer tissue. ZCYTO18 can also be used to target other tissues wherein its receptors, e.g., zcytor16 and zcytor11 (Commonly owned U.S. Pat. No. 5,965,704) are expressed. Moreover, such binding partners could be conjugated to chemotherapeutic agents, toxic moieties and the like to target therapy to the site of a tumor or diseased tissue. Such diagnostic and targeted therapy uses are known in the art and described herein.

A commercial 1st strand cDNA panel (Human Blood Fractions MTC Panel, Clontech, Palo Alto, Calif.) was also assayed as above. The panel contained the following samples: mononuclear cells, activated mononuclear cells, resting CD4+ cells, activated CD4+ cells, resting CD8+ cells, activated CD8+ cells, resting CD14+ cells, resting CD19+ cells and activated CD19+ cells. Activated CD4+ cells and activated CD19+ cells showed zcytor16 expression, whereas the other cells tested, including resting CD4+ cells and resting CD19+ cells, did not.

TABLE 9

| Tissue | #samples | Tissue | #samples |
|---|---|---|---|
| adrenal gland | 1 | bladder | 1 |
| bone marrow | 3 | brain | 2 |
| cervix | 1 | colon | 1 |
| fetal brain | 3 | fetal heart | 2 |
| fetal kidney | 1 | fetal liver | 2 |
| fetal lung | 1 | fetal skin | 1 |
| heart | 2 | fetal muscle | 1 |
| kidney | 2 | liver | 1 |
| lung | 1 | lymph node | 1 |
| mammary gland | 1 | melanoma | 1 |
| ovary | 1 | pancreas | 1 |
| pituitary | 2 | placenta | 3 |
| prostate | 3 | rectum | 1 |
| salivary gland | 2 | skeletal muscle | 1 |
| small intestine | 1 | spinal cord | 2 |
| spleen | 1 | uterus | 1 |
| stomach | 1 | adipocyte library | 1 |
| testis | 5 | islet | 1 |
| thymus | 1 | prostate SMC | 1 |
| thyroid | 2 | RPMI 1788 | 1 |
| trachea | 1 | WI38 | 1 |
| esophageal tumor | 1 | lung tumor | 1 |
| liver tumor | 1 | ovarian tumor | 1 |
| rectal tumor | 1 | stomach tumor | 1 |

TABLE 9-continued

| Tissue | #samples | Tissue | #samples |
|---|---|---|---|
| uterine tumor | 2 | CD3+ library | 1 |
| HaCAT library | 1 | HPV library | 1 |
| HPVS library | 1 | MG63 library | 1 |
| K562 | 1 | | |

C. Tissue Distribution in Human Tissue and Cell Line RNA Panels Using RT-PCR

A panel of RNAs from human cell lines was screened for zcytor16 expression using RT-PCR. The panels were made in house and contained 84 RNAs from various normal and cancerous human tissues and cell lines as shown in Tables 10-13 below. The RNAs were made from in house or purchased tissues and cell lines using the RNAeasy Midi or Mini Kit (Qiagen, Valencia, Calif.). The panel was set up in a 96-well format with 100 ngs of RNA per sample. The RT-PCR reactions were set up using oligos ZC25,963 (SEQ ID NO:24) and ZC25,964 (SEQ ID NO:31), Rediload dye and SUPERSCRIPT One Step RT-PCR System (Life Technologies, Gaithersburg, Md.). The amplification was carried out as follows: one cycle at 55° for 30 minutes followed by 40 cycles of 94°, 15 seconds; 59°, 30 seconds; 72°, 30 seconds; then ended with a final extension at 72° for 5 minutes. 8 to 10 μls of the PCR reaction product was subjected to standard Agarose gel electrophoresis using a 4% agarose gel. The correct predicted cDNA fragment size of 184 bps was observed in cell lines U-937, HL-60, ARPE-19, HaCat#1, HaCat#2, HaCat#3, and HaCat#4; bladder, cancerous breast, normal breast adjacent to a cancer, bronchus, colon, ulcerative colitis colon, duodenum, endometrium, esophagus, gastro-esophageal, heart left ventricle, heart ventricle, ileum, kidney, lung, lymph node, lymphoma, mammary adenoma, mammary gland, cancerous ovary, pancreas, parotid and skin, spleen lymphoma and small bowel. Zcytor16 expression was not observed in the other tissues and cell lines tested in this panel.

Zcytor16 is detectably expressed by PCR in normal tissues: such as, the digestive system, e.g., esophagus, gastro-esophageal, pancreas, duodenum, ileum, colon, small bowel; the female reproductive system, e.g., mammary gland, endometrium, breast (adjacent to cancerous tissues); and others systems, e.g., lymph nodes, skin, parotid, bladder, bronchus, heart ventricles, and kidney. Moreover, Zcytor16 is detectably expressed by PCR in several human tumors: such as tumors associated with female reproductive tissues e.g., mammary adenoma, ovary cancer, uterine cancer, other breast cancers; and other tissues such as lymphoma, stomach tumor, and lung tumor. The expression of zcytor16 is found in normal tissues of female reproductive organs, and in some tumors associated with these organs. As such, a ligand for zcytor16, such as ZCYTO18, or a receptor-binding fragment thereof, can serve as a marker for these tumors wherein the zcytor16 may be over-expressed. Several cancers positive for zcytor16 are associated with ectodermal/epithelial origin (mammary adenoma, and other breast cancers). Hence, ligand for zcytor16, such as ZCYTO18, or a receptor-binding fragment thereof, can serve as a marker for epithelial tissue, such as epithelial tissues in the digestive system and female reproductive organs (e.g., endometrial tissue, columnar epithelium), as well as cancers involving epithelial tissues. Moreover, in a preferred embodiment, ZCYTO18, or a receptor-binding fragment thereof, can serve as a marker for certain tissue-specific tumors especially, e.g., ovarian cancer, stomach cancer, uterine cancer, rectal cancer, lung cancer and esophageal cancer, where it's receptor zcytor16 is not expressed in normal tissue, but is expressed in the tumor tissue. Use of polynucleotides, polypeptides, and antibodies of the present invention for diagnostic purposes are known in the art, and disclosed herein.

TABLE 10

| Tissue | #samples | Tissue | #samples |
|---|---|---|---|
| adrenal gland | 6 | duodenum | 1 |
| bladder | 3 | endometrium | 5 |
| brain | 2 | cancerous endometrium | 1 |
| brain meningioma | 1 | gastric cancer | 1 |
| breast | 1 | esophagus | 7 |
| cancerous breast | 4 | gastro-esophageal | 1 |
| normal breast adjacent to cancer | 5 | heart aorta | 1 |
| bronchus | 3 | heart left ventricle | 4 |
| colon | 15 | heart right ventricle | 2 |
| cancerous colon | 1 | heart ventricle | 1 |
| normal colon adjacent to cancer | 1 | ileum | 3 |
| ulcerative colitis colon | 1 | kidney | 15 |
| | | cancerous kidney | 1 |

TABLE 11

| Tissue/Cell Line | #samples | Tissue/Cell Line | #samples |
|---|---|---|---|
| 293 | 1 | HBL-100 | 1 |
| C32 | 1 | Hs-294T | 1 |
| HaCat#1 | 1 | Molt4 | 1 |
| HaCat#2 | 1 | RPMI | 1 |
| HaCat#3 | 1 | U-937 | 1 |
| HaCat#4 | 1 | A-375 | 1 |
| WI-38 | 1 | HCT-15 | 1 |
| WI-38 + 2 um ionomycin #1 | 1 | HT-29 | 1 |
| WI-38 + 2 um ionomycin #2 | 1 | MRC-5 | 1 |
| WI-38 + 5 um ionomycin#1 | 1 | RPT-1 | 1 |
| WI-38 + 5 um ionomycin#2 | 1 | RPT-2 | 1 |
| Caco-2, | 1 | WM-115 | 1 |
| Caco-2, differentiated | 1 | A-431 | 1 |
| DLD-1 | 1 | WERI-Rb-1 | 1 |
| HRE | 1 | HEL-92.1.7 | 1 |
| HRCE | 1 | HuH-7 | 1 |
| MCF7 | 1 | MV-4-11 | 1 |
| PC-3 | 1 | U-138 | 1 |
| TF-1 | 1 | CCRF-CEM | 1 |
| 5637 | 1 | Y-79 | 1 |
| 143B | 1 | A-549 | 1 |
| ME-180 | 1 | EL-4 | 1 |
| prostate epithelia | 1 | HeLa 229 | 1 |
| U-2 OS | 1 | HUT 78 | 1 |
| T-47D | 1 | NCI-H69 | 1 |
| Mg-63 | 1 | SaOS2 | 1 |
| Raji | 1 | USMC | 1 |
| U-373 MG | 1 | UASMC | 2 |
| A-172 | 1 | AoSMC | 1 |
| CRL-1964 | 1 | UtSMC | 1 |
| CRL-1964 + butryic acid | 1 | HepG2 | 1 |
| HUVEC | 1 | HepG2-IL6 | 1 |
| SK-Hep-1 | 1 | NHEK#1 | 1 |
| SK-Lu-1 | 1 | NHEK#2 | 1 |
| Sk-MEL-2 | 1 | NHEK#3 | 1 |
| K562 | 1 | NHEK#4 | 1 |
| BeWo | 1 | ARPE-19 | 1 |
| FHS74.Int | 1 | G-361 | 1 |
| HL-60 | 1 | HISM | 1 |
| Malme 3M | 1 | 3AsubE | 1 |
| FHC | 1 | INT407 | 1 |
| HREC | 1 | | |

TABLE 12

| Tissue | #samples | Tissue | #samples |
|---|---|---|---|
| liver | 10 | lung | 13 |
| lymph node | 1 | cancerous lung | 2 |
| lymphoma | 4 | normal lung adjacent to cancer | 1 |
| mammary adenoma | 1 | muscle | 3 |
| mammary gland | 3 | neuroblastoma | 1 |
| melinorioma | 1 | omentum | 2 |
| osteogenic sarcoma | 2 | ovary | 6 |
| pancreas | 4 | cancerous ovary | 2 |
| skin | 5 | parotid | 7 |
| sarcoma | 2 | salivary gland | 4 |

TABLE 13

| Tissue | #samples | Tissue | #samples |
|---|---|---|---|
| small bowel | 10 | uterus | 11 |
| spleen | 3 | uterine cancer | 1 |
| spleen lymphoma | 1 | thyroid | 9 |
| stomach | 13 | | |
| stomach cancer | 1 | | |

Example 14

Human Zcytor11 Tissue Distribution in Tissue Panels Using Northern Blot and PCR

A. Human Zcytor11 Tissue Distribution in Tissue Panels Using PCR

A panel of cDNAs from human tissues was screened for zcytor11 expression using PCR. Commonly owned, human zcytor11 (SEQ ID NO:18, and SEQ ID NO:19) (U.S. Pat. No. 5,965,704) is a receptor for ZCYTO18. The panel was made in-house and contained 94 marathon cDNA and cDNA samples from various normal and cancerous human tissues and cell lines are shown in Table 9 above. Aside from the PCR reaction, the method used was as shown in Example 13. The PCR reactions were set up using oligos ZC14,666 (SEQ ID NO:22) and ZC14,742 (SEQ ID NO:23), Advantage 2 cDNA polymerase mix (Clontech, Palo Alto, Calif.), and Rediload dye (Research Genetics, Inc., Huntsville, Ala.). The amplification was carried out as follows: 1 cycle at 94° C. for 2 minutes, 40 cycles of 94° C. for 15 seconds, 51° C. for 30 seconds and 72° C. for 30 seconds, followed by 1 cycle at 72° C. for 7 minutes. The correct predicted DNA fragment size was observed in bladder, brain, cervix, colon, fetal brain, fetal heart, fetal kidney, fetal liver, fetal lung, fetal skin, heart, kidney, liver, lung, melanoma, ovary, pancreas, placenta, prostate, rectum, salivary gland, small intestine, testis, thymus, trachea, spinal cord, thyroid, lung tumor, ovarian tumor, rectal tumor, and stomach tumor. Zcytor11 expression was not observed in the other tissues and cell lines tested in this panel.

A commercial 1st strand cDNA panel (Human Blood Fractions MTC Panel, Clontech, Palo Alto, Calif.) was also assayed as above. The panel contained the following samples: mononuclear cells, activated mononuclear cells, resting CD4+ cells, activated CD4+ cells, resting CD8+ cells, activated CD8+ cells, resting CD14+ cells, resting CD19+ cells and activated CD19+ cells. All samples except activated CD8+ and Activated CD19+ showed expression of zcytor11.

B. Tissue Distribution of Zcytor11 in Human Cell Line and Tissue Panels Using RT-PCR A panel of RNAs from human cell lines was screened for zcytor11 expression using RT-PCR. The panels were made in house and contained 84 RNAs from various normal and cancerous human tissues and cell lines as shown in Tables 10-13 above. The RNAs were made from in house or purchased tissues and cell lines using the RNAeasy Midi or Mini Kit (Qiagen, Valencia, Calif.). The panel was set up in a 96-well format with 100 ngs of RNA per sample. The RT-PCR reactions were set up using oligos ZC14,666 (SEQ ID NO:22) and ZC14,742 (SEQ ID NO:23), Rediload dye and SUPERSCRIPT One Step RT-PCR System(Life Technologies, Gaithersburg, Md.). The amplification was carried out as follows: one cycle at 50° for 30 minutes followed by 45 cycles of 94°, 15 seconds; 52°, 30 seconds; 72°, 30 seconds; then ended with a final extension at 72° for 7 minutes. 8 to 10 uls of the PCR reaction product was subjected to standard Agarose gel electrophoresis using a 4% agarose gel. The correct predicted cDNA fragment size was observed in adrenal gland, bladder, breast, bronchus, normal colon, colon cancer, duodenum, endometrium, esophagus, gastic cancer, gastro-esophageal cancer, heart ventricle, ileum, normal kidney, kidney cancer, liver, lung, lymph node, pancreas, parotid, skin, small bowel, stomach, thyroid, and uterus. Cell lines showing expression of zcytor11 were A-431, differentiated CaCO2, DLD-1, HBL-100, HCT-15, HepG2, HepG2+IL6, HuH7, and NHEK #1-4. Zcytor11 expression was not observed in the other tissues and cell lines tested in this panel.

In addition, because the expression pattern of zcytor11, one of ZCYTO18's receptors, shows expression in certain specific tissues, binding partners including the natural ligand, ZCYTO18, can also be used as a diagnostic to detect specific tissues (normal or abnormal), cancer, or cancer tissue in a biopsy, tissue, or histologic sample, particularly in tissues where ZCYTO18 receptors are expressed. ZCYTO18 can also be used to target other tissues wherein its receptors, e.g., zcytor16 and zcytor11 are expressed. Moreover, such binding partners could be conjugated to chemotherapeutic agents, toxic moieties and the like to target therapy to the site of a tumor or diseased tissue. Such diagnostic and targeted therapy uses are known in the art and described herein.

The expression patterns of zcytor11 (above) and zcytor16 (Example 13, and Example 15) indicated target tissues and cell types for the action of ZCYTO18, and hence ZCYTO18 antagonists. The zcytor11 expression generally overlapped with zcytor16 expression in three physiologic systems: digestive system, female reproductive system, and immune system. Moreover, the expression pattern of the receptor (zcytor11) indicated that a ZCYTO18 antagonist such as zcytor16 would have therapeutic application for human disease in at least two areas: inflammation (e.g., IBD, Chron's disease, pancreatitis) and cancer (e.g., ovary, colon). That is, the polynucleotides, polypeptides and antibodies of the present invention can be used to antagonize the inflammatory, and other cytokine-induced effects of ZCYTO18 interaction with the cells expressing the zcytor11 receptor.

Moreover, the expression of zcytor11 appeared to be down-regulated or absent in an ulcerative colitis tissue, HepG2 liver cell line induced by IL-6, activated CD8+ T-cells and CD19+ B-cells. However, zcytor16 appeared to be upregulated in activated CD19+ B-cells (Example 12), while zcytor11 is downregulated in activated CD19+ cells, as compared to the resting CD19+ cells (above). The expression of zcytor11 and zcytor16 has a reciprocal correlation in this case. These RT-PCR experiments demonstrate that CD19+ peripheral blood cells, B lymphocytes, express receptors for ZCYTO18, namely zcytor11 and zcytor16. Furthermore B cells display regulated expression of zcytor11 and zcytor16. B-lymphocytes activated with mitogens decrease expression of zcytor11 and increase expression of zcytor16. This represents feedback inhibition that would serve to dampen the activity of ZCYTO18 on B cells and other cells as well. Soluble zcytor16 would act as an antagonist to neutralize the effects of ZCYTO18 on B cells. This would be beneficial in diseases where B cells are the key players: Autoimmune diseases including systemic lupus erythmatosus (SLE), myasthenia gravis, immune complex disease, and B-cell cancers that are exacerbated by ZCYTO18. Also autoimmune diseases where B cells contribute to the disease pathology would be targets for zcytor16 therapy: Multiple sclerosis, inflammatory bowel disease (IBD) and rheumatoid arthritis are examples. Zcytor16 therapy would be beneficial to dampen or inhibit B cells producing IgE in atopic diseases including asthma, allergy and atopic dermatitis where the production of IgE contributes to the pathogenesis of disease.

B cell malignancies may exhibit a loss of the "feedback inhibition" described above. Administration of zcytor16 would restore control of ZCYTO18 signaling and inhibit B cell tumor growth. The administration of zcytor16 following surgical resection or chemotherapy may be useful to treat minimal residual disease in patients with B cell malignancies. The loss of regulation may lead to sustained or increased expression of zcytor11. Thus creating a target for therapeutic monoclonal antibodies targeting zcytor11.

Example 15

Identification of Cells Expressing Zcytor16 Using In Situ Hybridization

Specific human tissues were isolated and screened for zcytor16 expression by in situ hybridization. Various human tissues prepared, sectioned and subjected to in situ hybridization included cartilage, colon, appendix, intestine, fetal liver, lung, lymph node, lymphoma, ovary, pancreas, placenta, prostate, skin, spleen, and thymus. The tissues were fixed in 10% buffered formalin and blocked in paraffin using standard techniques. Tissues were sectioned at 4 to 8 microns. Tissues were prepared using a standard protocol ("Development of non-isotopic in situ hybridization" at The Laboratory of Experimental Pathology (LEP), NIEHS, Research Triangle Park, NC). Briefly, tissue sections were deparaffinized with HistoClear (National Diagnostics, Atlanta, GA) and then dehydrated with ethanol. Next they were digested with Proteinase K (50 µg/ml) (Boehringer Diagnostics, Indianapolis, IN) at 37° C. for 2 to 7 minutes. This step was followed by acetylation and re-hydration of the tissues.

One in situ probe was designed against the human zcytor16 sequence (nucleotide 1-693 of SEQ ID NO:32), and isolated from a plasmid containing SEQ ID NO:32 using standard methods. T3 RNA polymerase was used to generate an anti-sense probe. The probe was labeled with digoxigenin (Boehringer) using an In Vitro transcription System (Promega, Madison, Wis.) as per manufacturer's instruction.

In situ hybridization was performed with a digoxigenin-labeled zcytor16 probe (above). The probe was added to the slides at a concentration of 1 to 5 pmol/ml for 12 to 16 hours at 62.5° C. Slides were subsequently washed in 2×SSC and 0.1×SSC at 55° C. The signals were amplified using tyramide signal amplification (TSA) (TSA, in situ indirect kit; NEN) and visualized with Vector Red substrate kit (Vector Lab) as per manufacturer's instructions. The slides were then counter-stained with hematoxylin (Vector Laboratories, Burlingame, Calif.).

Signals were observed in several tissues tested: The lymph node, plasma cells and other mononuclear cells in peripheral tissues were strongly positive. Most cells in the lymphatic nodule were negative. In lymphoma samples, positive signals were seen in the mitotic and multinuclear cells. In spleen, positive signals were seen in scattered mononuclear cells at the periphery of follicles were positive. In thymus, positive signals were seen in scattered mononuclear cells in both cortex and medulla were positive. In fetal liver, a strong signal was observed in a mixed population of mononuclear cells in sinusoid spaces. A subset of hepatocytes might also have been positive. In the inflamed appendix, mononuclear cells in peyer's patch and infiltration sites were positive. In intestine, some plasma cells and ganglia nerve cells were positive. In normal lung, zcytor16 was expressed in alveolar epithelium and mononuclear cells in interstitial tissue and circulation. In the lung carcinoma tissue, a strong signal was observed in mostly plasma cells and some other mononuclear cells in peripheral of lymphatic aggregates. In ovary carcinoma, epithelium cells were strongly positive. Some interstitial cells, most likely the mononuclear cells, were also positive. There was no signal observed in the normal ovary. In both normal and pancreatitis pancreas samples, acinar cells and some mononuclear cells in the mesentery were positive. In the early term (8 weeks) placenta, signal was observed in trophoblasts. In skin, some mononuclear cells in the inflamed infiltrates in the superficial dermis were positive. Keratinocytes were also weakly positive. In prostate carcinoma, scatted mononuclear cells in interstitial tissues were positive. In articular cartilage, chondrocytes were positive. Other tissues tested including normal ovary and a colon adenocarcinoma were negative.

In summary, the in situ data was consistent with expression data described above for the zcytor16. Zcytor16 expression was observed predominately in mononuclear cells, and a subset of epithelium was also positive. These results confirmed the presence of zcytor16 expression in immune cells and point toward a role in inflammation, autoimmune disease, or other immune function, for example, in binding pro-inflammatory cytokines, including but not limited to ZCYTO18. Moreover, detection of zcytor16 expression can be used for example as an marker for mononuclear cells in histologic samples.

Zcytor16 is expressed in mononuclear cells, including normal tissues (lymph nodes, spleen, thymus, pancreas and fetal liver, lung), and abnormal tissues (inflamed appendix, lung carcinoma, ovary carcinoma, pancreatitis, inflamed skin, and prostate carcinoma). It is notable that plasma cells in the lymph node, intestine, and lung carcinoma are positive for zcytor16. Plasma cells are immunologically activated lymphocytes responsible for antibody synthesis. In addition, ZCYTO18, is expressed in activated T cells. In addition, the expression of zcytor16 is detected only in activated (but not in resting) CD4+ and CD19+ cells (Example 13). Thus, zcytor16 can be used as a marker for or as a target in isolating certain lymphocytes, such as mononuclear leucocytes and limited type of activated leucocytes, such as activated CD4+ and CD19+.

Furthermore, the presence of zcytor16 expression in activated immune cells such as activated CD4+ and CD19+ cells showed that zcytor16 may be involved in the body's immune defensive reactions against foreign invaders: such as microorganisms and cell debris, and could play a role in immune responses during inflammation and cancer formation.

Moreover, as discussed herein, epithelium form several tissues was positive for zcytor16 expression, such as hepatocytes (endoderm-derived epithelia), lung alveolar epithelium (endoderm-derived epithelia), and ovary carcinoma epithelium (mesoderm-derived epithelium). The epithelium expression of zcytor16 could be altered in inflammatory responses and/or cancerous states in liver and lung. Thus, ligand for zcytor16, such as ZCYTO18, or a receptor-binding fragment thereof, could be used as marker to monitor changes in these tissues as a result of inflammation or cancer. Moreover, analysis of zcytor16 in situ expression showed that normal ovary epithelium is negative for zcytor16 expression, while it is strongly positive in ovary carcinoma epithelium providing further evidence that ZCYTO18 polypeptides, or a receptor-binding fragment thereof, can be used as a diagnostic marker and/or therapeutic target for the diagnosis and treatment of ovarian cancers, and ovary carcinoma, as described herein.

Zcytor16 was also detected in other tissues, such as acinar cells in pancreas (normal and pancreatitis tissues), trophoblasts in placenta (ectoderm-derived), chondrocytes in cartilage (mesoderm-derived), and ganglia cells in intestine (ectoderm-derived). As such, zcytor16 may be involved in differentiation and/or normal functions of corresponding cells in these organs. As such, potential utilities of zcytor16 include maintenance of normal metabolism and pregnancy, bone formation/homeostasis, and physiological function of intestine, and the like.

Example 16 huZCYTO18 Anti-Peptide Antibodies

Polyclonal anti-peptide antibodies were prepared by immunizing two female New Zealand white rabbits with the peptide, huZCYTO18-1 (SEQ ID NO:34) or huZCYTO18-2 (SEQ ID NO:35) or huZCYTO18-3 (SEQ ID NO:36). The peptides were synthesized using an Applied Biosystems Model 431A peptide synthesizer (Applied Biosystems, Inc., Foster City, Calif.) according to manufacturer's instructions. The peptides huZCYTO18-1, huZCYTO18-2, and huZCYTO18-3 were then conjugated to the carrier protein maleimide-activated keyhole limpet hemocyanin (KLH) through cysteine residues (Pierce, Rockford, Ill.). The rabbits were each given an initial intraperitoneal (IP) injection of 200 µg of conjugated peptide in Complete Freund's Adjuvant (Pierce, Rockford, Ill.) followed by booster IP injections of 100 µg conjugated peptide in Incomplete Freund's Adjuvant every three weeks. Seven to ten days after the administration of the third booster injection, the animals were bled and the serum was collected. The rabbits were then boosted and bled every three weeks.

The huZCYTO18 peptide-specific Rabbit seras were characterized by an ELISA titer check using 1 µg/ml of the peptide used to make the antibody as an antibody target. The 2 rabbit seras to the huZCYTO18-1 peptide (SEQ ID NO:34) have titer to their specific peptide at a dilution of 1:5 E6 (1:5,000,000).

The huZCYTO18-1 peptide-specific antibodies were affinity purified from the rabbit serum using an EPDXY-SEPHAROSE 6B peptide column (Pharmacia LKB) that was prepared using 10 mg of the respective peptides per gram EPDXY-SEPHAROSE 6B, followed by dialysis in PBS overnight. Peptide-specific huZCYTO18 antibodies were characterized by an ELISA titer check using 1 µg/ml of the appropriate peptide as an antibody target. The huZCYTO18-1 peptide-specific antibodies have a lower limit of detection (LLD) of 500 pg/ml by ELISA on its appropriate antibody target. The huZCYTO18-1 peptide-specific antibodies recognize full-length recombinant protein (BV produced) by reducing Western Blot analysis.

Example 17

Construction of Human ZCYTO18 Transgenic Plasmids

Approximately 10 µg Zytrack vector containing the sequence confirmed human ZCYTO18 coding region was digested with FseI and AscI. The vector was then ethanol precipitated and the pellet was resuspended in TE. The released 540 by human ZCYTO18 fragment was isolated by running the digested vector on a 1.2% SeaPlaque gel and excising the fragment. DNA was purified using the QiaQuick (Qiagen) gel extraction kit.

The human ZCYTO18 fragment was then ligated into pTG12-8, our standard transgenic vector, which was previously digested with FseI and AscI. The pTG12-8 plasmid, designed for expression of a gene of interest in transgenic mice, contains an expression cassette flanked by 10 kb of MT-1 5' DNA and 7 kb of MT-1 3' DNA. The expression cassette comprises the MT-1 promoter, the rat insulin II intron, a polylinker for the insertion of the desired clone, and the human growth hormone poly A sequence.

About one microliter of the ligation reaction was electroporated into DH10B ElectroMax® competent cells (GIBCO BRL, Gaithersburg, Md.) according to manufacturer's direction, plated onto LB plates containing 100 µg/ml ampicillin, and incubated overnight at 37° C. Colonies were picked and grown in LB media containing 100 µg/ml ampicillin. Miniprep DNA was prepared from the picked clones and screened for the human ZCYTO18 insert by restriction digestion with FseI/AscI, and subsequent agarose gel electrophoresis. Maxipreps of the correct pTG12-8 human ZCYTO18 construct were performed.

A SalI fragment containing 5' and 3' flanking sequences, the MT promoter, the rat insulin II intron, human ZCYTO18 cDNA and the human growth hormone poly A sequence was prepared and used for microinjection into fertilized murine oocytes.

A second transgenic construct was made by subcloning as described above, the FseI/AscI fragment containing the human ZCYTO18 cDNA, into a lymphoid-specific transgenic vector pKFO51. The pKFO51 transgenic vector is derived from p1026X (Iritani, B. M., et al., *EMBO J.* 16:7019-31, 1997) and contains the T cell-specific lck proximal promoter, the B/T cell-specific immunoglobulin Eµ heavy chain enhancer, a polylinker for the insertion of the desired clone, and a mutated hGH gene that encodes an inactive growth hormone protein (providing 3' introns and a polyadenylation signal).

Maxi-prep DNA was digested with NotI, and this fragment, containing the lck proximal promoter, immunoglobulin Eµ enhancer, human ZCYTO18 cDNA, and the mutated hGH gene was prepared to be used for microinjection into fertilized murine oocytes.

Construction of Mouse ZCYTO18 Transgenic Plasmids

Transgenic constructs were also made for mouse ZCYTO18. Oligonucleotides were designed to generate a PCR fragment containing a consensus Kozak sequence and the exact mouse ZCYTO18 coding region. These oligonucleotides were designed with an FseI site at the 5' end and an AscI site at the 3' end to facilitate cloning into pKFO51, a lymphoid-specific transgenic vector containing the EuLCK promoter to drive expression of ZCYTO18.

PCR reactions were carried out with 200 ng mouse ZCYTO18 template (SEQ ID NO:37) and oligonucleotides ZC37,125 (SEQ ID NO:39) and ZC37,126 (SEQ ID NO:40). A PCR reaction was performed using Advantage™ cDNA polymerase (Clontech) under the following conditions: 95° C. for 5 minutes; 15 cycles of 95° C. for 60 seconds, 60° C. for 60 seconds, and 72° C. for 90 seconds; and 72° C. for 7 minutes. PCR products were separated by agarose gel electrophoresis and purified using a QiaQuick (Qiagen) gel extraction kit. The isolated, 540 bp, DNA fragment was digested with FseI and AscI (Boerhinger-Mannheim), ethanol precipitated and cloned into pKFO51 as described above. A correct clone of pKFO51 mouse ZCYTO18 was verified by sequencing, and a maxiprep of this clone was performed and prepared as above for injection.

Example 18

Baculovirus Expression of zCyto18-CEE

An expression vector, zCyto18-CEE/pZBV32L, was prepared to express zCyto18-CEE polypeptides in insect cells. zCyto18-CEE/pZBV32L was designed to express a zCyto18 polypeptide with a C-terminal GLU-GLU tag (SEQ ID NO:14). This construct can be used to determine the N-terminal amino acid sequence of zCyto18 after the signal peptide has been cleaved off.

A. Construction of zCyto18-CEE/pZBV32L

A 561 by zCyto18 fragment containing BamHI and XbaI restriction sites on the 5' and 3' ends, respectively, was generated by PCR amplification from a plasmid containing zCyto18 cDNA using primers ZC28,348 (SEQ ID NO:41) and ZC28,345 (SEQ ID NO:42). The PCR reaction conditions were as follows: 1 cycle at 94° C. for 5 minutes; 35 cycles of 94° C. for 90 seconds, 60° C. for 120 seconds, and 72° C. for 180 seconds; 1 cycle at 72° C. for 10 min; followed by 4° C. soak. The fragment was visualized by gel electrophoresis (1% agarose). The band was excised and then extracted using a QIAquick™ Gel Extraction Kit (Qiagen, Cat. No. 28704). The cDNA was digested using BamHI and XbaI and then was ligated into the vector pZBV32L. The pZBV32L vector is a modification of the pFastBac1 ™ (Life Technologies) expression vector, where the polyhedron promoter has been removed and replaced with the late activating Basic Protein Promoter, and the coding sequence for the Glu-Glu tag as well as a stop signal was inserted at the 3' end of the multiple cloning region. Approximately 68 nanograms of the restriction digested zCyto18 insert and about 100 ng of the corresponding pZBV32L vector were ligated overnight at 16° C. The ligation mix was diluted 10 fold in water and 1 fmol of the diluted ligation mix was transformed into ElectoMAX™ DH12s™ cells (Life Technologies, Cat. No. 18312-017) by electroporation at 400 Ohms, 2V and 25 μF in a 2 mm gap electroporation cuvette (BTX, Model No. 620). The transformed cells were diluted in 450 μl of SOC media (2% Bacto Tryptone, 0.5% Bacto Yeast Extract, 10 ml 1M NaCl, 1.5 mM KCl, 10 mM MgCl$_2$, 10 mM MgSO$_4$ and 20 mM glucose) and 100 μl of the dilution were plated onto LB plates containing 100 μg/ml ampicillin. Clones were analyzed by PCR and two positive clones were selected to be outgrown and purified using a QIAprep® Spin Miniprep Kit (Qiagen, Cat. No. 27106). Two μl of each of the positive clones were transformed into 20 μl DH10Bac™ Max Efficiency® competent cells (GIBCO-BRL Cat. No. 10361-012) by heat shock for 45 seconds in a 42° C. heat block. The transformed DH10Bac™ cells were diluted in 980 μl SOC media (2% Bacto Tryptone, 0.5% Bacto Yeast Extract, 10 ml 1M NaCl, 1.5 mM KCl, 10 mM MgCl$_2$, 10 mM MgSO$_4$ and 20 mM glucose) and 100 μl were plated onto Luria Agar plates containing 50 μg/ml kanamycin, 7 μg/ml gentamicin, 10 μg/ml tetracycline, 40 μg/mL IPTG and 200 μg/mL Bluo Gal. The plates were incubated for 48 hours at 37° C. A color selection was used to identify those cells having transposed viral DNA (referred to as a "bacmid"). Those colonies, which were white in color, were picked for analysis. Colonies were analyzed by PCR and positive colonies (containing desired bacmid) were selected for outgrowth and purified using a QIAprep® Spin Miniprep Kit (Qiagen, Cat. No. 27106). Clones were screened for the correct insert by amplifying DNA using primers to the transposable element in the bacmid via PCR using primers ZC447 (SEQ ID NO:43) and ZC976 (SEQ ID NO:44). The PCR reaction conditions were as follows: 1 cycle at 94° C. for 5 minutes; 30 cycles of 94° C. for 60 seconds, 50° C. for 90 seconds, and 72° C. for 180 seconds; 1 cycle at 72° C. for 10 min; followed by 4° C. soak. The PCR product was run on a 1% agarose gel to check the insert size. Those having the correct insert were used to transfect *Spodoptera Frugiperda* (Sf9) cells.

B. Transfection

Sf9 cells were seeded at 1×10$^6$ cells per well in a 6-well plate and allowed to attach for 1 hour at 27° C. Five microliters of bacmid DNA were diluted with 100 μl Sf-900 II SFM (Life Technologies). Twenty μl of Lipofectamine™ Reagent (Life Technologies, Cat. No. 18324-012) were diluted with 100 μSf-900 II SFM. The bacmid DNA and lipid solutions were gently mixed and incubated 30-45 minutes at room temperature. The media from one well of cells was aspirated, the cells were washed 1× with 2 ml fresh Sf-900 II SFM media. Eight hundred microliters of Sf-900 II SFM was added to the lipid-DNA mixture. The wash media was aspirated and the DNA-lipid mix added to the cells. The cells were incubated at 27° C. overnight. The DNA-lipid mix was aspirated and 2 ml of Sf-900 II media was added to each plate. The plates were incubated at 27° C., 90% humidity, for 96 hours after which the virus was harvested.

C. Amplification

Sf9 cells were seeded at 1×10$^6$ cells per well in a 6-well plate. 50 μl of virus from the transfection plate were placed in the well and the plate was incubated at 27° C., 90% humidity, for 96 hours after which the virus was harvested.

Sf9 cells were grown in 50 ml Sf-900 II SFM in a 125 ml shake flask to an approximate density of 1×10$^6$ cells/ml. They were then infected with 100 μl of the viral stock from the above plate and incubated at 27° C. for 3 days after which time the virus was harvested.

Example 19

Purification of Zcyto18-Cee from Sf9 Cells

The following procedure was used for purifying zCyto 18 polypeptides containing C-terminal Glu-Glu (EE) tags (SEQ ID NO:14), that were expressed in baculovirus. Conditioned media from Sf9 cells expressing zCyto18-CEE (Example 18) was filtered using a 0.22 μm Steriflip™ filter (Millipore) and one Complete™ protease inhibitor cocktail tablet (Boehringer) was added for every 50 mL of media. Total target protein concentrations of the concentrated conditioned media were determined via SDS-PAGE and Western blot analysis using an anti-EE antibody (produced in-house) followed by a secondary anti-mIg HRP conjugated antibody.

Batch purification was accomplished by adding 250 μl of Protein G Sepharose® 4 Fast Flow (Pharmacia) which was treated with anti-EE antibody (Protein G Sepharose/anti-EE beads), to 40 mLs of Sf9 conditioned media. To capture the ZCYTO18-CEE, the media-bead mixture was rocked overnight at 4° C. The beads were spun out of the media at 1000 RPM for 10 minutes in a Beckman GS6R centrifuge. The beads were washed using the following scheme (centrifugation and aspiration steps were done after each wash): 1× with 1 mL cell lysis buffer (150 mM Sodium Chloride, 50 mM Tris pH 8.0, and 1% NP-40); 1× with 1 mL wash buffer (650 mM Sodium Chloride, 50 mM Tris pH 8.0, and 1% NP-40); 1× with 1 mL cell lysis buffer. The beads were then suspended in 500 µl cell lysis buffer and submitted for N-terminal sequencing.

Example 20

N-terminal Amino Acid Sequence Analysis

Standard automated N-terminal polypeptide sequencing (Edman degradation) was performed using reagents from Applied Biosystems. N-terminal sequence analysis was performed on a Model 494 Protein Sequencer System (Applied Biosystems, Inc., Foster City, Calif.). Data analysis was performed with Model 610A Data Analysis System for Protein Sequencing, version 2.1a (Applied Biosystems).

A purified human ZCYTO18-CEE sample was supplied as captured on Protein G Sepharose/anti-EE beads (Example 19). The beads were placed in reducing SDS PAGE sample buffer and on a boiling water bath before running on SDS PAGE, using a Novex SDS PAGE system (4-12% Bis-Tris MES NuPAGE; Invitrogen) as per manufacturer's instructions. The gel was electrotransferred to a Novex PVDF membrane (Invitrogen), and Coomassie blue stained (Sigma, St. Louis, Mo.) using standard methods. Corresponding anti-EE Western blots were performed to identify the ZCYTO18 band for N-terminal protein sequencing. The mouse anti-EE IgG HRP conjugated antibody used was produced in house.

N-terminal sequence analysis of the secreted ZCYTO18 polypeptide verified the predicted cleavage site of the signal sequence resulting in a mature start of the ZCYTO18 precursor sequence at 22 (Ala) as shown in SEQ ID NO:3.

Example 21

Construction of BaF3 Cells Expressing the CRF2-4 Receptor (BaF3/CRF2-4 Cells) and BaF3 Cells Expressing the CRF2-4 Receptor with the Zcytor11 Receptor (BaF3/CRF2-4/Zcytor11 Cells)

BaF3 cells expressing the full-length CFR2-4 receptor were constructed, using 30 µg of a CFR2-4 expression vector, described below. The BaF3 cells expressing the CFR2-4 receptor were designated as BaF3/CFR2-4. These cells were used as a control, and were further transfected with full-length zcytor11 receptor (SEQ ID NO:18 and SEQ ID NO:19) (U.S. Pat. No. 5,965,704) and used to construct a screen for ZCYTO18 activity as described below. This cell assay system can be used to assess ZCYTO18 activity and readily screen for the activity of ZCYTO18 variants.

A. Construction of BaF3 Cells Expressing the CRF2-4 Receptor

The full-length cDNA sequence of CRF2-4 (Genbank Accession No. Z17227) was isolated from a Daudi cell line cDNA library, and then cloned into an expression vector pZP7P using standard methods.

BaF3, an interleukin-3 (IL-3) dependent pre-lymphoid cell line derived from murine bone marrow (Palacios and Steinmetz, *Cell* 41: 727-734, 1985; Mathey-Prevot et al., *Mol. Cell. Biol.* 6: 4133-4135, 1986), was maintained in complete media (RPMI medium (JRH Bioscience Inc., Lenexa, Kans.) supplemented with 10% heat-inactivated fetal calf serum, 2 ng/ml murine IL-3 (mIL-3) (R & D, Minneapolis, Minn.), 2 mM L-glutaMax-1™ (Gibco BRL), 1 mM Sodium Pyruvate (Gibco BRL), and PSN antibiotics (GIBCO BRL)). Prior to electroporation, CRF2-4/pZP7P was prepared and purified using a Qiagen Maxi Prep kit (Qiagen) as per manufacturer's instructions. For electroporation, BaF3 cells were washed once in serum-free RPMI media and then resuspended in serum-free RPMI media at a cell density of $10^7$ cells/ml. One ml of resuspended BaF3 cells was mixed with 30 µg of the CRF2-4/pZP7P plasmid DNA and transferred to separate disposable electroporation chambers (GIBCO BRL). Following a 15-minute incubation at room temperature the cells were given two serial shocks (800 lFad/300 V.; 1180 lFad/300 V.) delivered by an electroporation apparatus (CELL-PORATOR™; GIBCO BRL). After a 5-minute recovery time, the electroporated cells were transferred to 50 ml of complete media and placed in an incubator for 15-24 hours (37° C., 5% $CO_2$). The cells were then spun down and resuspended in 50 ml of complete media containing 2 µg/ml puromycin in a T-162 flask to isolate the puromycin-resistant pool. Pools of the transfected BaF3 cells, hereinafter called BaF3/CRF2-4 cells, were assayed for signaling capability as described below. Moreover these cells were further transfected with zcytor11 receptor as described below.

B. Construction of BaF3 Cells Expressing CRF2-4 and Zcytor11 Receptors

BaF3/CRF2-4 cells expressing the full-length zcytor11 receptor were constructed as per Example 21A above, using 30 µg of an expression vector containing zcytor11 cDNA (SEQ ID NO:18). Following recovery, transfectants were selected using 200 µg/ml zeocin and 2 µg/ml puromycin. The BaF3/CRF2-4 cells expressing the zcytor11 receptor were designated as BaF3/CRF2-4/zcytor11 cells. These cells were used to screen for ZCYTO18 activity (Example 22).

Example 22

Screening for Zcyto18 Activity Using BaF3/CRF2-4/Zcytor11 Cells Using an Alamar Blue Proliferation Assay A. Screening for Zcyto18 Activity Using BaF3/CRF2-4/Zcytor11 Cells Using an Alamar Blue Proliferation Assay Purified ZCYTO18-CEE (Example 9) was used to test for the presence of proliferation activity as described below BaF3/CRF2-4/zcytor11 cells were spun down and washed in the complete media, described in Example 21A above, but without mIL-3 (hereinafter referred to as "mIL-3 free media"). The cells were spun and washed 3 times to ensure the removal of the mIL-3 Cells were then counted in a hemacytometer. Cells were plated in a 96-well format at 5000 cells per well in a volume of 100 µl per well using the mIL-3 free media.

Proliferation of the BaF3/CRF2-4/zcytor11 cells was assessed using ZCYTO18-CEE protein diluted with mIL-3 free media to 50, 10, 2, 1, 0.5, 0.25, 0.13, 0.06 ng/ml concentrations. 100 µl of the diluted protein was added to the BaF3/CRF2-4/zcytor11 cells. The total assay volume is 200 µl. The assay plates were incubated at 37° C., 5% $CO_2$ for 3 days at which time Alamar Blue (Accumed, Chicago, Ill.) was added at 20 µl/well. Plates were again incubated at 37° C., 5% $CO_2$ for 24 hours. Alamar Blue gives a fluourometric readout based on number of live cells, and is thus a direct measurement of cell proliferation in comparison to a negative control.

Plates were again incubated at 37° C., 5% $CO_2$ for 24 hours. Plates were read on the Fmax™ plate reader (Molecular Devices Sunnyvale, Calif.) using the SoftMax™ Pro program, at wavelengths 544 (Excitation) and 590 (Emmission). Results confirmed the dose-dependent proliferative response of the BaF3/CRF2-4/zcytor11 cells to ZCYTO18-CEE. The response, as measured, was approximately 15-fold over background at the high end of 50 ng/ml down to a 2-fold induction at the low end of 0.06 ng/ml. The BaF3 wild type cells, and BaF3/CRF2-4 cells did not proliferate in response to ZCYTO18-CEE, showing that ZCYTO18 is specific for the CRF2-4/zcytor11 heterodimeric receptor.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of producing an antibody to a polypeptide comprising:
    inoculating an animal with a peptide consisting of amino acids 145 (Glu) to 150 (Lys) of SEQ ID NO:3; wherein the polypeptide elicits an immune response in the animal to produce the antibody; and
    isolating the antibody from the animal.

2. An isolated antibody produced by the method of claim 1, which specifically binds to a polypeptide of SEQ ID NO:2 or SEQ ID NO:3.

3. An isolated antibody that specifically binds to an epitope of IL10-related T-cell derived inducible factor (IL-TIF), wherein such epitope consists of amino acids 145 (Glu) to 150 (Lys) of SEQ ID NO:3.

4. The antibody of claim 3, wherein the antibody antagonizes IL-TIF activity.

5. The antibody of claim 4, wherein the antibody is a monoclonal antibody.

6. The antibody of claim 4, wherein the antibody is an antibody fragment.

7. A pharmaceutical composition comprising the antibody of claim 4.

8. The pharmaceutical composition of claim 7, wherein the antibody if a monoclonal antibody.

9. The pharmaceutical composition of claim 7, wherein the antibody is an antibody fragment.

* * * * *

UNITED STATES PATENT AND TRADEMARK OFFICE
CERTIFICATE OF CORRECTION

| | | |
|---|---|---|
| PATENT NO. | : 8,124,077 B2 | Page 1 of 1 |
| APPLICATION NO. | : 12/499636 | |
| DATED | : February 28, 2012 | |
| INVENTOR(S) | : Scott R. Presnell et al. | |

It is certified that error appears in the above-identified patent and that said Letters Patent is hereby corrected as shown below:

At column 112, claim number 8, line number 33, please change "antibody if a monoclonal antibody" to --antibody is a monoclonal antibody--

Signed and Sealed this
Seventeenth Day of April, 2012

David J. Kappos
*Director of the United States Patent and Trademark Office*

SEQUENCE LISTING

```
<160> NUMBER OF SEQ ID NOS: 44

<210> SEQ ID NO 1
<211> LENGTH: 1116
<212> TYPE: DNA
<213> ORGANISM: Homo sapiens
<220> FEATURE:
<221> NAME/KEY: CDS
<222> LOCATION: (21)...(557)

<400> SEQUENCE: 1
tcgagttaga attgtctgca atg gcc gcc ctg cag aaa tct gtg agc tct ttc       53
                     Met Ala Ala Leu Gln Lys Ser Val Ser Ser Phe
                       1               5                  10 ctt atg ggg acc ctg gcc acc agc tgc ctc ctt ctc ttg gcc ctc ttg      101
Leu Met Gly Thr Leu Ala Thr Ser Cys Leu Leu Leu Leu Ala Leu Leu
             15                  20                  25 gta cag gga gga gca gct gcg ccc atc agc tcc cac tgc agg ctt gac      149
Val Gln Gly Gly Ala Ala Ala Pro Ile Ser Ser His Cys Arg Leu Asp
         30                  35                  40 aag tcc aac ttc cag cag ccc tat atc acc aac cgc acc ttc atg ctg      197
Lys Ser Asn Phe Gln Gln Pro Tyr Ile Thr Asn Arg Thr Phe Met Leu
     45                  50                  55 gct aag gag gct agc ttg gct gat aac aac aca gac gtt cgt ctc att      245
Ala Lys Glu Ala Ser Leu Ala Asp Asn Asn Thr Asp Val Arg Leu Ile
 60                  65                  70                  75 ggg gag aaa ctg ttc cac gga gtc agt atg agt gag cgc tgc tat ctg      293
Gly Glu Lys Leu Phe His Gly Val Ser Met Ser Glu Arg Cys Tyr Leu
                 80                  85                  90 atg aag cag gtg ctg aac ttc acc ctt gaa gaa gtg ctg ttc cct caa      341
Met Lys Gln Val Leu Asn Phe Thr Leu Glu Glu Val Leu Phe Pro Gln
             95                 100                 105 tct gat agg ttc cag cct tat atg cag gag gtg gtg ccc ttc ctg gcc      389
Ser Asp Arg Phe Gln Pro Tyr Met Gln Glu Val Val Pro Phe Leu Ala
         110                 115                 120 agg ctc agc aac agg cta agc aca tgt cat att gaa ggt gat gac ctg      437
Arg Leu Ser Asn Arg Leu Ser Thr Cys His Ile Glu Gly Asp Asp Leu
     125                 130                 135 cat atc cag agg aat gtg caa aag ctg aag gac aca gtg aaa aag ctt      485
His Ile Gln Arg Asn Val Gln Lys Leu Lys Asp Thr Val Lys Lys Leu
 140                 145                 150                 155 gga gag agt gga gag atc aaa gca att gga gaa ctg gat ttg ctg ttt      533
Gly Glu Ser Gly Glu Ile Lys Ala Ile Gly Glu Leu Asp Leu Leu Phe
                 160                 165                 170 atg tct ctg aga aat gcc tgc att tgaccagagc aaagctgaaa atgaataac      587
Met Ser Leu Arg Asn Ala Cys Ile
             175 taacccctt tccctgctag aaataacaat tagatgcccc aaagcgattt tttttaacca     647
aaaggaagat gggaagccaa actccatcat gatgggtgga ttccaaatga accctgcgt      707 tagttacaaa ggaaaccaat gccacttttg tttataagac cagaaggtag actttctaag     767
```

```
catagatatt tattgataac atttcattgt aactggtgtt ctatacacag aaaacaattt       827 atttttaaa taattgtctt tttccataaa aaagattact ttccattcct ttaggggaaa        887 aaaccctaa atagcttcat gtttccataa tcagtacttt atatttataa atgtatttat        947
tattattata agactgcatt ttatttatat cattttatta atatggattt atttatagaa      1007
acatcattcg atattgctac ttgagtgtaa ggctaatatt gatatttatg acaataatta      1067
tagagctata acatgtttat ttgacctcaa taaacacttg gatatccta                 1116
```

<210> SEQ ID NO 2
<211> LENGTH: 179
<212> TYPE: PRT
<213> ORGANISM: Homo sapiens

<400> SEQUENCE: 2

```
Met Ala Ala Leu Gln Lys Ser Val Ser Ser Phe Leu Met Gly Thr Leu
 1               5                   10                  15

Ala Thr Ser Cys Leu Leu Leu Ala Leu Leu Val Gln Gly Gly Ala
                20                  25                  30

Ala Ala Pro Ile Ser Ser His Cys Arg Leu Asp Lys Ser Asn Phe Gln
            35                  40                  45

Gln Pro Tyr Ile Thr Asn Arg Thr Phe Met Leu Ala Lys Glu Ala Ser
        50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
    130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile
```

<210> SEQ ID NO 3
<211> LENGTH: 167
<212> TYPE: PRT
<213> ORGANISM: Homo sapiens

<400> SEQUENCE: 3

```
Met Gly Thr Leu Ala Thr Ser Cys Leu Leu Leu Ala Leu Leu Val
 1               5                   10                  15

Gln Gly Gly Ala Ala Ala Pro Ile Ser Ser His Cys Arg Leu Asp Lys
                20                  25                  30

Ser Asn Phe Gln Gln Pro Tyr Ile Thr Asn Arg Thr Phe Met Leu Ala
            35                  40                  45

Lys Glu Ala Ser Leu Ala Asp Asn Asn Thr Asp Val Arg Leu Ile Gly
        50                  55                  60

Glu Lys Leu Phe His Gly Val Ser Met Ser Glu Arg Cys Tyr Leu Met
65                  70                  75                  80

Lys Gln Val Leu Asn Phe Thr Leu Glu Glu Val Leu Phe Pro Gln Ser
```

```
            85                  90                  95
Asp Arg Phe Gln Pro Tyr Met Gln Glu Val Val Pro Phe Leu Ala Arg
                100                 105                 110

Leu Ser Asn Arg Leu Ser Thr Cys His Ile Glu Gly Asp Asp Leu His
        115                 120                 125

Ile Gln Arg Asn Val Gln Lys Leu Lys Asp Thr Val Lys Lys Leu Gly
    130                 135                 140

Glu Ser Gly Glu Ile Lys Ala Ile Gly Glu Leu Asp Leu Leu Phe Met
145                 150                 155                 160

Ser Leu Arg Asn Ala Cys Ile
            165

<210> SEQ ID NO 4
<211> LENGTH: 501
<212> TYPE: DNA
<213> ORGANISM: Artificial Sequence
<220> FEATURE:
<223> OTHER INFORMATION: Degenerate polynucleotide of ZCYTO18
<221> NAME/KEY: misc_feature
<222> LOCATION: (1)...(501)
<223> OTHER INFORMATION: n = A,T,C or G

<400> SEQUENCE: 4
atgggnacny tngcnacnws ntgyytnytn ytnytngcny tnytngtnca rggnggngcn      60
gcngcnccna thwsnwsnca ytgymgnytn gayaarwsna ayttycarca rccntayath     120
acnaaymgna cnttyatgyt ngcnaargar gcnwsnytng cngayaayaa yacngaygtn     180
mgnytnathg gngaraaryt nttycayggn gtnwsnatgw sngarmgntg ytayytnatg     240
aarcargtny tnaayttyac nytngargar gtnytnttyc cncarwsnga ymgnttycar     300
ccntayatgc argargtngt nccnttyytn gcnmgnytnw snaaymgnyt nwsnacntgy     360
cayathgarg gngaygayyt ncayathcar mgnaaygtnc araarytnaa rgayacngtn     420
aaraarytng gngarwsngg ngarathaar gcnathggng arytngayyt nytnttyatg     480
wsnytnmgna aygcntgyat h                                               501

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide primer ZC25840

<400> SEQUENCE: 5
ctggatatgc aggtcatcac cttc                                             24

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide primer ZC25841

<400> SEQUENCE: 6
tcgagttaga attgtctgca atgg                                             24

<210> SEQ ID NO 7
<211> LENGTH: 23
<212> TYPE: DNA
<213> ORGANISM: Artificial Sequence
<220> FEATURE:
<223> OTHER INFORMATION: Oligonucleotide primer ZC25838
```

-continued

<400> SEQUENCE: 7
aggttctcct tccccagtca cca                                               23

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide primer ZC25839

<400> SEQUENCE: 8
tagcctcctt agccagcatg aag                                               23

<210> SEQ ID NO 9
<211> LENGTH: 40
<212> TYPE: DNA
<213> ORGANISM: Artificial Sequence
<220> FEATURE:
<223> OTHER INFORMATION: Oligonucleotide primer ZC13946

<400> SEQUENCE: 9
ccctgcagtg atcaacatgg ccaagttgac cagtgccgtt                             40

<210> SEQ ID NO 10
<211> LENGTH: 45
<212> TYPE: DNA
<213> ORGANISM: Artificial Sequence
<220> FEATURE:
<223> OTHER INFORMATION: Oligonucleotide primer ZC13945

<400> SEQUENCE: 10
gcccatggac tagtttcgaa aggtcgagtg tcagtcctgc tcctc                       45

<210> SEQ ID NO 11
<211> LENGTH: 34
<212> TYPE: DNA
<213> ORGANISM: Artificial Sequence
<220> FEATURE:
<223> OTHER INFORMATION: Oligonucleotide primer ZC18698

<400> SEQUENCE: 11 ttttttctc gagacttttt tttttttttt tttt                                    34

<210> SEQ ID NO 12
<211> LENGTH: 18
<212> TYPE: DNA
<213> ORGANISM: Artificial Sequence
<220> FEATURE:
<223> OTHER INFORMATION: Oligonucleotide primer ZC26414

<400> SEQUENCE: 12
agctgcctcc ttctcttg                                                     18

<210> SEQ ID NO 13
<211> LENGTH: 18
<212> TYPE: DNA
<213> ORGANISM: Artificial Sequence
<220> FEATURE:
<223> OTHER INFORMATION: Oligonucleotide primer ZC26415

<400> SEQUENCE: 13
tagggctgct ggaagttg                                                     18

<210> SEQ ID NO 14
<211> LENGTH: 6
<212> TYPE: PRT

-continued

<213> ORGANISM: Artificial Sequence
<220> FEATURE:
<223> OTHER INFORMATION: Synthetic Glu-Glu (CEE) peptide Tag amino acid
      sequence

<400> SEQUENCE: 14

Glu Tyr Met Pro Met Glu
 1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic C-terminal FLAG peptide tag

<400> SEQUENCE: 15

Asp Tyr Lys Asp Asp Asp Asp Lys
 1               5

<210> SEQ ID NO 16
<211> LENGTH: 36
<212> TYPE: DNA
<213> ORGANISM: Artificial Sequence
<220> FEATURE:
<223> OTHER INFORMATION: Oligonucleotide primer ZC28590

<400> SEQUENCE: 16
ttgggtacct ctgcaatggc cgccctgcag aaatct                              36

<210> SEQ ID NO 17
<211> LENGTH: 33
<212> TYPE: DNA
<213> ORGANISM: Artificial Sequence
<220> FEATURE:
<223> OTHER INFORMATION: Oligonucleotide primer ZC28580

<400> SEQUENCE: 17
ttgggatcca atgcaggcat ttctcagaga cat                                 33

<210> SEQ ID NO 18
<211> LENGTH: 2831
<212> TYPE: DNA
<213> ORGANISM: Homo sapiens
<220> FEATURE:
<221> NAME/KEY: CDS
<222> LOCATION: (34)...(1755)

<400> SEQUENCE: 18
tagaggccaa gggagggctc tgtgccagcc ccg atg agg acg ctg ctg acc atc      54
                                    Met Arg Thr Leu Leu Thr Ile
                                     1               5 ttg act gtg gga tcc ctg gct gct cac gcc cct gag gac ccc tcg gat     102
Leu Thr Val Gly Ser Leu Ala Ala His Ala Pro Glu Asp Pro Ser Asp
         10                  15                  20 ctg ctc cag cac gtg aaa ttc cag tcc agc aac ttt gaa aac atc ctg     150
Leu Leu Gln His Val Lys Phe Gln Ser Ser Asn Phe Glu Asn Ile Leu
     25                  30                  35 acg tgg gac agc ggg cca gag ggc acc cca gac acg gtc tac agc atc     198
Thr Trp Asp Ser Gly Pro Glu Gly Thr Pro Asp Thr Val Tyr Ser Ile
 40                  45                  50                  55 gag tat aag acg tac gga gag agg gac tgg gtg gca aag aag ggc tgt     246
Glu Tyr Lys Thr Tyr Gly Glu Arg Asp Trp Val Ala Lys Lys Gly Cys
                 60                  65                  70 cag cgg atc acc cgg aag tcc tgc aac ctg acg gtg gag acg ggc aac     294
Gln Arg Ile Thr Arg Lys Ser Cys Asn Leu Thr Val Glu Thr Gly Asn

|   |   |
|---|---|
| ctc acg gag ctc tac tat gcc agg gtc acc gct gtc agt gcg gga ggc<br>Leu Thr Glu Leu Tyr Tyr Ala Arg Val Thr Ala Val Ser Ala Gly Gly<br>       90                     95                     100 | 342 |
| cgg tca gcc acc aag atg act gac agg ttc agc tct ctg cag cac act<br>Arg Ser Ala Thr Lys Met Thr Asp Arg Phe Ser Ser Leu Gln His Thr<br>105                   110                   115 | 390 |
| acc ctc aag cca cct gat gtg acc tgt atc tcc aaa gtg aga tcg att<br>Thr Leu Lys Pro Pro Asp Val Thr Cys Ile Ser Lys Val Arg Ser Ile<br>120                   125                   130                   135 | 438 |
| cag atg att gtt cat cct acc ccc acg cca atc cgt gca ggc gat ggc<br>Gln Met Ile Val His Pro Thr Pro Thr Pro Ile Arg Ala Gly Asp Gly<br>               140                   145                   150 | 486 |
| cac cgg cta acc ctg gaa gac atc ttc cat gac ctg ttc tac cac tta<br>His Arg Leu Thr Leu Glu Asp Ile Phe His Asp Leu Phe Tyr His Leu<br>               155                   160                   165 | 534 |
| gag ctc cag gtc aac cgc acc tac caa atg cac ctt gga ggg aag cag<br>Glu Leu Gln Val Asn Arg Thr Tyr Gln Met His Leu Gly Gly Lys Gln<br>               170                   175                   180 | 582 |
| aga gaa tat gag ttc ttc ggc ctg acc cct gac aca gag ttc ctt ggc<br>Arg Glu Tyr Glu Phe Phe Gly Leu Thr Pro Asp Thr Glu Phe Leu Gly<br>185                   190                   195 | 630 |
| acc atc atg att tgc gtt ccc acc tgg gcc aag gag agt gcc ccc tac<br>Thr Ile Met Ile Cys Val Pro Thr Trp Ala Lys Glu Ser Ala Pro Tyr<br>200                   205                   210                   215 | 678 |
| atg tgc cga gtg aag aca ctg cca gac cgg aca tgg acc tac tcc ttc<br>Met Cys Arg Val Lys Thr Leu Pro Asp Arg Thr Trp Thr Tyr Ser Phe<br>               220                   225                   230 | 726 |
| tcc gga gcc ttc ctg ttc tcc atg ggc ttc ctc gtc gca gta ctc tgc<br>Ser Gly Ala Phe Leu Phe Ser Met Gly Phe Leu Val Ala Val Leu Cys<br>               235                   240                   245 | 774 |
| tac ctg agc tac aga tat gtc acc aag ccg cct gca cct ccc aac tcc<br>Tyr Leu Ser Tyr Arg Tyr Val Thr Lys Pro Pro Ala Pro Pro Asn Ser<br>250                   255                   260 | 822 |
| ctg aac gtc cag cga gtc ctg act ttc cag ccg ctg cgc ttc atc cag<br>Leu Asn Val Gln Arg Val Leu Thr Phe Gln Pro Leu Arg Phe Ile Gln<br>265                   270                   275 | 870 |
| gag cac gtc ctg atc cct gtc ttt gac ctc agc ggc ccc agc agt ctg<br>Glu His Val Leu Ile Pro Val Phe Asp Leu Ser Gly Pro Ser Ser Leu<br>280                   285                   290                   295 | 918 |
| gcc cag cct gtc cag tac tcc cag atc agg gtg tct gga ccc agg gag<br>Ala Gln Pro Val Gln Tyr Ser Gln Ile Arg Val Ser Gly Pro Arg Glu<br>               300                   305                   310 | 966 |
| ccc gca gga gct cca cag cgg cat agc ctg tcc gag atc acc tac tta<br>Pro Ala Gly Ala Pro Gln Arg His Ser Leu Ser Glu Ile Thr Tyr Leu<br>               315                   320                   325 | 1014 |
| ggg cag cca gac atc tcc atc ctc cag ccc tcc aac gtg cca cct ccc<br>Gly Gln Pro Asp Ile Ser Ile Leu Gln Pro Ser Asn Val Pro Pro Pro<br>               330                   335                   340 | 1062 |
| cag atc ctc tcc cca ctg tcc tat gcc cca aac gct gcc cct gag gtc<br>Gln Ile Leu Ser Pro Leu Ser Tyr Ala Pro Asn Ala Ala Pro Glu Val<br>345                   350                   355 | 1110 |
| ggg ccc cca tcc tat gca cct cag gtg acc ccc gaa gct caa ttc cca<br>Gly Pro Pro Ser Tyr Ala Pro Gln Val Thr Pro Glu Ala Gln Phe Pro<br>360                   365                   370                   375 | 1158 |
| ttc tac gcc cca cag gcc atc tct aag gtc cag cct tcc tcc tat gcc<br>Phe Tyr Ala Pro Gln Ala Ile Ser Lys Val Gln Pro Ser Ser Tyr Ala<br>               380                   385                   390 | 1206 |
| cct caa gcc act ccg gac agc tgg cct ccc tcc tat ggg gta tgc atg<br>Pro Gln Ala Thr Pro Asp Ser Trp Pro Pro Ser Tyr Gly Val Cys Met | 1254 |

|  |  |  |  |  |  |  |  |  |  |  |  |  |  |  |  |
|---|---|---|---|---|---|---|---|---|---|---|---|---|---|---|---|
|  | 395 |  |  |  |  | 400 |  |  |  |  | 405 |  |  |  |  |
| gaa | ggt | tct | ggc | aaa | gac | tcc | ccc | act | ggg | aca | ctt | tct | agt | cct | aaa |
| Glu | Gly | Ser | Gly | Lys | Asp | Ser | Pro | Thr | Gly | Thr | Leu | Ser | Ser | Pro | Lys |
|  | 410 |  |  |  |  | 415 |  |  |  |  | 420 |  |  |  |  |

1302

| cac | ctt | agg | cct | aaa | ggt | cag | ctt | cag | aaa | gag | cca | cca | gct | gga | agc |
|---|---|---|---|---|---|---|---|---|---|---|---|---|---|---|---|
| His | Leu | Arg | Pro | Lys | Gly | Gln | Leu | Gln | Lys | Glu | Pro | Pro | Ala | Gly | Ser |
|  | 425 |  |  |  |  | 430 |  |  |  |  | 435 |  |  |  |  |

1350

| tgc | atg | tta | ggt | ggc | ctt | tct | ctg | cag | gag | gtg | acc | tcc | ttg | gct | atg |
|---|---|---|---|---|---|---|---|---|---|---|---|---|---|---|---|
| Cys | Met | Leu | Gly | Gly | Leu | Ser | Leu | Gln | Glu | Val | Thr | Ser | Leu | Ala | Met |
| 440 |  |  |  |  | 445 |  |  |  |  | 450 |  |  |  |  | 455 |

1398

| gag | gaa | tcc | caa | gaa | gca | aaa | tca | ttg | cac | cag | ccc | ctg | ggg | att | tgc |
|---|---|---|---|---|---|---|---|---|---|---|---|---|---|---|---|
| Glu | Glu | Ser | Gln | Glu | Ala | Lys | Ser | Leu | His | Gln | Pro | Leu | Gly | Ile | Cys |
|  |  |  |  |  | 460 |  |  |  |  | 465 |  |  |  |  | 470 |

1446

| aca | gac | aga | aca | tct | gac | cca | aat | gtg | cta | cac | agt | ggg | gag | gaa | ggg |
|---|---|---|---|---|---|---|---|---|---|---|---|---|---|---|---|
| Thr | Asp | Arg | Thr | Ser | Asp | Pro | Asn | Val | Leu | His | Ser | Gly | Glu | Glu | Gly |
|  |  |  | 475 |  |  |  |  | 480 |  |  |  |  | 485 |  |  |

1494

| aca | cca | cag | tac | cta | aag | ggc | cag | ctc | ccc | ctc | ctc | tcc | tca | gtc | cag |
|---|---|---|---|---|---|---|---|---|---|---|---|---|---|---|---|
| Thr | Pro | Gln | Tyr | Leu | Lys | Gly | Gln | Leu | Pro | Leu | Leu | Ser | Ser | Val | Gln |
|  |  | 490 |  |  |  |  | 495 |  |  |  |  | 500 |  |  |  |

1542

| atc | gag | ggc | cac | ccc | atg | tcc | ctc | cct | ttg | caa | cct | cct | tcc | ggt | cca |
|---|---|---|---|---|---|---|---|---|---|---|---|---|---|---|---|
| Ile | Glu | Gly | His | Pro | Met | Ser | Leu | Pro | Leu | Gln | Pro | Pro | Ser | Gly | Pro |
| 505 |  |  |  |  | 510 |  |  |  |  | 515 |  |  |  |  |  |

1590

| tgt | tcc | ccc | tcg | gac | caa | ggt | cca | agt | ccc | tgg | ggc | ctg | ctg | gag | tcc |
|---|---|---|---|---|---|---|---|---|---|---|---|---|---|---|---|
| Cys | Ser | Pro | Ser | Asp | Gln | Gly | Pro | Ser | Pro | Trp | Gly | Leu | Leu | Glu | Ser |
| 520 |  |  |  |  | 525 |  |  |  |  | 530 |  |  |  |  | 535 |

1638

| ctt | gtg | tgt | ccc | aag | gat | gaa | gcc | aag | agc | cca | gcc | cct | gag | acc | tca |
|---|---|---|---|---|---|---|---|---|---|---|---|---|---|---|---|
| Leu | Val | Cys | Pro | Lys | Asp | Glu | Ala | Lys | Ser | Pro | Ala | Pro | Glu | Thr | Ser |
|  |  |  |  | 540 |  |  |  |  | 545 |  |  |  |  | 550 |  |

1686

| gac | ctg | gag | cag | ccc | aca | gaa | ctg | gat | tct | ctt | ttc | aga | ggc | ctg | gcc |
|---|---|---|---|---|---|---|---|---|---|---|---|---|---|---|---|
| Asp | Leu | Glu | Gln | Pro | Thr | Glu | Leu | Asp | Ser | Leu | Phe | Arg | Gly | Leu | Ala |
|  |  |  |  | 555 |  |  |  |  | 560 |  |  |  |  | 565 |  |

1734

| ctg | act | gtg | cag | tgg | gag | tcc | tgagggaat | gggaaggct | tggtgcttcc |
|---|---|---|---|---|---|---|---|---|---|
| Leu | Thr | Val | Gln | Trp | Glu | Ser |  |  |  |
|  | 570 |  |  |  |  |  |  |  |  |

1785

| tccctgtccc | tacccagtgt | cacatccttg | gctgtcaatc | ccatgcctgc | ccatgccaca | 1845 |
|---|---|---|---|---|---|---|
| cactctgcga | tctggcctca | gacgggtgcc | cttgagagaa | gcagagggag | tggcatgcag | 1905 |
| ggccccctgcc | atgggtgcgc | tcctcaccgg | aacaaagcag | catgataagg | actgcagcgg | 1965 |
| gggagctctg | gggagcagct | tgtgtagaca | agcgcgtgct | cgctgagccc | tgcaaggcag | 2025 |
| aaatgacagt | gcaaggagga | aatgcaggga | aactcccgag | gtccagagcc | ccacctccta | 2085 |
| acaccatgga | ttcaaagtgc | tcagggaatt | gcctctcct | tgccccattc | ctggccagtt | 2145 |
| tcacaatcta | gctcgacaga | gcatgaggcc | cctgcctctt | ctgtcattgt | tcaaaggtgg | 2205 |
| gaagagagcc | tggaaaagaa | ccaggcctgg | aaaagaacca | gaaggaggct | gggcagaacc | 2265 |
| agaacaacct | gcacttctgc | caaggccagg | gccagcagga | cggcaggact | ctagggaggg | 2325 |
| gtgtggcctg | cagctcattc | ccagccaggg | caactgcctg | acgttgcacg | atttcagctt | 2385 |
| cattcctctg | atagaacaaa | gcgaaatgca | ggtccaccag | ggagggagac | acacaagcct | 2445 |
| tttctgcagg | caggagtttc | agaccctatc | ctgagaatgg | ggtttgaaag | gaaggtgagg | 2505 |
| gctgtggccc | ctgacgggt | acaataacac | actgtactga | tgtcacaact | ttgcaagctc | 2565 |
| tgccttgggt | tcagcccatc | tgggctcaaa | ttccagcctc | accactcaca | agctgtgtga | 2625 |
| cttcaaacaa | atgaaatcag | tgcccagaac | ctcggtttcc | tcatctgtaa | tgtggggatc | 2685 |
| ataacaccta | cctcatggag | ttgtggtgaa | gatgaaatga | agtcatgtct | ttaaagtgct | 2745 |
| taatagtgcc | tggtacatgg | gcagtgccca | ataaacggta | gctatttaaa | aaaaaaaaaa | 2805 | aaaaaaaaaa atagcggccg cctcga                                              2831

<210> SEQ ID NO 19
<211> LENGTH: 574
<212> TYPE: PRT
<213> ORGANISM: Homo sapiens

<400> SEQUENCE: 19

```
Met Arg Thr Leu Leu Thr Ile Leu Thr Val Gly Ser Leu Ala Ala His
  1               5                  10                  15

Ala Pro Glu Asp Pro Ser Asp Leu Leu Gln His Val Lys Phe Gln Ser
             20                  25                  30

Ser Asn Phe Glu Asn Ile Leu Thr Trp Asp Ser Gly Pro Glu Gly Thr
         35                  40                  45

Pro Asp Thr Val Tyr Ser Ile Glu Tyr Lys Thr Tyr Gly Glu Arg Asp
     50                  55                  60

Trp Val Ala Lys Lys Gly Cys Gln Arg Ile Thr Arg Lys Ser Cys Asn
 65                  70                  75                  80

Leu Thr Val Glu Thr Gly Asn Leu Thr Glu Leu Tyr Tyr Ala Arg Val
                 85                  90                  95

Thr Ala Val Ser Ala Gly Gly Arg Ser Ala Thr Lys Met Thr Asp Arg
            100                 105                 110

Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220

Arg Thr Trp Thr Tyr Ser Phe Ser Gly Ala Phe Leu Phe Ser Met Gly
225                 230                 235                 240

Phe Leu Val Ala Val Leu Cys Tyr Leu Ser Tyr Arg Tyr Val Thr Lys
                245                 250                 255

Pro Pro Ala Pro Pro Asn Ser Leu Asn Val Gln Arg Val Leu Thr Phe
            260                 265                 270

Gln Pro Leu Arg Phe Ile Gln Glu His Val Leu Ile Pro Val Phe Asp
        275                 280                 285

Leu Ser Gly Pro Ser Ser Leu Ala Gln Pro Val Gln Tyr Ser Gln Ile
    290                 295                 300

Arg Val Ser Gly Pro Arg Glu Pro Ala Gly Ala Pro Gln Arg His Ser
305                 310                 315                 320

Leu Ser Glu Ile Thr Tyr Leu Gly Gln Pro Asp Ile Ser Ile Leu Gln
                325                 330                 335

Pro Ser Asn Val Pro Pro Gln Ile Leu Ser Pro Leu Ser Tyr Ala
            340                 345                 350

Pro Asn Ala Ala Pro Glu Val Gly Pro Pro Ser Tyr Ala Pro Gln Val
        355                 360                 365

Thr Pro Glu Ala Gln Phe Pro Phe Tyr Ala Pro Gln Ala Ile Ser Lys
```

```
            370                 375                 380
Val Gln Pro Ser Ser Tyr Ala Pro Gln Ala Thr Pro Asp Ser Trp Pro
385                 390                 395                 400

Pro Ser Tyr Gly Val Cys Met Glu Gly Ser Gly Lys Asp Ser Pro Thr
                405                 410                 415

Gly Thr Leu Ser Ser Pro Lys His Leu Arg Pro Lys Gly Gln Leu Gln
            420                 425                 430

Lys Glu Pro Pro Ala Gly Ser Cys Met Leu Gly Gly Leu Ser Leu Gln
            435                 440                 445

Glu Val Thr Ser Leu Ala Met Glu Glu Ser Gln Glu Ala Lys Ser Leu
        450                 455                 460

His Gln Pro Leu Gly Ile Cys Thr Asp Arg Thr Ser Asp Pro Asn Val
465                 470                 475                 480

Leu His Ser Gly Glu Glu Gly Thr Pro Gln Tyr Leu Lys Gly Gln Leu
                485                 490                 495

Pro Leu Leu Ser Ser Val Gln Ile Glu Gly His Pro Met Ser Leu Pro
            500                 505                 510

Leu Gln Pro Pro Ser Gly Pro Cys Ser Pro Ser Asp Gln Gly Pro Ser
            515                 520                 525

Pro Trp Gly Leu Leu Glu Ser Leu Val Cys Pro Lys Asp Glu Ala Lys
530                 535                 540

Ser Pro Ala Pro Glu Thr Ser Asp Leu Glu Gln Pro Thr Glu Leu Asp
545                 550                 555                 560

Ser Leu Phe Arg Gly Leu Ala Leu Thr Val Gln Trp Glu Ser
                565                 570
```

<210> SEQ ID NO 20
<211> LENGTH: 39
<212> TYPE: DNA
<213> ORGANISM: Artificial Sequence
<220> FEATURE:
<223> OTHER INFORMATION: Oligonucleotide primer ZC26665

<400> SEQUENCE: 20
cacacaggcc ggccaccatg gccgccctgc agaaatctg                    39

<210> SEQ ID NO 21
<211> LENGTH: 37
<212> TYPE: DNA
<213> ORGANISM: Artificial Sequence
<220> FEATURE:
<223> OTHER INFORMATION: Oligonucleotide primer ZC26666

<400> SEQUENCE: 21
cacacaggcg cgcctcaaat gcaggcattt ctcagag                      37

<210> SEQ ID NO 22
<211> LENGTH: 18
<212> TYPE: DNA
<213> ORGANISM: Artificial Sequence
<220> FEATURE:
<223> OTHER INFORMATION: Oligonucleotide primer ZC14666

<400> SEQUENCE: 22
agccaccaag atgactga                                           18

<210> SEQ ID NO 23
<211> LENGTH: 22
<212> TYPE: DNA
<213> ORGANISM: Artificial Sequence
<220> FEATURE:

<223> OTHER INFORMATION: Oligonucleotide primer ZC14742

<400> SEQUENCE: 23
tgcatttggt aggtgcggtt ga                                        22

<210> SEQ ID NO 24
<211> LENGTH: 23
<212> TYPE: DNA
<213> ORGANISM: Artificial Sequence
<220> FEATURE:
<223> OTHER INFORMATION: Oligonucleotide primer ZC25963

<400> SEQUENCE: 24
agtcaacgca tgagtctctg aag                                       23

<210> SEQ ID NO 25
<211> LENGTH: 23
<212> TYPE: DNA
<213> ORGANISM: Artificial Sequence
<220> FEATURE:
<223> OTHER INFORMATION: Oligonucleotide primer ZC28354

<400> SEQUENCE: 25
accaacaaag agccattgac ttg                                       23

<210> SEQ ID NO 26
<211> LENGTH: 23
<212> TYPE: DNA
<213> ORGANISM: Artificial Sequence
<220> FEATURE:
<223> OTHER INFORMATION: Oligonucleotide primer ZC21195

<400> SEQUENCE: 26
gaggagacca taaccccga cag                                        23

<210> SEQ ID NO 27
<211> LENGTH: 23
<212> TYPE: DNA
<213> ORGANISM: Artificial Sequence
<220> FEATURE:
<223> OTHER INFORMATION: Oligonucleotide primer ZC21196

<400> SEQUENCE: 27
catagctccc accacacgat ttt                                       23

<210> SEQ ID NO 28
<211> LENGTH: 25
<212> TYPE: DNA
<213> ORGANISM: Artificial Sequence
<220> FEATURE:
<223> OTHER INFORMATION: Oligonucleotide primer ZC14063

<400> SEQUENCE: 28
caccagacat aatagctgac agact                                     25

<210> SEQ ID NO 29
<211> LENGTH: 21
<212> TYPE: DNA
<213> ORGANISM: Artificial Sequence
<220> FEATURE:
<223> OTHER INFORMATION: Oligonucleotide primer ZC17574

<400> SEQUENCE: 29
ggtrttgctc agcatgcaca c                                         21

<210> SEQ ID NO 30

```
<211> LENGTH: 24
<212> TYPE: DNA
<213> ORGANISM: Artificial Sequence
<220> FEATURE:
<223> OTHER INFORMATION: Oligonucleotide primer ZC17600

<400> SEQUENCE: 30
catgtaggcc atgaggtcca ccac                                              24

<210> SEQ ID NO 31
<211> LENGTH: 23
<212> TYPE: DNA
<213> ORGANISM: Artificial Sequence
<220> FEATURE:
<223> OTHER INFORMATION: Oligonucleotide primer ZC25964

<400> SEQUENCE: 31
gttcttgagt accccaacag tct                                               23

<210> SEQ ID NO 32
<211> LENGTH: 2149
<212> TYPE: DNA
<213> ORGANISM: Homo sapiens
<220> FEATURE:
<221> NAME/KEY: CDS
<222> LOCATION: (1)...(693)

<400> SEQUENCE: 32 atg atg cct aaa cat tgc ttt cta ggc ttc ctc atc agt ttc ttc ctt        48
Met Met Pro Lys His Cys Phe Leu Gly Phe Leu Ile Ser Phe Phe Leu
  1               5                  10                  15 act ggt gta gca gga act cag tca acg cat gag tct ctg aag cct cag        96
Thr Gly Val Ala Gly Thr Gln Ser Thr His Glu Ser Leu Lys Pro Gln
             20                  25                  30 agg gta caa ttt cag tcc cga aat ttt cac aac att ttg caa tgg cag       144
Arg Val Gln Phe Gln Ser Arg Asn Phe His Asn Ile Leu Gln Trp Gln
         35                  40                  45 cct ggg agg gca ctt act ggc aac agc agt gtc tat ttt gtg cag tac       192
Pro Gly Arg Ala Leu Thr Gly Asn Ser Ser Val Tyr Phe Val Gln Tyr
     50                  55                  60 aaa ata tat gga cag aga caa tgg aaa aat aaa gaa gac tgt tgg ggt       240
Lys Ile Tyr Gly Gln Arg Gln Trp Lys Asn Lys Glu Asp Cys Trp Gly
 65                  70                  75                  80 act caa gaa ctc tct tgt gac ctt acc agt gaa acc tca gac ata cag       288
Thr Gln Glu Leu Ser Cys Asp Leu Thr Ser Glu Thr Ser Asp Ile Gln
                 85                  90                  95 gaa cct tat tac ggg agg gtg agg gcg gcc tcg gct ggg agc tac tca       336
Glu Pro Tyr Tyr Gly Arg Val Arg Ala Ala Ser Ala Gly Ser Tyr Ser
            100                 105                 110 gaa tgg agc atg acg ccg cgg ttc act ccc tgg tgg gaa aca aaa ata       384
Glu Trp Ser Met Thr Pro Arg Phe Thr Pro Trp Trp Glu Thr Lys Ile
        115                 120                 125 gat cct cca gtc atg aat ata acc caa gtc aat ggc tct ttg ttg gta       432
Asp Pro Pro Val Met Asn Ile Thr Gln Val Asn Gly Ser Leu Leu Val
    130                 135                 140 att ctc cat gct cca aat tta cca tat aga tac caa aag gaa aaa aat       480
Ile Leu His Ala Pro Asn Leu Pro Tyr Arg Tyr Gln Lys Glu Lys Asn
145                 150                 155                 160 gta tct ata gaa gat tac tat gaa cta cta tac cga gtt ttt ata att       528
Val Ser Ile Glu Asp Tyr Tyr Glu Leu Leu Tyr Arg Val Phe Ile Ile
                165                 170                 175 aac aat tca cta gaa aag gag caa aag gtt tat gaa ggg gct cac aga       576
Asn Asn Ser Leu Glu Lys Glu Gln Lys Val Tyr Glu Gly Ala His Arg
            180                 185                 190
```

```
gcg gtt gaa att gaa gct cta aca cca cac tcc agc tac tgt gta gtg      624
Ala Val Glu Ile Glu Ala Leu Thr Pro His Ser Ser Tyr Cys Val Val
        195                 200                 205 gct gaa ata tat cag ccc atg tta gac aga aga agt cag aga agt gaa      672
Ala Glu Ile Tyr Gln Pro Met Leu Asp Arg Arg Ser Gln Arg Ser Glu
    210                 215                 220 gag aga tgt gtg gaa att cca tgacttgtgg aatttggcat tcagcaatgt         723
Glu Arg Cys Val Glu Ile Pro
225                 230 ggaaattcta aagctccctg agaacaggat gactcgtgtt tgaaggatct tatttaaaat    783
tgttttgta ttttcttaaa gcaatattca ctgttacacc ttggggactt ctttgtttat     843
ccattctttt atcctttata tttcatttta aactatattt gaacgacatt ccccccgaaa    903
aattgaaatg taaagatgag gcagagaata aagtgttcta tgaaattcag aactttattt    963
ctgaatgtaa catccctaat aacaaccttc attcttctaa tacagcaaaa taaaaattta   1023
acaaccaagg aatagtattt aagaaaatgt tgaataatt ttttaaaat agcattacag     1083
actgaggcgg tcctgaagca atggttttc actctcttat tgagccaatt aaattgacat    1143
tgctttgaca atttaaaact tctataaagg tgaatatttt tcatacattt ctattttata   1203
tgaatatact ttttatatat ttattattat taaatatttc tacttaatga atcaaaattt   1263
tgttttaaag tctactttat gtaaataaga acaggttttg gggaaaaaaa tcttatgatt   1323
tctggattga tatctgaatt aaaactatca acaacaagga agtctactct gtacaattgt   1383
ccctcattta aaagatatat taagcttttc ttttctgttt gttttttgttt tgtttagttt  1443
ttaatcctgt cttagaagaa cttatcttta ttctcaaaat taaatgtaat ttttttagtg   1503
acaaagaaga aaggaaacct cattactcaa tccttctggc caagagtgtc ttgcttgtgg   1563
cgccttcctc atctctatat aggaggatcc catgaatgat ggtttattgg gaactgctgg   1623
ggtcgacccc atacagagaa ctcagcttga agctggaagc acacagtggg tagcaggaga   1683
aggaccggtg ttggtaggtg cctacagaga ctatagagct agacaaagcc ctccaaactg   1743
gcccctcctg ctcactgcct ctcctgagta gaaatctggt gacctaaggc tcagtgcggt   1803
caacagaaag ctgccttctt cacttgaggc taagtcttca tatatgttta aggttgtctt   1863
tctagtgagg agatacatat cagagaacat ttgtacaatt ccccatgaaa attgctccaa   1923
agttgataac aatatagtcg gtgcttctag ttatatgcaa gtactcagtg ataaatggat   1983
taaaaaatat tcagaaatgt attgggggggt ggaggagaat aagaggcaga gcaagagcta   2043
gagaattggt ttccttgctt ccctgtatgc tcagaaaaca ttgatttgag catagacgca   2103
gagactgaaa aaaaaaaat gctcgagcgg ccgccatatc cttggt                   2149

<210> SEQ ID NO 33
<211> LENGTH: 231
<212> TYPE: PRT
<213> ORGANISM: Homo sapiens

<400> SEQUENCE: 33

Met Met Pro Lys His Cys Phe Leu Gly Phe Leu Ile Ser Phe Leu
1               5                   10                  15

Thr Gly Val Ala Gly Thr Gln Ser Thr His Glu Ser Leu Lys Pro Gln
            20                  25                  30

Arg Val Gln Phe Gln Ser Arg Asn Phe His Asn Ile Leu Gln Trp Gln
        35                  40                  45

Pro Gly Arg Ala Leu Thr Gly Asn Ser Ser Val Tyr Phe Val Gln Tyr
    50                  55                  60
```

```
Lys Ile Tyr Gly Gln Arg Gln Trp Lys Asn Lys Glu Asp Cys Trp Gly
 65                  70                  75                  80

Thr Gln Glu Leu Ser Cys Asp Leu Thr Ser Glu Thr Ser Asp Ile Gln
                 85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
        115                 120                 125

Asp Pro Pro Val Met Asn Ile Thr Gln Val Asn Gly Ser Leu Leu Val
    130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
        195                 200                 205

Ala Glu Ile Tyr Gln Pro Met Leu Asp Arg Arg Ser Gln Arg Ser Glu
    210                 215                 220

Glu Arg Cys Val Glu Ile Pro
225                 230

<210> SEQ ID NO 34
<211> LENGTH: 29
<212> TYPE: PRT
<213> ORGANISM: Artificial Sequence
<220> FEATURE:
<223> OTHER INFORMATION: Human ZCYTO18 peptide 1 (huZCYTO18-1)

<400> SEQUENCE: 34

Lys Glu Ala Ser Leu Ala Asp Asn Asn Thr Asp Val Arg Leu Ile Gly
 1               5                  10                  15

Glu Lys Leu Phe His Gly Val Ser Met Ser Glu Arg Cys
            20                  25

<210> SEQ ID NO 35
<211> LENGTH: 21
<212> TYPE: PRT
<213> ORGANISM: Artificial Sequence
<220> FEATURE:
<223> OTHER INFORMATION: Human ZCYTO18 peptide 2 (huZCYTO18-2)

<400> SEQUENCE: 35

Glu Glu Val Leu Phe Pro Gln Ser Asp Arg Phe Gln Pro Tyr Met Gln
 1               5                  10                  15

Glu Val Val Pro Cys
            20

<210> SEQ ID NO 36
<211> LENGTH: 24
<212> TYPE: PRT
<213> ORGANISM: Artificial Sequence
<220> FEATURE:
<223> OTHER INFORMATION: Human ZCYTO18 peptide 3 (huZCYTO18-3)

<400> SEQUENCE: 36

Cys Asn Val Gln Lys Leu Lys Asp Thr Val Lys Lys Leu Gly Glu Ser
 1               5                  10                  15

Gly Glu Ile Lys Ala Ile Gly Glu
```

<210> SEQ ID NO 37
<211> LENGTH: 778
<212> TYPE: DNA
<213> ORGANISM: mus musculus
<220> FEATURE:
<221> NAME/KEY: CDS
<222> LOCATION: (47)...(583)

<400> SEQUENCE: 37

```
aggctctcct ctcacttatc aactgttgac acttgtgcga tcggtg atg gct gtc        55
                                                   Met Ala Val
                                                    1 ctg cag aaa tct atg agt ttt tcc ctt atg ggg act ttg gcc gcc agc      103
Leu Gln Lys Ser Met Ser Phe Ser Leu Met Gly Thr Leu Ala Ala Ser
        5                  10                  15 tgc ctg ctt ctc att gcc ctg tgg gcc cag gag gca aat gcg ctg ccc      151
Cys Leu Leu Leu Ile Ala Leu Trp Ala Gln Glu Ala Asn Ala Leu Pro
 20                  25                  30                  35 gtc aac acc cgg tgc aag ctt gag gtg tcc aac ttc cag cag ccg tac      199
Val Asn Thr Arg Cys Lys Leu Glu Val Ser Asn Phe Gln Gln Pro Tyr
                 40                  45                  50 atc gtc aac cgc acc ttt atg ctg gcc aag gag gcc agc ctt gca gat      247
Ile Val Asn Arg Thr Phe Met Leu Ala Lys Glu Ala Ser Leu Ala Asp
             55                  60                  65 aac aac aca gat gtc cgg ctc atc ggg gag aaa ctg ttc cga gga gtc      295
Asn Asn Thr Asp Val Arg Leu Ile Gly Glu Lys Leu Phe Arg Gly Val
         70                  75                  80 aat gct aag gat cag tgc tac ctg atg aag cag gtg ctc aac ttc acc      343
Asn Ala Lys Asp Gln Cys Tyr Leu Met Lys Gln Val Leu Asn Phe Thr
     85                  90                  95 ctg gaa gac gtt ctg ctc ccc cag tca gac agg ttc cag ccc tac atg      391
Leu Glu Asp Val Leu Leu Pro Gln Ser Asp Arg Phe Gln Pro Tyr Met
100                 105                 110                 115 cag gag gtg gtg cct ttc ctg acc aaa ctc agc aat cag ctc agc tcc      439
Gln Glu Val Val Pro Phe Leu Thr Lys Leu Ser Asn Gln Leu Ser Ser
                120                 125                 130 tgt cac atc agc ggt gac gac cag aac atc cag aag aat gtc aga agg      487
Cys His Ile Ser Gly Asp Asp Gln Asn Ile Gln Lys Asn Val Arg Arg
            135                 140                 145 ctg aag gag aca gtg aaa aag ctt gga gag agt gga gag atc aag gcg      535
Leu Lys Glu Thr Val Lys Lys Leu Gly Glu Ser Gly Glu Ile Lys Ala
        150                 155                 160 att ggg gaa ctg gac ctg ctg ttt atg tct ctg aga aat gct tgc gtc      583
Ile Gly Glu Leu Asp Leu Leu Phe Met Ser Leu Arg Asn Ala Cys Val
    165                 170                 175 tgagcgagaa gaagctagaa acgaagaac tgctccttcc tgccttctaa aaagaacaat     643
aagatccctg aatggacttt tttactaaag gaaagtgaga agctaacgtc catcatcatt    703
agaagatttc acatgaaacc tggctcagtt gaaaagaaa atagtgtcaa gttgtccatg    763
agaccagagg tagac                                                    778
```

<210> SEQ ID NO 38
<211> LENGTH: 179
<212> TYPE: PRT
<213> ORGANISM: mus musculus

<400> SEQUENCE: 38

```
Met Ala Val Leu Gln Lys Ser Met Ser Phe Ser Leu Met Gly Thr Leu
 1               5                  10                  15
```

```
Ala Ala Ser Cys Leu Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
        35                  40                  45

Gln Pro Tyr Ile Val Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

Arg Gly Val Asn Ala Lys Asp Gln Cys Tyr Leu Met Lys Gln Val Leu
                85                  90                  95

Asn Phe Thr Leu Glu Asp Val Leu Leu Pro Ser Arg Phe Gln
            100                 105                 110

Pro Tyr Met Gln Glu Val Val Pro Phe Leu Thr Lys Leu Ser Asn Gln
            115                 120                 125

Leu Ser Ser Cys His Ile Ser Gly Asp Asp Gln Asn Ile Gln Lys Asn
        130                 135                 140

Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val

<210> SEQ ID NO 39
<211> LENGTH: 32
<212> TYPE: DNA
<213> ORGANISM: Artificial Sequence
<220> FEATURE:
<223> OTHER INFORMATION: Oligonucleotide primer ZC37125

<400> SEQUENCE: 39
ctatttggcc ggccaccatg gctgtcctgc ag                                    32

<210> SEQ ID NO 40
<211> LENGTH: 32
<212> TYPE: DNA
<213> ORGANISM: Artificial Sequence
<220> FEATURE:
<223> OTHER INFORMATION: Oligonucleotide primer ZC37126

<400> SEQUENCE: 40
cgtacgggcg cgcctcagac gcaagcattt ct                                    32

<210> SEQ ID NO 41
<211> LENGTH: 25
<212> TYPE: DNA
<213> ORGANISM: Artificial Sequence
<220> FEATURE:
<223> OTHER INFORMATION: Oligonucleotide primer ZC28348

<400> SEQUENCE: 41
cgggatcccg atggccgccc tgcag                                            25

<210> SEQ ID NO 42
<211> LENGTH: 28
<212> TYPE: DNA
<213> ORGANISM: Artificial Sequence
<220> FEATURE:
<223> OTHER INFORMATION: Oligonucleotide primer ZC28345

<400> SEQUENCE: 42
gctctagacc aatgcaggca tttctcag                                         28
```

```
<210> SEQ ID NO 43
<211> LENGTH: 17
<212> TYPE: DNA
<213> ORGANISM: Artificial Sequence
<220> FEATURE:
<223> OTHER INFORMATION: Oligonucleotide primer ZC447

<400> SEQUENCE: 43
taacaatttc acacagg                                                17

<210> SEQ ID NO 44
<211> LENGTH: 18
<212> TYPE: DNA
<213> ORGANISM: Artificial Sequence
<220> FEATURE:
<223> OTHER INFORMATION: Oligonucleotide primer ZC976

<400> SEQUENCE: 44
cgttgtaaaa cgacggcc                                               18
```